the present invention relates to metal complexes and to electronic devices, in particular organic electroluminescent devices, comprising these metal complexes.

(12) United States Patent
Stoessel et al.

(10) Patent No.: US 9,831,446 B2
(45) Date of Patent: Nov. 28, 2017

(54) METAL COMPLEXES

(71) Applicant: Merck Patent GmbH, Darmstadt (DE)

(72) Inventors: Philipp Stoessel, Frankfurt am Main (DE); Joachim Kaiser, Darmstadt (DE); Dominik Joosten, Frankfurt am Main (DE); Nils Koenen, Darmstadt (DE); Esther Breuning, Ober-Ramstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 273 days.

(21) Appl. No.: 14/434,167

(22) PCT Filed: Sep. 11, 2013

(86) PCT No.: PCT/EP2013/002726
§ 371 (c)(1),
(2) Date: Apr. 8, 2015

(87) PCT Pub. No.: WO2014/056564
PCT Pub. Date: Apr. 17, 2014

(65) Prior Publication Data
US 2015/0270500 A1     Sep. 24, 2015

(30) Foreign Application Priority Data
Oct. 9, 2012 (EP) .................................. 12006990

(51) Int. Cl.
*H01L 51/00*   (2006.01)
*C07F 15/00*   (2006.01)
*C09K 11/06*   (2006.01)
*H01L 51/50*   (2006.01)
*H01L 51/52*   (2006.01)

(52) U.S. Cl.
CPC ...... *H01L 51/0085* (2013.01); *C07F 15/0033* (2013.01); *C07F 15/0086* (2013.01); *C09K 11/06* (2013.01); *H01L 51/0034* (2013.01); *H01L 51/0087* (2013.01); *H01L 51/0094* (2013.01); *C09K 2211/185* (2013.01); *H01L 51/006* (2013.01); *H01L 51/0058* (2013.01); *H01L 51/0059* (2013.01); *H01L 51/0067* (2013.01); *H01L 51/0072* (2013.01); *H01L 51/0077* (2013.01); *H01L 51/506* (2013.01); *H01L 51/5016* (2013.01); *H01L 51/5024* (2013.01); *H01L 51/5064* (2013.01); *H01L 51/5072* (2013.01); *H01L 51/5092* (2013.01); *H01L 51/5096* (2013.01); *H01L 51/5221* (2013.01); *H01L 2251/301* (2013.01); *H01L 2251/308* (2013.01); *Y02E 10/549* (2013.01)

(58) Field of Classification Search
None
See application file for complete search history.

(56) References Cited

U.S. PATENT DOCUMENTS

| 2002/0064681 A1 | 5/2002 | Takiguchi et al. |
| 2003/0235712 A1 | 12/2003 | Takiguchi et al. |
| 2006/0220004 A1* | 10/2006 | Stossel .............. C07D 213/30 257/40 |
| 2007/0166566 A1* | 7/2007 | Royster, Jr. .......... C09K 11/06 428/690 |
| 2007/0249834 A1 | 10/2007 | Stossel et al. |
| 2008/0214818 A1* | 9/2008 | Chin .................. C07D 213/72 546/81 |
| 2009/0278444 A1 | 11/2009 | Forest et al. |
| 2011/0253988 A1* | 10/2011 | Molt ................... C07F 15/0033 257/40 |
| 2011/0284799 A1* | 11/2011 | Stoessel .................. C07F 1/00 252/301.16 |
| 2013/0112920 A1 | 5/2013 | Stoessel et al. |
| 2013/0112921 A1 | 5/2013 | Stoessel et al. |
| 2013/0253617 A1* | 9/2013 | Anemian ............ C07F 15/0033 607/88 |
| 2014/0231770 A1* | 8/2014 | Inoue .................. H01L 51/0085 257/40 |

FOREIGN PATENT DOCUMENTS

| DE | 102010027316 A1 | 1/2012 |
| DE | 102010027317 A1 | 1/2012 |
| JP | 2003007469 A | 1/2003 |
| JP | 2003146996 A | 5/2003 |
| JP | 2004131463 A | 4/2004 |
| JP | 2004131464 A | 4/2004 |
| JP | 2008500377 A | 1/2008 |
| JP | 2011119576 A | 6/2011 |
| JP | 2012516831 A | 7/2012 |
| TW | 2009/35970 A | 8/2009 |

OTHER PUBLICATIONS

Thummel et al., "Polyaza-Cavity Shaped Molecules. 14. Annelated 2-(2'-Pyridyl)indoles, 2,2'-Biindoles, and Related Systems", J. Org. Chem., 1989, vol. 54, pp. 1720-1725.
International Search Report for International Application No. PCT/EP2013/002726; International Filing Date Sep. 11, 2013.
Japanese Office Action for Japanese Application No. 2015-536002, dated Jun. 13, 2017, 6 pages.

* cited by examiner

*Primary Examiner* — Robert S Loewe
(74) *Attorney, Agent, or Firm* — RatnerPrestia

(57) ABSTRACT

The present invention relates to metal complexes and to electronic devices, in particular organic electroluminescent devices, comprising these metal complexes.

25 Claims, No Drawings

METAL COMPLEXES

RELATED APPLICATIONS

This application is a national stage application, filed pursuant to 35 U.S.C. §371, of PCT/EP2013/002726, filed Sep. 11, 2013, which claims the benefit of European Patent Application No. 12006990.1, filed Oct. 9, 2012, which is incorporated herein by reference in its entirety.

The present invention relates to metal complexes which are suitable for use as emitters in organic electroluminescent devices.

The structure of organic electroluminescent devices (OLEDs) in which organic semiconductors are employed as functional materials is described, for example, in U.S. Pat. Nos. 4,539,507, 5,151,629, EP 0676461 and WO 98/27136. The emitting materials employed here are increasingly organometallic complexes which exhibit phosphorescence instead of fluorescence (M. A. Baldo et al., Appl. Phys. Lett. 1999, 75, 4-6). For quantum-mechanical reasons, an up to four-fold increase in energy and power efficiency is possible using organometallic compounds as phosphorescent emitters. In general, there is still a need for improvement in OLEDs which exhibit triplet emission, in particular with respect to efficiency, operating voltage and lifetime. This applies, in particular, to OLEDs which emit in the relatively short-wave region, i.e. green and in particular blue.

In accordance with the prior art, iridium and platinum complexes, in particular, are employed as triplet emitters in phosphorescent OLEDs. Thus, for example, iridium complexes are known which contain imidazophenanthridine derivatives or diimidazoquinazoline derivatives as ligands (WO 2007/095118). These complexes may result in blue phosphorescence on use in organic electroluminescent devices, depending on the precise structure of the ligand. WO 2010/086089 and WO 2011/157339 disclose metal complexes which contain imidazoisoquinoline derivatives as ligands. Good advances in the development of blue triplet emitters have already been achieved using complexes of this type. However, further improvements are still desirable, in particular with respect to efficiency, operating voltage and lifetime.

The object of the present invention is therefore the provision of novel metal complexes which are suitable as emitters for use in OLEDs. In particular, the object is to provide emitters which, depending on the substitution, are also suitable for blue- or green-phosphorescent OLEDs, and which at the same time exhibit improved properties with respect to efficiency, operating voltage, lifetime, colour coordinates and/or colour purity, i.e. width of the emission band. A further object of the present invention is the development of phosphorescent emitters which can simultaneously serve as hole-transporting compounds in the emitting layer.

Surprisingly, it has been found that certain metal chelate complexes described in greater detail below achieve one or more of the above-mentioned objects and are very highly suitable for use in an organic electroluminescent device. The present invention therefore relates to these metal complexes and to organic electroluminescent devices which comprise these complexes.

The invention thus relates to a compound of the formula (1),

  formula (1)

which contains a moiety $M(L)_n$ of the formula (2) or formula (3):

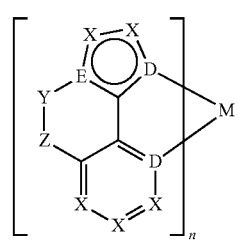  formula (2)

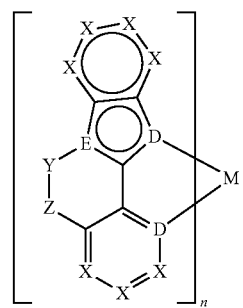  formula (3)

where the following applies to the symbols and indices used:

M is a transition metal;

X is selected on each occurrence, identically or differently, from the group consisting of CR and N;

Y is selected on each occurrence, identically or differently, from the group consisting of $C(R^1)_2$, $Si(R^1)_2$, $PR^1$, $P(=O)R^1$ or $BR^1$;

Z is selected on each occurrence, identically or differently, from the group consisting of $NR^1$, O or $C(R^1)_2$;

D is on each occurrence, identically or differently, C or N, with the proviso that at least one D stands for N;

E is on each occurrence, identically or differently, C or N, with the proviso that at least one of the groups E or D in the five-membered ring stands for N;

R, $R^1$ is on each occurrence, identically or differently, H, D, F, Cl, Br, I, $N(R^2)_2$, CN, $NO_2$, OH, COOH, $C(=O)N(R^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^2$, where one or more non-adjacent $CH_2$ groups may be replaced by $R^2C=CR^2$, $C\equiv C$, $Si(R^2)_2$, $C=O$, $NR^2$, O, S or $CONR^2$ and where one or more H atoms may be replaced by D, F, Cl, Br, I or CN, or an aromatic or hetero-aromatic ring system having 5 to 60 aromatic ring atoms, which may in each case be substituted by one or more radicals $R^2$, or an aryloxy or heteroaryloxy group having 5 to 40 aromatic ring atoms, which may be substituted by one or more radicals $R^2$, or an aralkyl or heteroaralkyl group having 5 to 40 aromatic ring atoms, which may be substituted by one or more radicals $R^2$, or a diarylamino group, diheteroarylamino group or arylheteroarylamino group having 10 to 40 aromatic ring atoms, which may be substituted by one or more radicals $R^2$; two adjacent radicals R or two adjacent radicals $R^1$ or R with $R^1$ here may also form a mono- or polycyclic, aliphatic, aromatic or heteroaromatic ring system with one another;

$R^2$ is on each occurrence, identically or differently, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which may be substituted by one or more radicals $R^3$, where one or more non-adjacent $CH_2$ groups may be replaced by $R^3C=CR^3$, $C≡C$, $Si(R^3)_2$, $C=O$, $NR^3$, O, S or $CONR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, or an aryloxy or heteroaryloxy group having 5 to 40 aromatic ring atoms, which may be substituted by one or more radicals $R^3$, or an aralkyl or heteroaralkyl group having 5 to 40 aromatic ring atoms, which may be substituted by one or more radicals $R^3$, or a diarylamino group, diheteroarylamino group or aryl-heteroarylamino group having 10 to 40 aromatic ring atoms, which may be substituted by one or more radicals $R^3$; two or more adjacent radicals $R^2$ with one another or $R^2$ with R or with $R^1$ here may form a mono- or polycyclic, aliphatic, aromatic or heteroaromatic ring system;

$R^3$ is on each occurrence, identically or differently, H, D, F or an aliphatic, aromatic and/or heteroaromatic hydrocarbon radical having 1 to 20 C atoms, in which, in addition, one or more H atoms may be replaced by F; two or more substituents $R^3$ here may also form a mono- or polycyclic, aliphatic ring system with one another;

L' is, identically or differently on each occurrence, any desired co-ligand;

n is 1, 2 or 3;

m is 0, 1, 2, 3 or 4;

a plurality of ligands L with one another or L with L' here may also be linked via a single bond or a divalent or trivalent bridge and thus form a tridentate, tetradentate, pentadentate or hexadentate ligand system, where in this case L' is not a separate co-ligand, but instead a coordinating group;

furthermore a substituent R may also additionally be coordinated to the metal.

The circles in the structure of the formula (2) and (3) here indicate an aromatic or heteroaromatic system, as usual in organic chemistry. Although two circles are drawn in for simplification in the structure of the formula (3), this nevertheless means that it is a single heteroaromatic system.

"Adjacent radicals" in the definition of the radicals here means that these radicals are bonded to the same atom or to atoms which are bonded directly to one another or, if they are not bonded to atoms which are bonded directly, that this is the next-possible position in which a substituent can be bonded. This is explained again in the following diagrammatic representation with reference to two specific ligands:

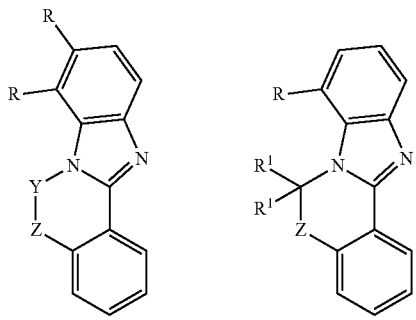

adjacent radicals R on C atoms bonded directly to one another adjacent radicals R and $R^1$ in next-possible position In the complexes of the formula (1), the indices n and m are selected so that the coordination number on the metal M in total, depending on the metal, corresponds to the coordination number which is usual for this metal. For transition metals, this is usually the coordination number 4, 5 or 6, depending on the metal. It is generally known that metal coordination compounds have different coordination numbers, i.e. bind a different number of ligands, depending on the metal and on the oxidation state of the metal. Since the preferred coordination numbers of metals or metal ions in various oxidation states belong to the general expert knowledge of the person skilled in the art in the area of organometallic chemistry or coordination chemistry, it is straightforward for the person skilled in the art to use a suitable number of ligands, depending on the metal and its oxidation state and depending on the precise structure of the ligand L, and thus to select the indices n and m suitably.

An aryl group in the sense of this invention contains 6 to 40 C atoms; a heteroaryl group in the sense of this invention contains 2 to 40 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed aryl or heteroaryl group, for example naphthalene, anthracene, phenanthrene, quinoline, isoquinoline, etc.

An aromatic ring system in the sense of this invention contains 6 to 60 C atoms in the ring system. A heteroaromatic ring system in the sense of this invention contains 1 to 60 C atoms and at least one heteroatom in the ring system, with the proviso that the sum of C atoms and heteroatoms is at least 5. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be interrupted by a non-aromatic unit (preferably less than 10% of the atoms other than H), such as, for example, a C, N or O atom or a carbonyl group. Thus, for example, systems such as 9,9'-spirobifluorene, 9,9-diarylfluorene, triarylamine, diaryl ether, stilbene, etc., are also intended to be taken to be aromatic ring systems in the sense of this invention, as are systems in which two or more aryl groups are interrupted, for example, by a linear or cyclic alkyl group or by a silyl group. Furthermore, systems in which two or more aryl or heteroaryl groups are bonded directly to one another, such as, for example, biphenyl or terphenyl, are likewise intended to be taken to be an aromatic or heteroaromatic ring system.

A cyclic alkyl, alkoxy or thioalkoxy group in the sense of this invention is taken to mean a monocyclic, bicyclic or polycyclic group.

For the purposes of the present invention, a $C_1$- to $C_{40}$-alkyl group, in which, in addition, individual H atoms or $CH_2$ groups may be substituted by the above-mentioned groups, is taken to mean, for example, the radicals methyl, ethyl, n-propyl, i-propyl, cyclopropyl, n-butyl, i-butyl, s-butyl, t-butyl, cyclobutyl, 2-methylbutyl, n-pentyl, s-pentyl, tert-pentyl, 2-pentyl, neo-pentyl, cyclopentyl, n-hexyl, s-hexyl, tert-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octa-dec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclo-hex-1-yl, 1-(n-butyl)cyclohex-1-yl, 1-(n-hexyl)cyclohex-1-yl, 1-(n-octyl)cy-clo-hex-1-yl and 1-(n-decyl)cyclohex-1-yl. An alkenyl group is taken to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is taken to mean, for example, ethynyl, propynyl, butynyl, pentynyl, hexynyl, heptynyl or octynyl. A $C_1$- to $C_{40}$-alkoxy group is taken to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system having 5-60 aromatic ring atoms, which may also in each case be substituted by the radicals R mentioned above and which may be linked to the aromatic or heteroaromatic ring system via any desired positions, is taken to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

Preference is given to compounds of the formula (1), characterised in that they are uncharged, i.e. are electrically neutral. This is achieved in a simple manner by selecting the charges of the ligands L and L' in such a way that they compensate for the charge of the complexed metal atom M. If the compound of the formula (1) is not neutral, it also contains one or more counterions, i.e. anions if it is cationic or cations if it is anionic.

Preference is furthermore given to compounds of the formula (1), characterised in that the sum of the valence electrons around the metal atom is 16 in tetracoordinated complexes and 16 or 18 in pentacoordinated complexes and 18 in hexacoordinated complexes. This preference is due to the particular stability of these metal complexes.

In a preferred embodiment of the invention, M stands for a transition metal, where lanthanides and actinides are excluded, in particular for a tetracoordinated, pentacoordinated or hexacoordinated transition metal, particularly preferably selected from the group consisting of chromium, molybdenum, tungsten, rhenium, ruthenium, osmium, rhodium, iridium, nickel, palladium, platinum, copper, silver and gold, in particular molybdenum, tungsten, rhenium, ruthenium, osmium, iridium, copper, platinum and gold. Very particular preference is given to iridium, platinum and copper. The metals here can be in various oxidation states. The above-mentioned metals are preferably in the oxidation states Cr(0), Cr(II), Cr(III), Cr(IV), Cr(VI), Mo(0), Mo(II), Mo(III), Mo(IV), Mo(VI), W(0), W(II), W(III), W(IV), W(VI), Re(I), Re(II), Re(III), Re(IV), Ru(II), Ru(III), Os(II), Os(III), Os(IV), Rh(I), Rh(III), Ir(I), Ir(III), Ir(IV), Ni(0), Ni(II), Ni(IV), Pd(II), Pt(II), Pt(IV), Cu(I), Cu(II), Cu(III), Ag(I), Ag(II), Au(I), Au(III) and Au(V). Particular preference is given to Mo(0), W(0), Re(I), Ru(II), Os(II), Rh(III), Cu(I), Ir(III) and Pt(II). Very particular preference is given to Ir(III), Pt(II) and Cu(I), in particular Ir(III).

In a preferred embodiment of the invention, M is a tetracoordinated metal, and the index n stands for 1 or 2. If the index n=1, one bidentate or two monodentate ligands L', preferably one bidentate ligand L', are also coordinated to the metal M. If the index n=2, the index m=0. Preferred tetracoordinated metals are Pt(II) and Cu(I). If M stands for Cu(I), both groups D preferably stand for N. If M stands for Pt(II), either both groups D stand for N or one group D stands for N and the other group D stands for C, preferably one group D stands for N and the other group D stands for C.

In a further preferred embodiment of the invention, M is a hexacoordinated metal, and the index n stands for 1, 2 or 3, preferably for 2 or 3. If the index n=1, four monodentate or two bidentate or one bidentate and two monodentate or one tridentate and one monodentate or one tetradentate ligand L', preferably two bidentate ligands L', are also coordinated to the metal. If the index n=2, one bidentate or two monodentate ligands L', preferably one bidentate ligand L', are also coordinated to the metal. If the index n=3, the index m=0. A preferred hexacoordinated metal is Ir(III). If M stands for Ir(III), either both groups D stand for N or one group D stands for N and the other group D stands for C, preferably one group D stands for N and the other group D stands for C.

In a preferred embodiment of the invention, E stands for N and either the D in the five-membered ring or the D in the six-membered ring stands N, while the other D stands for C. In a further embodiment of the invention, E stands for C and the two groups D stand for N. The ligands L are thus preferably monoanionic ligands.

Preferred moieties of the formula (2) are thus the moieties of the following formulae (2a), (2b) and (2c), and preferred moieties of the formula (3) are the moieties of the following formulae (3a), (3b) and (3c), formula (2a)

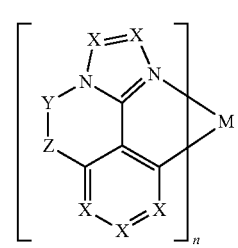

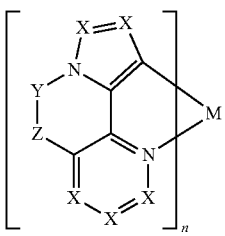
formula (2b)

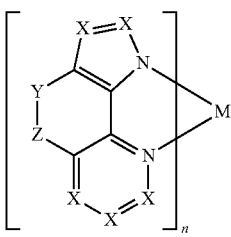
formula (2c)

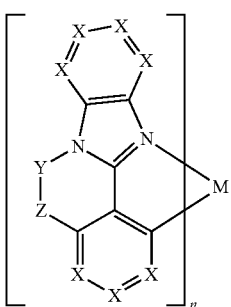
formula (3a)

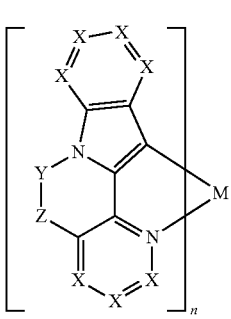
formula (3b)

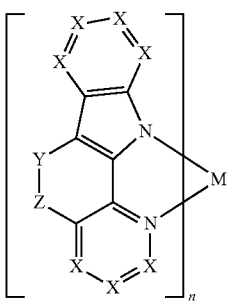
formula (3c)

where the symbols and indices used have the meanings given above.

In a further preferred embodiment of the invention, the group —Y—Z— stands, identically or differently on each occurrence, for —C(R¹)₂—NR¹—, —C(R¹)₂—O—, —C(R¹)₂—C(R¹)₂—, —Si(R¹)₂—NR¹—, —Si(R¹)₂—O—, —Si(R¹)₂—C(R¹)₂—, —PR¹—NR¹—, —PR¹—O—, —PR¹—C(R¹)₂—, —P(=O)R¹—NR¹—, —P(=O)R¹—O—, —P(=O)R¹—C(R¹)₂—, —BR¹—NR¹—, —BR¹—O— or —BR¹—C(R¹)₂—. The group —Y—Z— particularly preferably stands, identically or differently on each occurrence, for —C(R¹)₂—NR¹—, —C(R¹)₂—O—, —Si(R¹)₂—NR¹— or —Si(R¹)₂—O—.

In a preferred embodiment of the invention, the group —Y—Z— contains no benzylic protons. If Y stands for C(R¹)₂, R¹ is preferably selected, identically or differently on each occurrence, from the group consisting of F, CN, a straight-chain alkyl group having 1 to 10 C atoms or a branched or cyclic alkyl group having 3 to 10 C atoms, each of which may be substituted by one or more radicals R², where one or more non-adjacent CH₂ groups may be replaced by R²C=CR² and where one or more H atoms may be replaced by F, or an aromatic or heteroaromatic ring system having 5 to 30 aromatic ring atoms, which may in each case be substituted by one or more radicals R², or an aryloxy or heteroaryloxy group having 5 to 30 aromatic ring atoms, which may be substituted by one or more radicals R², or an aralkyl or heteroaralkyl group having 5 to 40 aromatic ring atoms, which may be substituted by one or more radicals R², or a diarylamino group, diheteroarylamino group or arylheteroarylamino group having 10 to 30 aromatic ring atoms, which may be substituted by one or more radicals R²; two adjacent radicals R or two adjacent radicals R¹ or R with R¹ here may also form a mono- or polycyclic, aliphatic, aromatic or heteroaromatic ring system with one another.

In the ligand L, preferably no, one or two groups X, particularly preferably no or one group X, stand for N.

Preferred embodiments of the moieties of the formula (2) are the moieties of the following formulae (2-A) to (2-G),

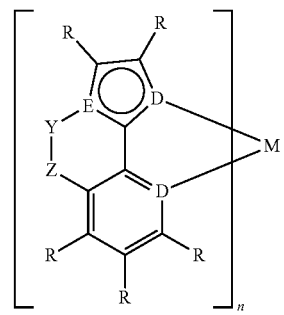
formula (2-A)

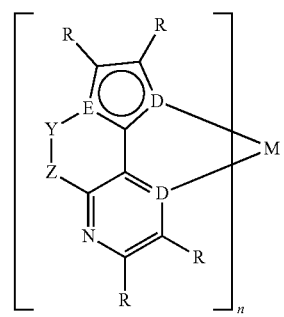
formula (2-B)

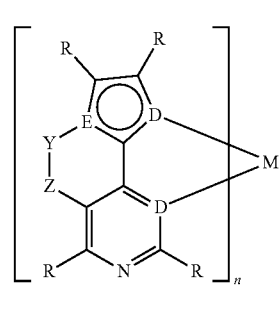
formula (2-C)

-continued
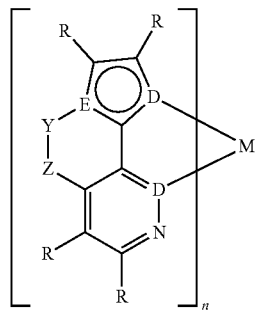
formula (2-D)
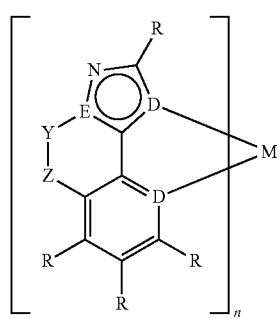
formula (2-E)
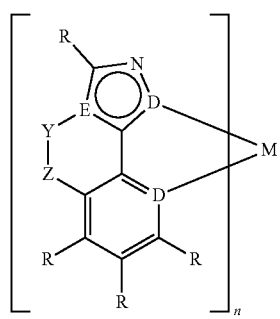
formula (2-F)
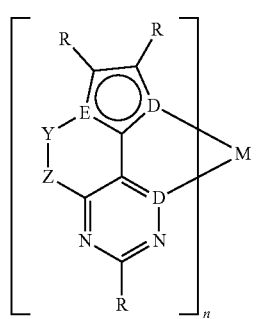
formula (2-G)
where the symbols and indices used have the meanings given above.
Preferred embodiments of the moieties of the formula (3) are the moieties of the following formulae (3-A) to (3-H),
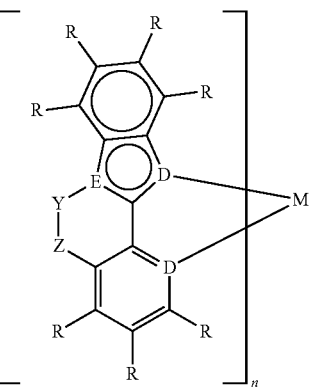
formula (3-A)
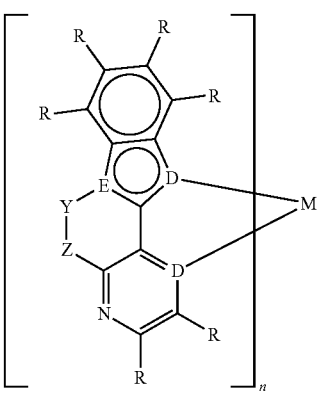
formula (3-B)
formula (3-C)
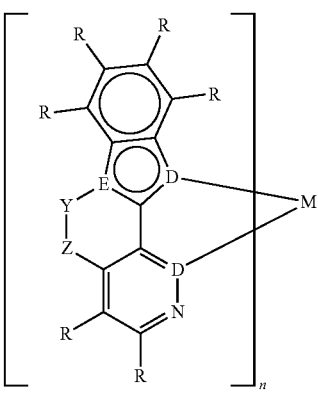
formula (3-D)

formula (3-E)

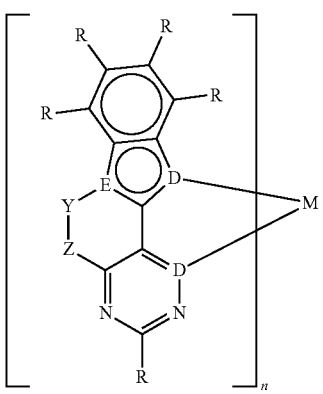

formula (3-F)

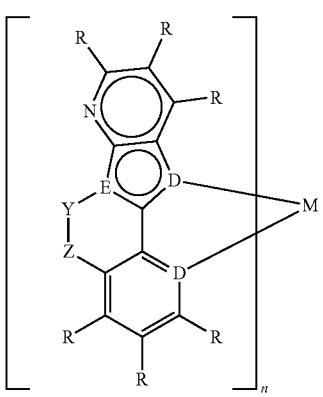

formula (3-G)

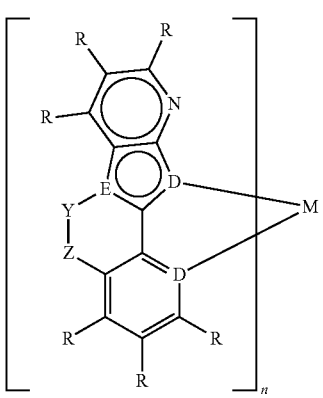

formula (3-H)

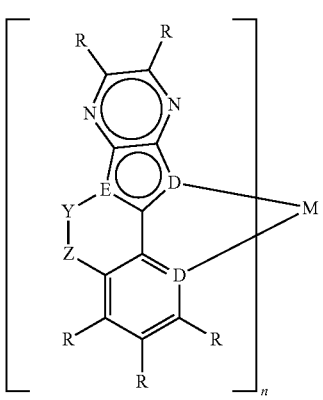

where the symbols and indices used have the meanings given above.

It is particularly preferred if the group E in the moieties of the formulae (2-A) to (2-G) and (3-A) to (3-H) stands for N and either the group D in the five-membered ring or the group D in the six-membered ring stands for N, while the other group D stands for C, or if the group E stands for C and the two groups D stand for N, analogously to the general formulae (2a) to (2c) and (3a) to (3c) shown above.

These compounds furthermore preferably contain the groups —Y—Z— mentioned as preferred above.

If one or more groups X in the moieties of the formula (2) or (3) stand for nitrogen, it is preferred if a group R which is not equal to hydrogen or deuterium is bonded as substituent adjacent to this nitrogen atom. This R is preferably a group selected from $CF_3$, $OCF_3$, alkyl or alkoxy groups having 1 to 10 C atoms, in particular branched or cyclic alkyl or alkoxy groups having 3 to 10 C atoms, aromatic or heteroaromatic ring systems or aralkyl or heteroaralkyl groups, where the groups may each optionally be substituted by one or more radicals $R^2$. These groups are bulky groups. Furthermore preferably, this radical R may also form a condensed-on ring with an adjacent radical R.

If the radical R which is adjacent to a nitrogen atom stands for an alkyl group, this alkyl group then preferably has 3 to 10 C atoms. It is furthermore preferably a secondary or tertiary alkyl group in which the secondary or tertiary C atom is either bonded directly to the ligand or is bonded to the ligand via a $CH_2$ group. This alkyl group is particularly preferably selected from the structures of the following formulae (R-1) to (R-33), where the linking of these groups to the ligand is in each case also drawn in:

(R-1)

(R-2)

(R-3)

(R-4)

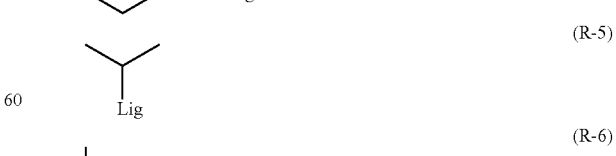

(R-5)

(R-6)

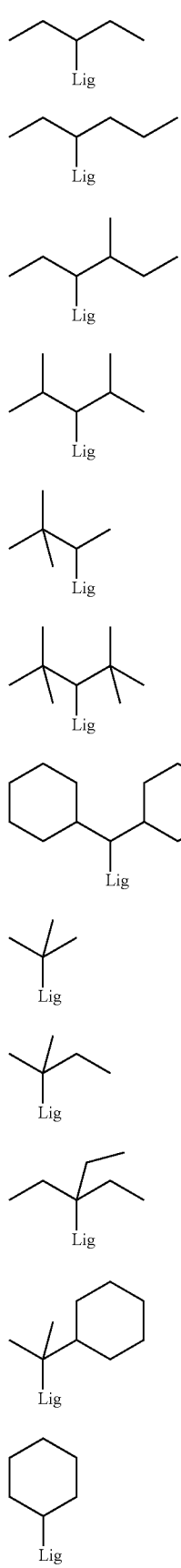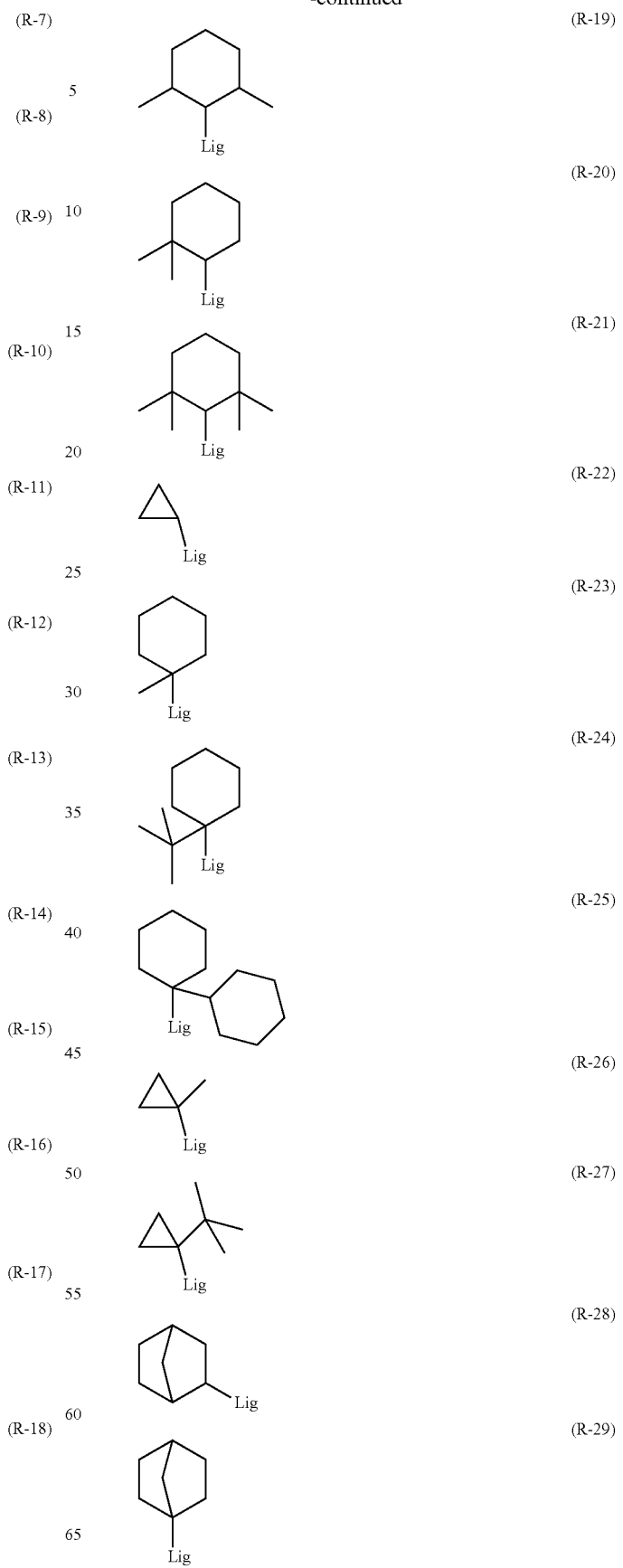

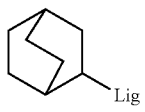 (R-30)

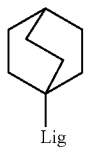 (R-31)

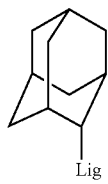 (R-32)

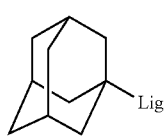 (R-33)

where Lig denotes the linking of the alkyl group to the ligand.

If the radical R which is adjacent to a nitrogen atom stands for an alkoxy group, this alkoxy group then preferably has 3 to 10 C atoms. This alkoxy group is preferably selected from the structures of the following formulae (R-34) to (R-47), where the linking of these groups to the ligand is in each case also drawn in:

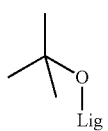 (R-34)

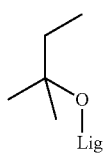 (R-35)

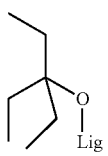 (R-36)

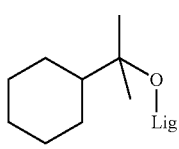 (R-37)

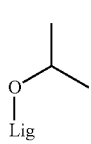 (R-38)

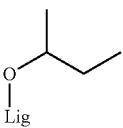 (R-39)

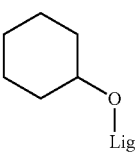 (R-40)

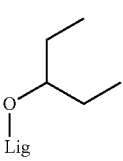 ($R^1$-41)

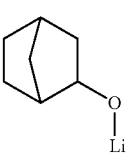 ($R^1$-42)

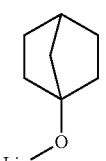 ($R^1$-43)

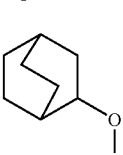 ($R^1$-44)

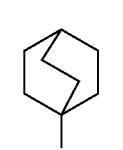 ($R^1$-45)

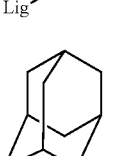 ($R^1$-46)

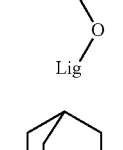 ($R^1$-47)

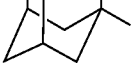

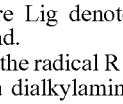

where Lig denotes the linking of the alkyl group to the ligand.

If the radical R which is adjacent to a nitrogen atom stands for a dialkylamino group, each of these alkyl groups then preferably has 1 to 8 C atoms, particularly preferably 1 to 6

C atoms. Examples of suitable alkyl groups are methyl, ethyl or the structures shown above as groups (R-1) to (R-33). The dialkylamino group is particularly preferably selected from the structures of the following formulae (R-48) to (R-55), where the linking of these groups to the ligand is in each case also drawn in:

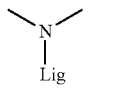 (R-48)

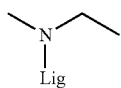 (R-49)

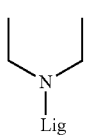 (R-50)

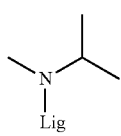 (R-51)

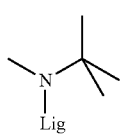 (R-52)

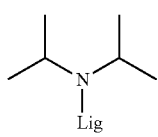 (R-53)

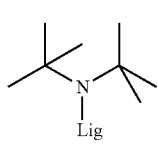 (R-54)

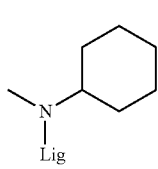 (R-55)

where Lig denotes the linking of the alkyl group to the ligand.

If the radical R which is adjacent to a nitrogen atom stands for an aralkyl group, this aralkyl group is then preferably selected from the structures of the following formulae (R-56) to (R-69), where the linking of these groups to the ligand is in each case also drawn in:

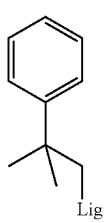 (R-56)

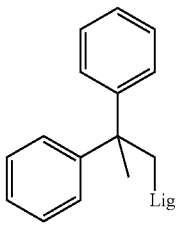 (R-57)

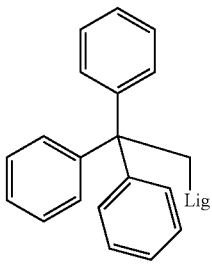 (R-58)

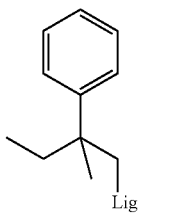 (R-59)

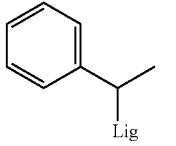 (R-60)

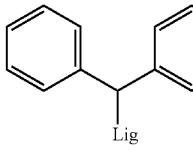 (R-61)

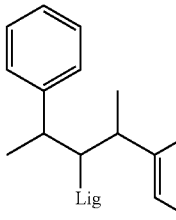 (R-62)

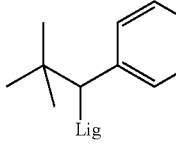 (R-63)

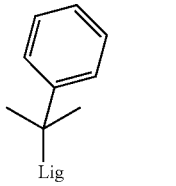 (R-64)

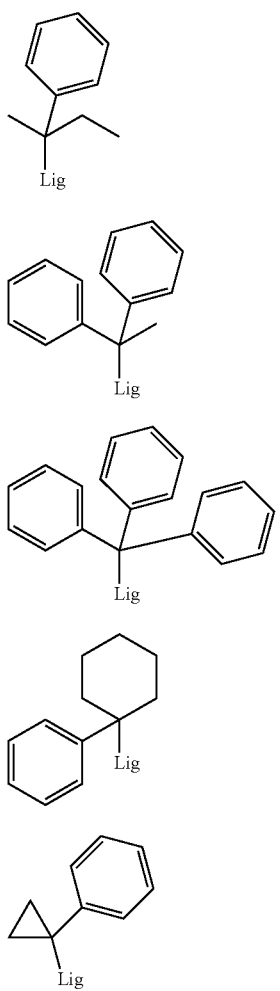

(R-65)

(R-66)

(R-67)

(R-68)

(R-69)

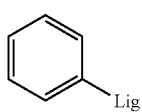

(R-70)

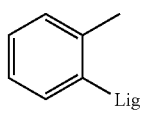

(R-71)

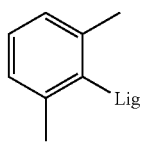

(R-72)

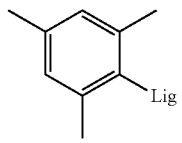

(R-73)

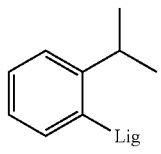

(R-74)

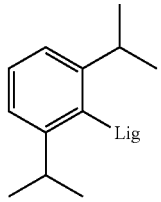

(R-75)

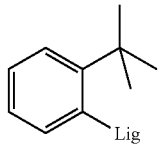

(R-76)

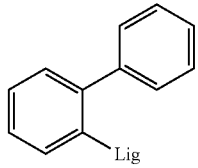

(R-77)

(R-78)

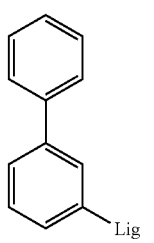

(R-79)

where Lig denotes the linking of the aralkyl group to the ligand, and the phenyl groups may each be substituted by one or more radicals $R^2$.

If the radical R which is adjacent to a nitrogen atom stands for an aromatic or heteroaromatic ring system, this aromatic or heteroaromatic ring system then preferably has 5 to 30 aromatic ring atoms, particularly preferably 5 to 24 aromatic ring atoms. This aromatic or heteroaromatic ring system furthermore preferably contains no aryl or heteroaryl groups in which more than two aromatic six-membered rings are condensed directly onto one another. The aromatic or heteroaromatic ring system particularly preferably contains no condensed aryl or heteroaryl groups at all, and it very particularly preferably contains only phenyl groups. The aromatic ring system here is preferably selected from the structures of the following formulae (R-70) to (R-86), where the linking of these groups to the ligand is in each case also drawn in:

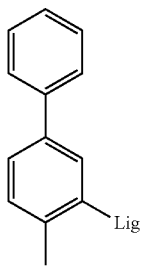 (R-80)

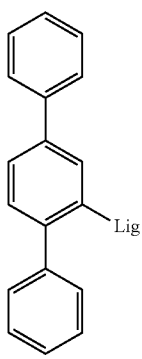 (R-81)

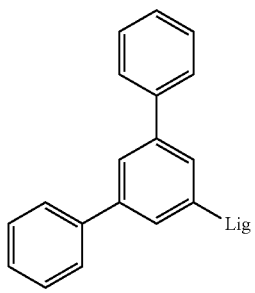 (R-82)

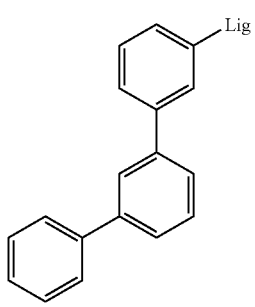 (R-83)

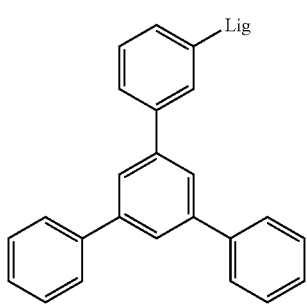 (R-84)

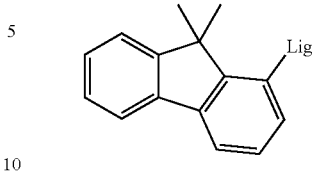 (R-85)

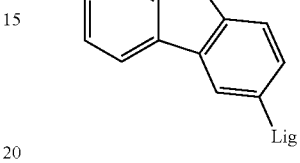 (R-86)

where Lig denotes the linking of the aromatic or heteroaromatic ring system to the ligand, and the phenyl groups may each be substituted by one or more radicals $R^2$.

The heteroaromatic ring system is furthermore preferably selected from the structures of the following formulae (R-87) to (R-112), where the linking of these groups to the ligand is in each case also drawn in:

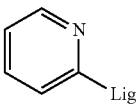 (R-87)

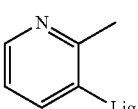 (R-88)

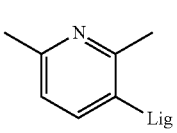 (R-89)

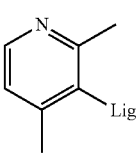 (R-90)

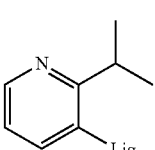 (R-91)

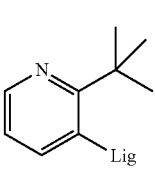 (R-92)

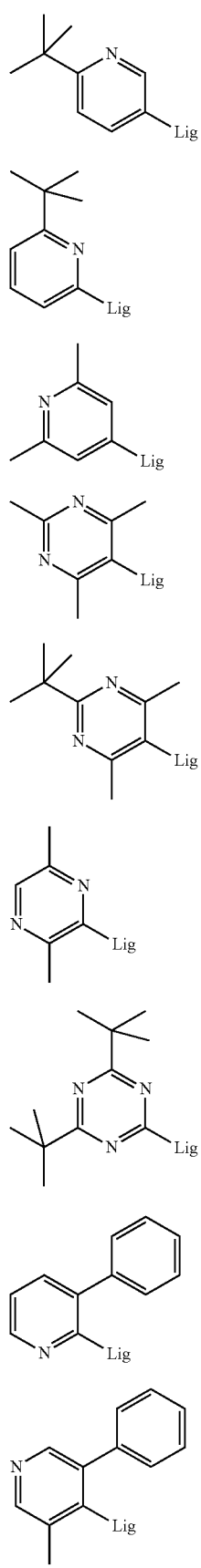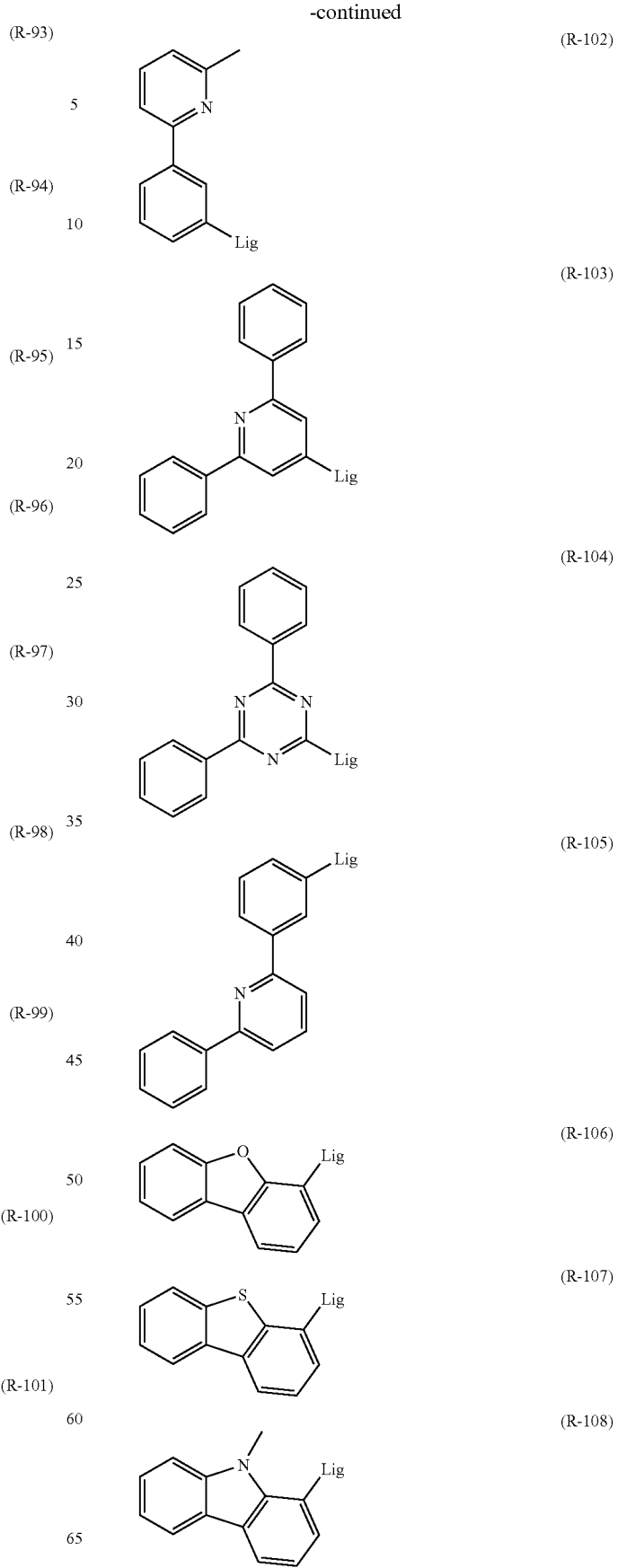

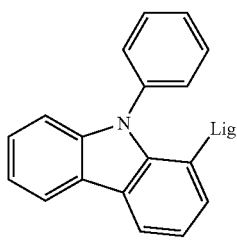
(R-109)

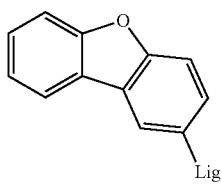
(R-110)

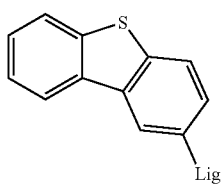
(R-111)

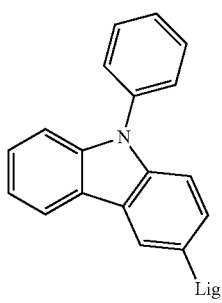
(R-112)

where Lig denotes the linking of the aromatic or heteroaromatic ring system to the ligand, and the aromatic and heteroaromatic groups may each be substituted by one or more radicals $R^2$.

It may furthermore be preferred if two adjacent groups X stand for CR and the respective radicals R, together with the C atoms, form a ring of the following formula (4) or formula (5),

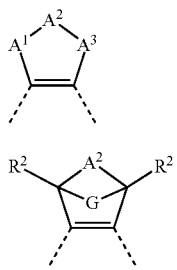

formula (4)

formula (5)

where $R^2$ and $R^3$ have the meanings given above, the dashed bonds indicate the linking of the two carbon atoms in the ligand and furthermore:
$A^1$, $A^3$ is, identically or differently on each occurrence, $C(R^4)_2$, O, S, $NR^4$ or $C(=O)$;
$A^2$ is $C(R^2)_2$, O, S, $NR^4$ or $C(=O)$;
G is an alkylene group having 1, 2 or 3 C atoms, which may be substituted by one or more radicals $R^3$, or is —$CR^3$=$CR^3$— or an ortho-linked arylene or heteroarylene group having 5 to 14 aromatic ring atoms, which may be substituted by one or more radicals $R^3$;
$R^4$ is, identically or differently on each occurrence, F, a straight-chain alkyl or alkoxy group having 1 to 20 C atoms, a branched or cyclic alkyl or alkoxy group having 3 to 20 C atoms, each of which may be substituted by one or more radicals $R^3$, where one or more non-adjacent $CH_2$ groups may be replaced by $R^3C=CR^3$, C≡C, $Si(R^3)_2$, C=O, $NR^3$, O, S or $CONR^3$ and where one or more H atoms may be replaced by D or F, or an aromatic or heteroaromatic ring system having 5 to 24 aromatic ring atoms, which may in each case be substituted by one or more radicals $R^3$, or an aryloxy or heteroaryloxy group having 5 to 24 aromatic ring atoms, which may be substituted by one or more radicals $R^3$, or an aralkyl or heteroaralkyl group having 5 to 24 aromatic ring atoms, which may be substituted by one or more radicals $R^3$; two radicals $R^4$ which are bonded to the same carbon atom may form an aliphatic or aromatic ring system with one another here and thus form a Spiro system; furthermore, $R^4$ may form an aliphatic ring system with an adjacent radical R, $R^1$ or $R^2$;
with the proviso that no two heteroatoms in $A^1$-$A^2$-$A^3$ are bonded directly to one another.

It is essential in the case of the groups of the formulae (4) and (5) that they contain no acidic benzylic protons. Benzylic protons are taken to mean protons which are bonded to a carbon atom which are bonded directly to the heteroaromatic ligand. The absence of acidic benzylic protons is achieved in formula (4) through $A^1$ and $A^3$, if they stand for $C(R^4)_2$, being defined in such a way that $R^4$ is not equal to hydrogen. The absence of acidic benzylic protons is automatically achieved in formula (5) through it being a bicyclic structure. Owing to the rigid spatial arrangement, $R^2$, if it stands for H, is significantly less acidic than benzylic protons, since the corresponding anion of the bicyclic structure is not mesomerism-stabilised. Even if $R^2$ in formula (5) stands for H, it is a non-acidic proton in the sense of the present application.

Preference is furthermore given to a condensed-on aliphatic six-membered ring or seven-membered ring, which preferably contains no benzylic protons.

In a preferred embodiment of the structure of the formula (4), a maximum of one of the groups $A^1$, $A^2$ and $A^3$ stands for a heteroatom, in particular for O or $NR^4$, and the other two groups stand for $C(R^4)_2$ or $C(R^2)_2$ or $A^1$ and $A^3$ stand, identically or differently on each occurrence, for O or $NR^4$ and $A^2$ stands for $C(R^2)_2$. In a particularly preferred embodiment of the invention, $A^1$ and $A^3$ stand, identically or differently on each occurrence, for $C(R^4)_2$ and $A^2$ stands for $C(R^2)_2$ and particularly preferably for $C(R^4)_2$.

In a preferred embodiment of the structure of the formula (5), the radicals $R^2$ which are bonded to the bridgehead stand for H, D, F or $CH_3$. $A^2$ furthermore preferably stands for $C(R^2)_2$ or O, and particularly preferably for $C(R^4)_2$. The group G in formula (5) furthermore preferably stands for an ethylene group, which may be substituted by one or more radicals $R^3$, where $R^3$ preferably stands, identically or differently on each occurrence, for H or an alkyl group having 1 to 4 C atoms, or an ortho-arylene group having 6 to 10 C atoms, which may be substituted by one or more radicals $R^3$, but is preferably unsubstituted, in particular an ortho-phenylene group, which may be substituted by one or more radicals $R^3$, but is preferably unsubstituted.

In a further preferred embodiment of the invention, $R^4$ in the groups of the formula (4) and (5) and in the preferred embodiments stands, identically or differently on each occurrence, for F, a straight-chain alkyl group having 1 to 10 C atoms or a branched or cyclic alkyl group having 3 to 20 C atoms, where in each case one or more non-adjacent CH$_2$ groups may be replaced by $R^3C$=$CR^3$ and one or more H atoms may be replaced by D or F, or an aromatic or heteroaromatic ring system having 5 to 14 aromatic ring atoms, which may in each case be substituted by one or more radicals $R^3$; two radicals $R^4$ which are bonded to the same carbon atom may form an aliphatic or aromatic ring system with one another here and may thus form a spiro system.

In a particularly preferred embodiment of the invention, $R^4$ in the groups of the formulae (4) and (5) and in the preferred embodiments stands, identically or differently on each occurrence, for F, a straight-chain alkyl group having 1 to 3 C atoms, in particular methyl, or an aromatic or heteroaromatic ring system having 5 to 12 aromatic ring atoms, which may in each case be substituted by one or more radicals $R^3$, but is preferably unsubstituted; two radicals $R^4$ which are bonded to the same carbon atom here may form an aliphatic or aromatic ring system with one another and thus form a spiro system.

Examples of particularly suitable groups of the formula (4) are the groups (4-1) to (4-69) shown below:

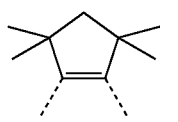 (4-1)

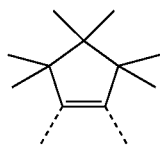 (4-2)

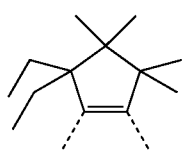 (4-3)

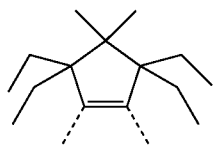 (4-4)

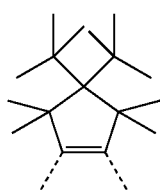 (4-5)

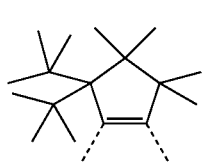 (4-6)

-continued

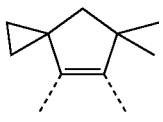 (4-7)

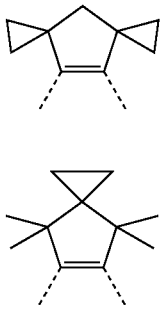 (4-8)

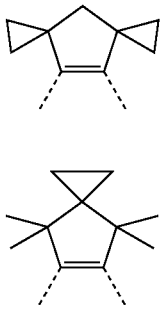 (4-9)

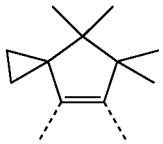 (4-10)

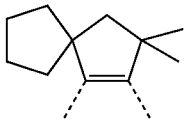 (4-11)

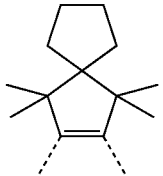 (4-12)

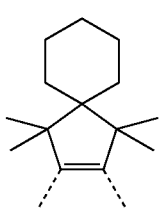 (4-13)

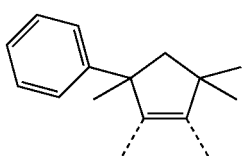 (4-14)

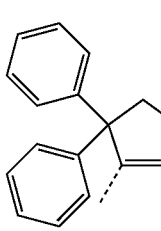 (4-15)

(4-16) 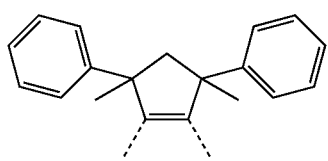
(4-17) 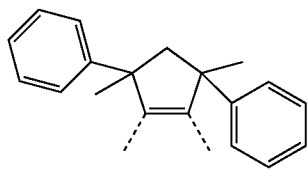
(4-18) 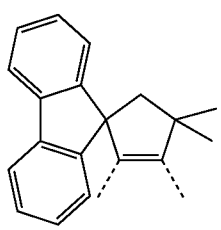
(4-19) 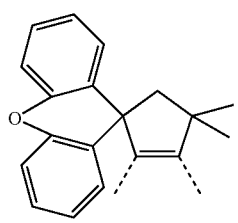
(4-20) 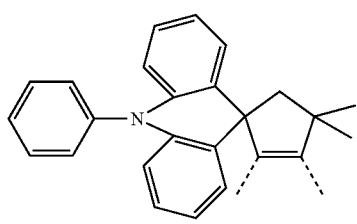
(4-21) 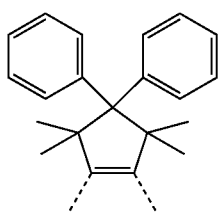
(4-22) 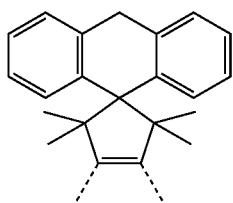
(4-23) 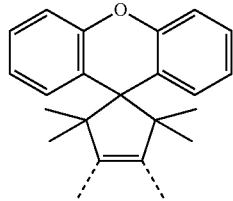
(4-24) 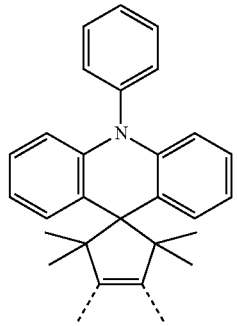
(4-25) 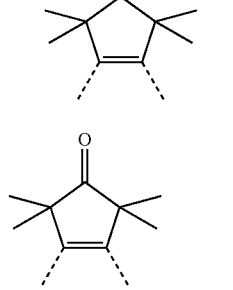
(4-26) 
(4-27) 
(4-28) 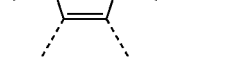
(4-29) 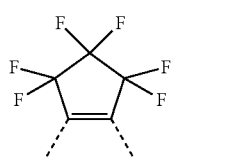
(4-30) 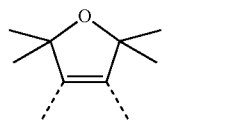
(4-31) 

(4-32) 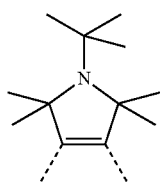
(4-33) 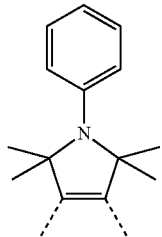
(4-34) 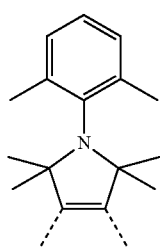
(4-35) 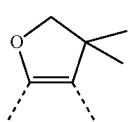
(4-36) 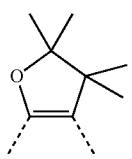
(4-37) 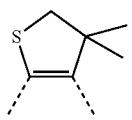
(4-38) 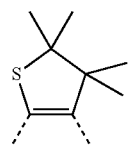
(4-39) 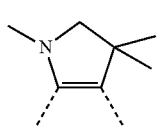
(4-40) 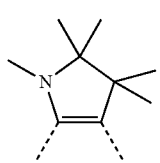
(4-41) 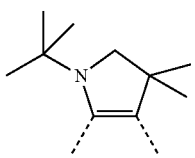
(4-42) 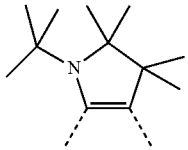
(4-43) 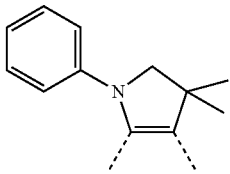
(4-44) 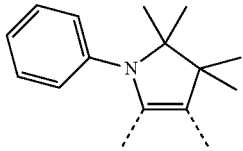
(4-45) 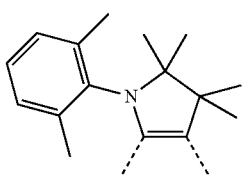
(4-46) 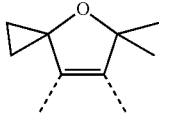
(4-47) 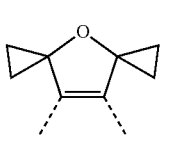
(4-48) 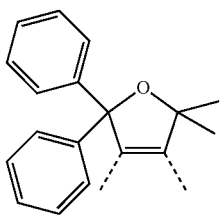
(4-49) 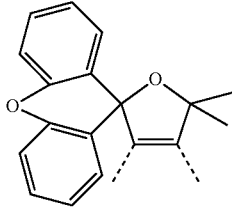

(4-50) 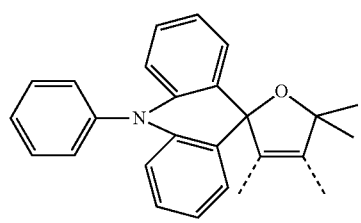
(4-51) 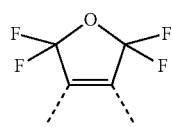
(4-52) 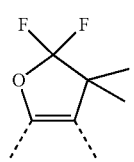
(4-53) 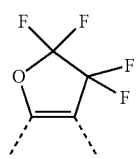
(4-54) 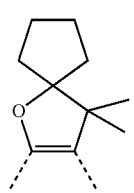
(4-55) 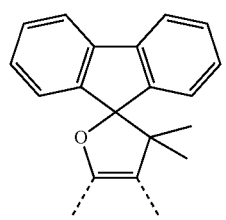
(4-56) 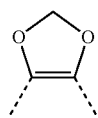
(4-57) 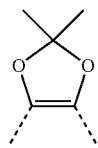
(4-58) 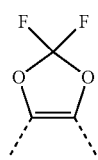
(4-59) 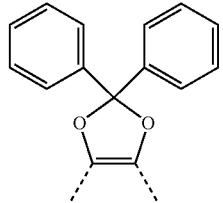
(4-60) 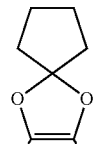
(4-61) 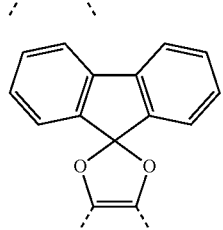
(4-62) 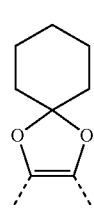
(4-63) 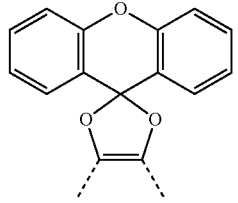
(4-64) 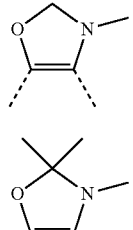
(4-65) 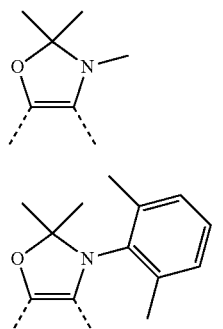
(4-66) 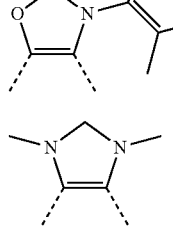
(4-67) 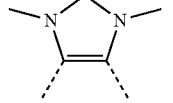

(4-68)
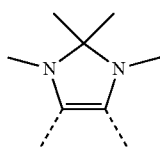
(4-69)
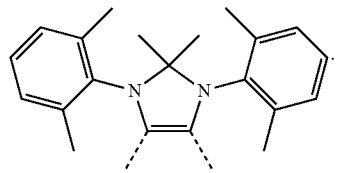
Examples of particularly suitable groups of the formula (5) are the groups (5-1) to (5-21) shown below:
(5-1)
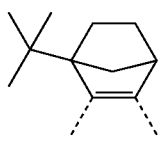
(5-2)
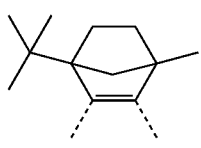
(5-3)
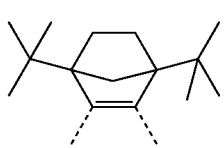
(5-4)
(5-5)
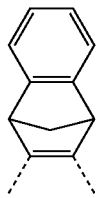
(5-6)
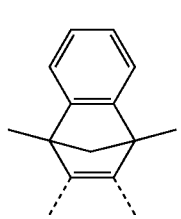
(5-7)
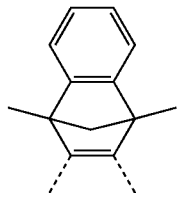
(5-8)
(5-9)
(5-10)
(5-11)
(5-12)
(5-13)
(5-14)
(5-15)
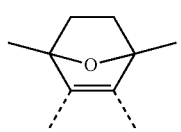
(5-16)
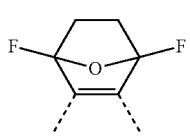
(5-17)
(5-18)
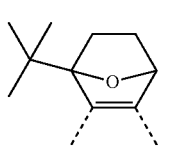

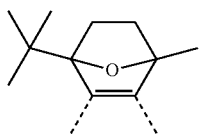 (5-19)

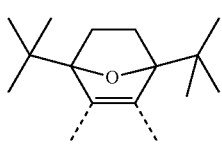 (5-20)

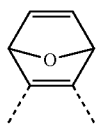 (5-21)

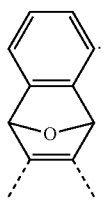 (5-22)

If further or other radicals R are bonded in the moiety of the formula (2) or (3), these radicals R are preferably selected on each occurrence, identically or differently, from the group consisting of H, D, F, Br, I, $N(R^2)_2$, CN, $Si(R^2)_3$, $B(OR^2)_2$, $C(=O)R^2$, a straight-chain alkyl group having 1 to 10 C atoms or an alkenyl group having 2 to 10 C atoms or a branched or cyclic alkyl group having 3 to 10 C atoms, each of which may be substituted by one or more radicals $R^2$, where one or more H atoms may be replaced by D or F, or an aromatic or heteroaromatic ring system having 5 to 30 aromatic ring atoms, which may in each case be substituted by one or more radicals $R^2$; two adjacent radical R or R with $R^2$ here may also form a mono- or polycyclic, aliphatic or aromatic ring system with one another. These radicals R are particularly preferably selected on each occurrence, identically or differently, from the group consisting of H, D, F, CN, a straight-chain alkyl group having 1 to 6 C atoms or a branched or cyclic alkyl group having 3 to 10 C atoms, where one or more H atoms may be replaced by D or F, or an aromatic or heteroaromatic, in particular an aromatic ring system having 5 to 24 aromatic ring atoms, which may in each case be substituted by one or more radicals $R^2$; two adjacent radicals R or R with $R^2$ here may also form a mono- or polycyclic, aliphatic or aromatic ring system with one another.

It is furthermore possible for the substituent R which is bonded in the ortho-position to the metal coordination to represent a coordinating group which is likewise coordinated or bonded to the metal M. Preferred coordinating groups R are aryl or heteroaryl groups, for example phenyl or pyridyl, aryl or alkyl cyanides, aryl or alkyl isocyanides, amines or amides, alcohols or alcoholates, thioalcohols or thioalcoholates, phosphines, phosphites, carbonyl functions, carboxylates, carbamides or aryl- or alkyl-acetylides. Examples of moieties ML of the formula (2) are the structures of the following formulae (6) to (11):

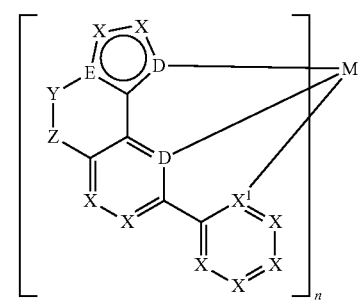 formula (6)

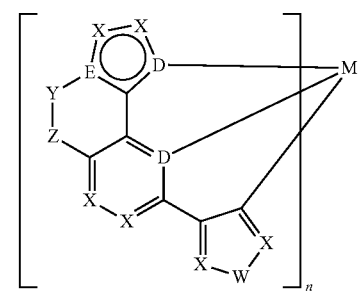 formula (7)

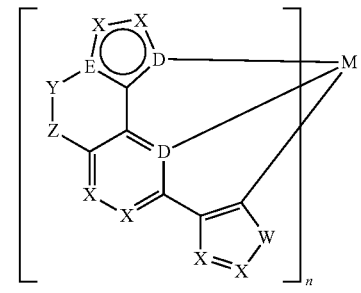 formula (8)

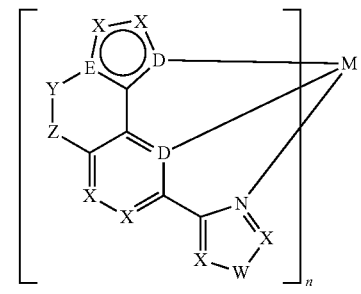 formula (9)

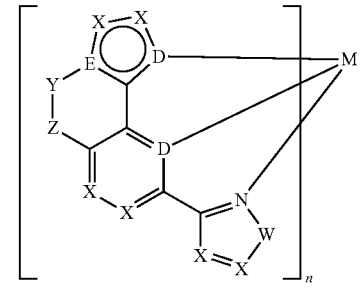 formula (10)

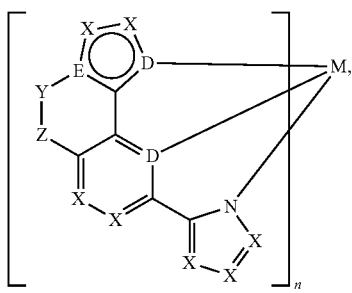

formula (11)

where the symbols and indices have the same meanings as described above, $X^1$ stands, identically or differently on each occurrence, for C or N and W stands, identically or differently on each occurrence, for S, O or $NR^2$.

Formulae (6) to (11) show, merely by way of example, how the substituent R can additionally coordinate to the metal. Other groups R which coordinate to the metal, for example also carbenes, are also accessible entirely analogously without further inventive step. Corresponding moieties ML based on formula (3) are likewise possible entirely analogously.

As described above, a bridging unit which links this ligand L to one or more further ligands L or L' may also be present instead of one of the radicals R. In this case, L or L' does not stand for a separate ligand, but instead for a coordinating group. In a preferred embodiment of the invention, a bridging unit is present instead of one of the radicals R, in particular instead of the radicals R which are in the ortho- or meta-position to the coordinating atom, so that the ligands have a tridentate, polydentate or polypodal character. It is also possible for two such bridging units to be present. This results in the formation of macrocyclic ligands or in the formation of cryptands.

Preferred structures containing polydentate ligands are the metal complexes of the following formulae (12) to (23),

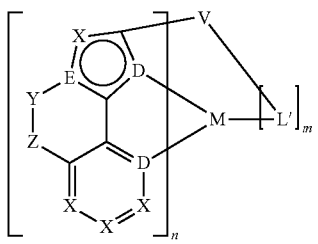

formula (12)

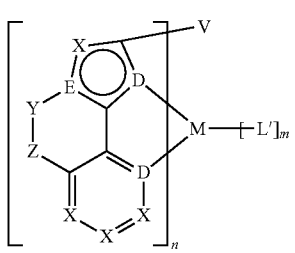

formula (13)

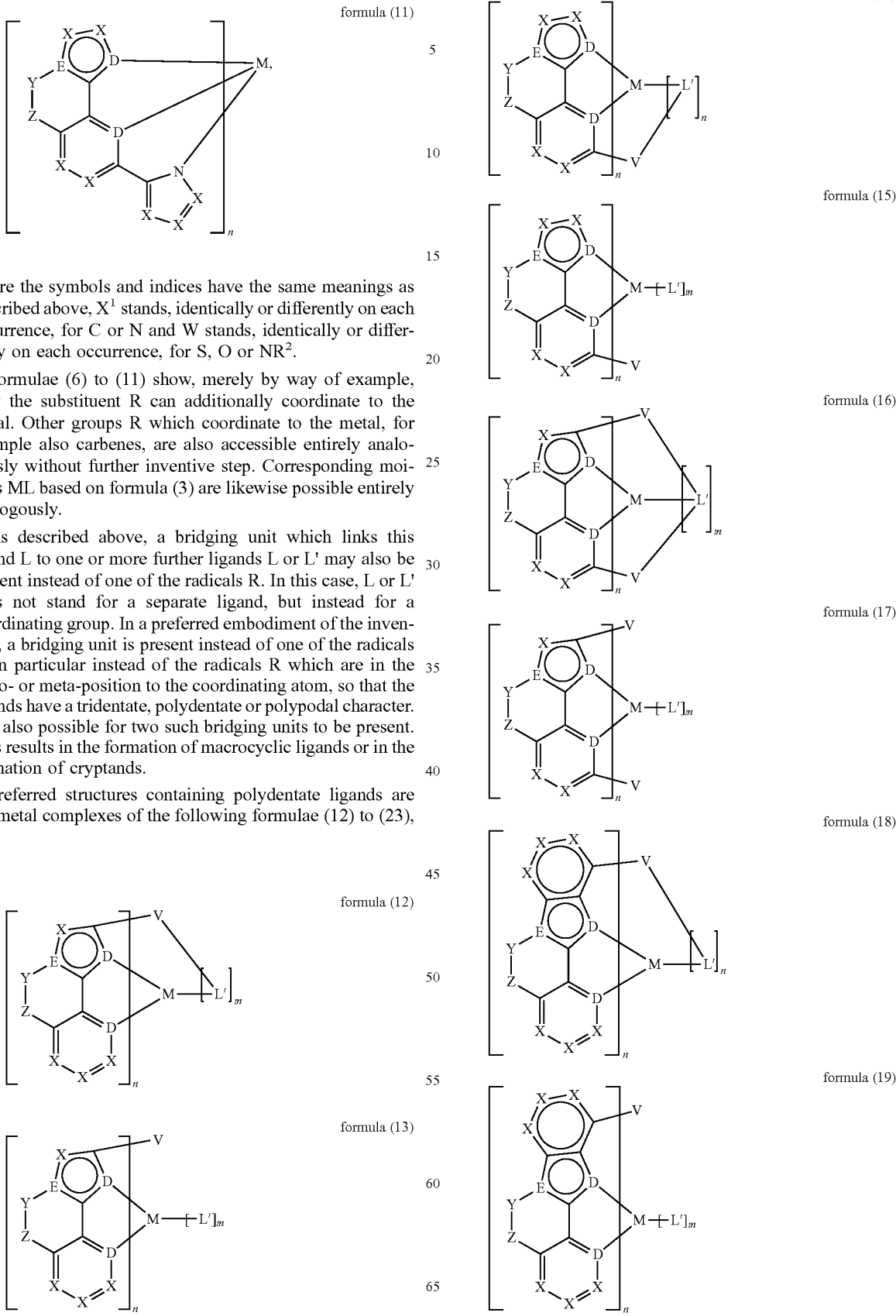

formula (20)

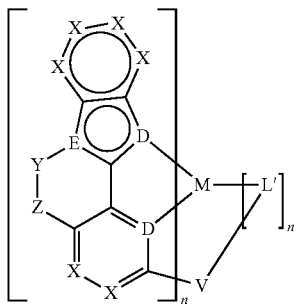

formula (21)

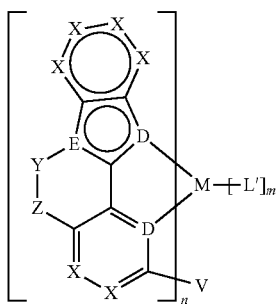

formula (22)

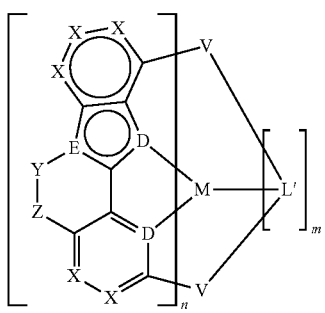

formula (23)

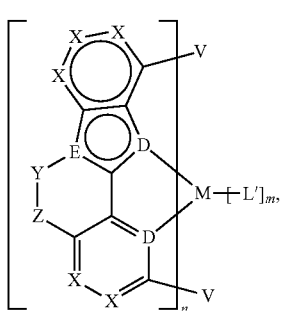

where the symbols and indices used have the meanings given above.

V here preferably represents a single bond or a bridging unit containing 1 to 80 atoms from the third, fourth, fifth and/or sixth main group (IUPAC group 13, 14, 15 or 16) or a 3- to 6-membered homo- or heterocycle which covalently bonds the part-ligands L to one another or covalently bonds L to L'. The bridging unit V here may also have an asymmetrical structure, i.e. the linking of V to L and L' need not be identical. The bridging unit V can be neutral, singly, doubly or triply negatively charged or singly, doubly or triply positively charged. V is preferably neutral or singly negatively charged or singly positively charged, particularly preferably neutral. The charge of V is preferably selected so that overall a neutral complex forms. The preferences mentioned above for the moiety $ML_n$ apply to the ligands, and n is preferably at least 2.

The precise structure and chemical composition of the group V does not have a significant effect on the electronic properties of the complex since the job of this group is essentially to increase the chemical and thermal stability of the complexes by bridging L to one another or to L'.

If V is a trivalent group, i.e. bridges three ligands L to one another or two ligands L to L' or one ligand L to two ligands L', V is preferably selected, identically or differently on each occurrence, from the group consisting of B, $B(R^2)^-$, $B(C(R^2)_2)_3$, $(R^2)B(C(R^2)_2)_3^-$, $B(O)_3$, $(R^2)B(O)_3^-$, $B(C(R^2)_2C(R^2)_2)_3$, $(R^2)B(C(R^2)_2C(R^2)_2)_3^-$, $B(C(R^2)_2O)_3$, $(R^2)B(C(R^2)_2O)_3^-$, $B(OC(R^2)_2)_3$, $(R^2)B(OC(R^2)_2)_3^-$, $C(R^2)$, $CO^-$, $CN(R^2)_2$, $(R^2)C(C(R^2)_2)_3$, $(R^2)C(O)_3$, $(R^2)C(C(R^2)_2C(R^2)_2)_3$, $(R^2)C(C(R^2)_2O)_3$, $(R^2)C(OC(R^2)_2)_3$, $(R^2)C(Si(R^2)_2)_3$, $(R^2)C(Si(R^2)_2C(R^2)_2)_3$, $(R^2)C(C(R^2)_2Si(R^2)_2)_3$, $(R^2)C(Si(R^2)_2Si(R^2)_2)_3$, $Si(R^2)$, $(R^2)Si(C(R^2)_2)_3$, $(R^2)Si(O)_3$, $(R^2)Si(C(R^2)_2)_3$, $(R^2)Si(OC(R^2)_2)_3$, $(R^2)Si(C(R^2)_2O)_3$, $(R^2)Si(Si(R^2)_2)_3$, $(R^2)Si(Si(R^2)_2C(R^2)_2)_3$, $(R^2)Si(C(R^2)_2Si(R^2)_2)_3$, $(R^2)Si(Si(R^2)_2Si(R^2)_2)_3$, N, NO, $N(R^2)^+$, $N(C(R^2)_2)_3$, $(R^2)N(C(R^2)_2)_3^+$, $N(C=O)_3$, $N(C(R^2)_2C(R^2)_2)_3$, $(R^2)N(C(R^2)_2C(R^2)_2)^+$, P, $P(R^2)^+$, PO, PS, $P(O)_3$, $PO(O)_3$, $P(OC(R^2)_2)_3)$, $PO(OC(R^2)_2)_3$, $P(C(R^2)_2)_3$, $P(R^2)(C(R^2)_2)_3^+$, $PO(C(R^2)_2)_3$, $P(C(R^2)_2C(R^2)_2)_3$, $P(R^2)(C(R^2)_2C(R^2)_2)_3^+$, $PO(C(R^2)_2C(R^2)_2)_3$, $S^+$, $S(C(R^2)_2)_3^+$, $S(C(R^2)_2C(R^2)_2)_3^+$, or a unit of one of the formula (24) to (28), formula (24)

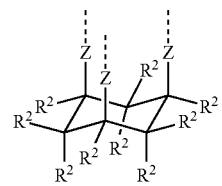

formula (25)

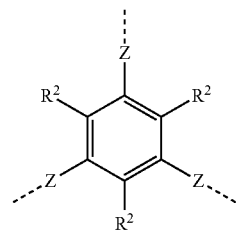

formula (26)

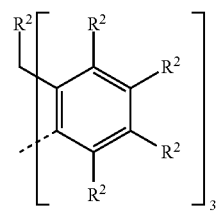

formula (27)

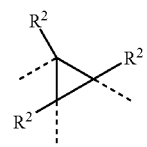

formula (28)

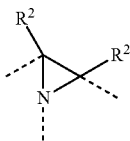

where the dashed bonds in each case indicate the bond to the part-ligands L or L', and Z is selected, identically or differently on each occurrence, from the group consisting of a single bond, O, S, S(=O), S(=O)$_2$, NR$^2$, PR$^2$, P(=O)R$^2$, C(R$^2$)$_2$, C(=O), C(=NR$^2$), C(=C(R$^2$)$_2$), Si(R$^2$)$_2$ or BR$^2$. The other symbols used have the meanings given above.

If V is a divalent group, i.e. bridges two ligands L to one another or one ligand L to L', V is preferably selected, identically or differently on each occurrence, from the group consisting of aus BR$^2$, B(R$^2$)$_2$—, C(R$^2$)$_2$, C(=O), Si(R$^2$)$_2$, NR$^2$, PR$^2$, P(R$^2$)$_2^+$, P(=O)(R$^2$), P(=S)(R$^2$), O, S, Se, or a unit of the formulae (29) to (38), formula (29)

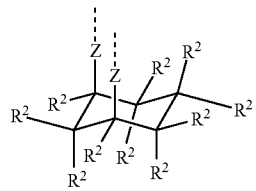

formula (30)

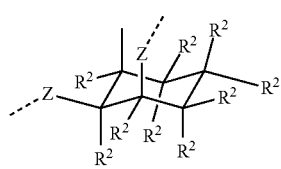

formula (31)

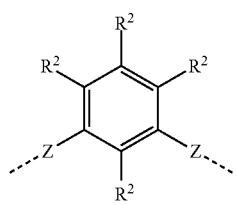

formula (32)

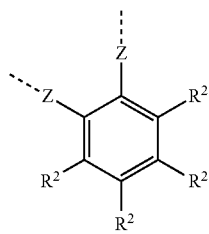

formula (33)

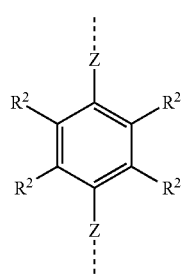

formula (34)

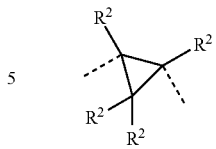

formula (35)

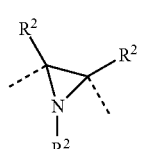

formula (36)

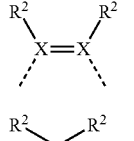

formula (37)

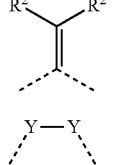

formula (38)

Y—Y where the dashed bonds in each case indicate the bond to the part-ligands L or L', Y stands on each occurrence, identically or differently, for C(R$^2$)$_2$, N(R$^2$), O or S, and the other symbols used each have the meanings indicated above.

If V stands for a group CR$_2$, the two radicals R may also be linked to one another, and consequently structures such as, for example, 9,9-fluorene, are also suitable groups V.

Preferred ligands L' as occur in formula (1) are described below. The ligand groups L' can also be selected correspondingly if they are bonded to L via a bridging unit V, as indicated in formulae (12), (14), (16), (18), (20) and (22), if these groups have a free valence for bonding to V.

The ligands L' are preferably neutral, monoanionic, dianionic or trianionic ligands, particularly preferably neutral or monoanionic ligands. They can be monodentate, bidentate, tridentate or tetradentate and are preferably bidentate, i.e. preferably have two coordination sites. As described above, the ligands L' can also be bonded to L via a bridging group V.

Preferred neutral, monodentate ligands L' are selected from the group consisting of carbon monoxide, nitrogen monoxide, alkyl cyanides, such as, for example, acetonitrile, aryl cyanides, such as, for example, benzonitrile, alkyl isocyanides, such as, for example, methyl isonitrile, aryl isocyanides, such as, for example, benzoisonitrile, amines, such as, for example, trimethylamine, triethylamine, morpholine, phosphines, in particular halophosphines, trialkylphosphines, triarylphosphines or alkylarylphosphines, such as, for example, trifluorophosphine, trimethylphosphine, tricyclohexylphosphine, tri-tert-butylphosphine, triphenylphosphine, tris(pentafluorophenyl)phosphine, dimethylphenylphosphine, methyldiphenylphosphine, bis(tert-butyl)phenylphosphine, phosphites, such as, for example, trimethyl phosphite, triethyl phosphite, arsines, such as, for example, trifluoroarsine, trimethylarsine, tricyclohexylarsine, tri-tert-butylarsine, triphenylarsine, tris(pentafluorophenyl)arsine, stibines, such as, for example, trifluorostibine, trimethylstibine, tricyclohexylstibine, tri-tert-butylstibine, triphenylstibine, tris(pentafluorophenyl)stibine, nitrogen-containing heterocycles, such as, for example, pyridine, pyridazine, pyrazine, pyrimidine, triazine, and carbenes, in particular Arduengo carbenes.

Preferred monoanionic, monodentate ligands L' are selected from hydride, deuteride, the halides F⁻, Cl⁻, Br⁻ and I⁻, alkylacetylides, such as, for example, methyl-C≡C⁻, tert-butyl-C≡C⁻, arylacetylides, such as, for example, phenyl-C≡C⁻, cyanide, cyanate, isocyanate, thiocyanate, isothiocyanate, aliphatic or aromatic alcoholates, such as, for example, methanolate, ethanolate, propanolate, isopropanolate, tert-butylate, phenolate, aliphatic or aromatic thioalcoholates, such as, for example, methanethiolate, ethanethiolate, propanethiolate, isopropanethiolate, tert-thiobutylate, thiophenolate, amides, such as, for example, dimethylamide, diethylamide, diisopropylamide, morpholide, carboxylates, such as, for example, acetate, trifluoroacetate, propionate, benzoate, aryl groups, such as, for example, phenyl, naphthyl, and anionic, nitrogen-containing heterocycles, such as pyrrolide, imidazolide, pyrazolide. The alkyl groups in these groups are preferably $C_1$-$C_{20}$-alkyl groups, particularly preferably $C_1$-$C_{10}$-alkyl groups, very particularly preferably $C_1$-$C_4$-alkyl groups. An aryl group is also taken to mean heteroaryl groups. These groups are as defined above.

Preferred di- or trianionic ligands are $O^{2-}$, $S^{2-}$, carbides, which result in coordination in the form R—C≡M, and nitrenes, which result in coordination in the form R—N=M, where R generally stands for a substituent, or $N^{3-}$.

Preferred neutral or mono- or dianionic, bidentate or polydentate ligands L' are selected from diamines, such as, for example, ethylenediamine, N,N,N',N'-tetramethylethylenediamine, propylenediamine, N,N,N',N'-tetramethylpropylenediamine, cis- or trans-diaminocyclohexane, cis- or trans-N,N,N',N'-tetramethyldiaminocyclohexane, imines, such as, for example, 2-[1-(phenylimino)ethyl]pyridine, 2-[1-(2-methylphenylimino)ethyl]pyridine, 2-[1-(2,6-diisopropylphenylimino)ethyl]pyridine, 2-[1-(methylimino) ethyl]-pyridine, 2-[1-(ethylimino)ethyl]pyridine, 2-[1-(isopropylimino)ethyl]pyridine, 2-[1-(tert-butylimino)ethyl] pyridine, diimines, such as, for example, 1,2-bis-(methylimino)ethane, 1,2-bis(ethylimino)ethane, 1,2-bis (isopropylimino)-ethane, 1,2-bis(tert-butylimino)ethane, 2,3-bis(methylimino)butane, 2,3-bis-(ethylimino)butane, 2,3-bis(isopropylimino)butane, 2,3-bis(tert-butylimino)-butane, 1,2-bis(phenylimino)ethane, 1,2-bis(2-methylphenylimino)ethane, 1,2-bis(2,6-diisopropylphenylimino)ethane, 1,2-bis(2,6-di-tert-butylphenylimino)ethane, 2,3-bis (phenylimino)butane, 2,3-bis(2-methylphenylimino)-butane, 2,3-bis(2,6-diisopropylphenylimino)butane, 2,3-bis (2,6-di-tert-butyl-phenylimino)butane, heterocycles containing two nitrogen atoms, such as, for example, 2,2'-bipyridine, o-phenanthroline, diphosphines, such as, for example, bis(diphenylphosphino)methane, bis(diphenylphosphino)ethane, bis(diphenylphosphino)propane, bis(diphenylphosphino)butane, bis-(dimethylphosphino)methane, bis(dimethylphosphino)ethane, bis(dimethyl-phosphino) propane, bis(diethylphosphino)methane, bis(diethylphosphino)-ethane, bis(diethylphosphino)propane, bis(di-tert-butylphosphino)methane, bis(di-tert-butylphosphino) ethane, bis(tert-butylphosphino)propane, 1,3-diketonates derived from 1,3-diketones, such as, for example, acetylacetone, benzoylacetone, 1,5-diphenylacetylacetone, dibenzoylmethane, bis(1,1,1-trifluoroacetyl)methane, 3-ketonates derived from 3-ketoesters, such as, for example, ethyl acetoacetate, carboxylates derived from aminocarboxylic acids, such as, for example, pyridine-2-carboxylic acid, quinoline-2-carboxylic acid, glycine, N,N-dimethylglycine, alanine, N,N-dimethylaminoalanine, salicyliminates derived from salicylimines, such as, for example, methylsalicylimine, ethylsalicylimine, phenylsalicylimine, dialcoholates derived from dialcohols, such as, for example, ethylene glycol, 1,3-propylene glycol, and dithiolates derived from dithiols, such as, for example, 1,2-ethylenedithiol, 1,3-propylenedithiol, bis(pyrazolyl)borates, bis(imidazolyl)borates, 3-(2-pyridyl)diazoles or 3-(2-pyridyl)triazoles.

Preferred tridentate ligands are borates of nitrogen-containing heterocycles, such as, for example, tetrakis(1-imidazolyl)borate and tetrakis-(1-pyrazolyl)borate.

Preference is furthermore given to bidentate monoanionic, neutral or dianionic ligands L', in particular monoanionic ligands, which, with the metal, form a cyclometallated five- or six-membered ring with at least one metal-carbon bond, in particular a cyclometallated five-membered ring. These are, in particular, ligands as are generally used in the area of phosphorescent metal complexes for organic electroluminescent devices, i.e. ligands of the type phenylpyridine, naphthylpyridine, phenylquinoline, phenylisoquinoline, etc., each of which may be substituted by one or more radicals R. A multiplicity of ligands of this type is known to the person skilled in the art in the area of phosphorescent electroluminescent devices, and he will be able, without inventive step, to select further ligands of this type as ligand L' for compounds of the formula (1). The combination of two groups as depicted by the following formulae (39) to (70) is generally particularly suitable for this purpose, where one group is preferably bonded via a neutral nitrogen atom or a carbene carbon atom and the other group is preferably bonded via a negatively charged carbon atom or a negatively charged nitrogen atom. The ligand L' can then be formed from the groups of the formulae (39) to (70) through these groups bonding to one another in each case at the position denoted by #. The position at which the groups coordinate to the metal is denoted by *. These groups may also be bonded to the ligand L via one or two bridging units V.

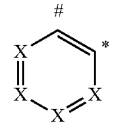

formula (39)

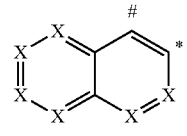

formula (40)

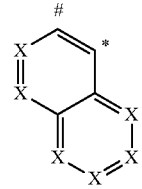

formula (41)

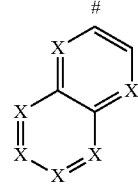

formula (42)

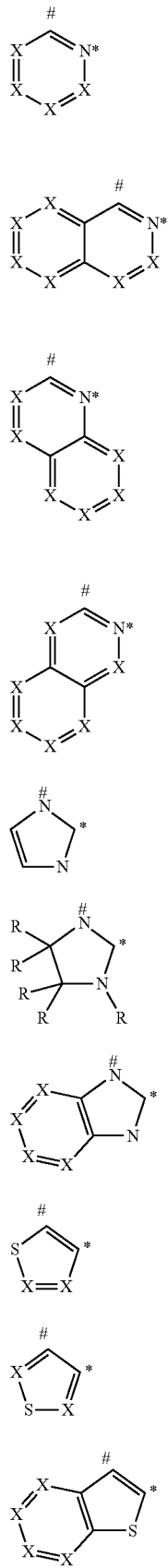
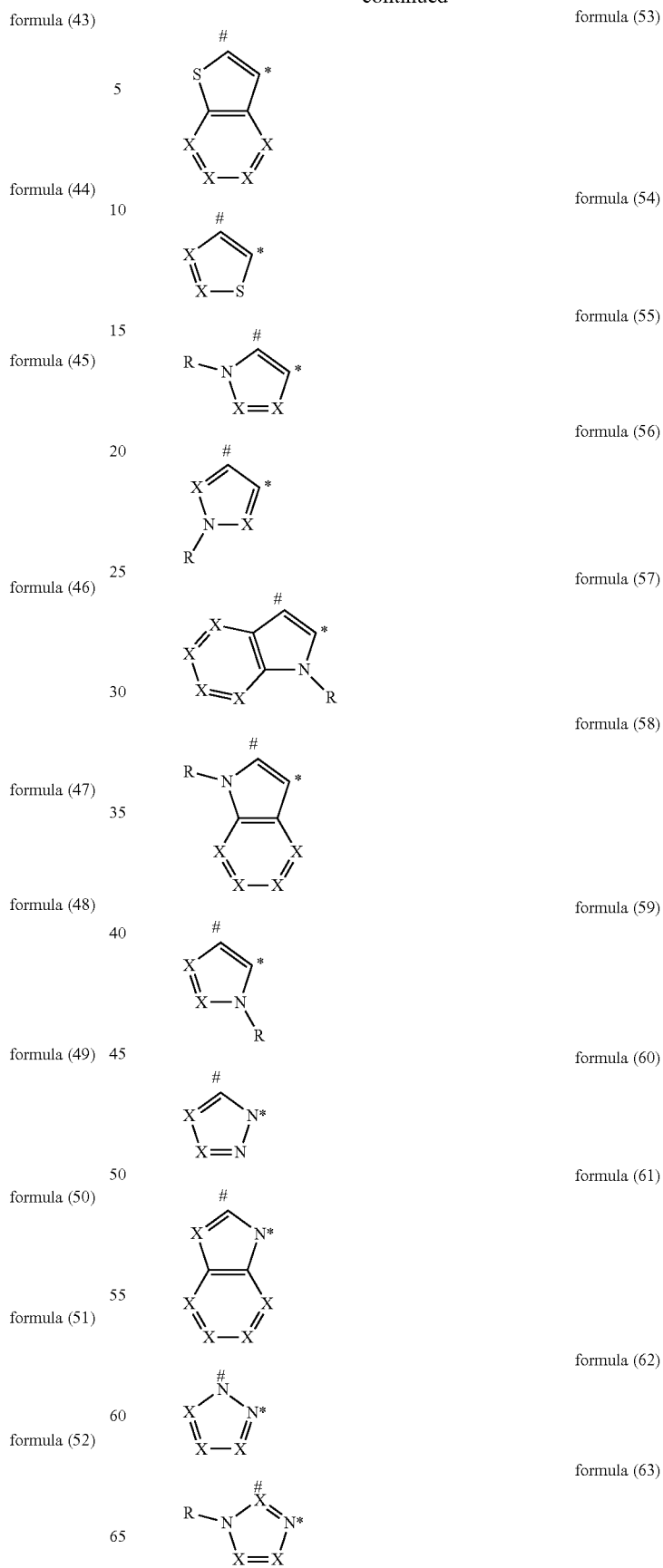

formula (64)
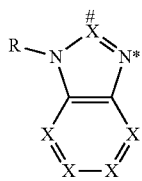

formula (65)

formula (66)
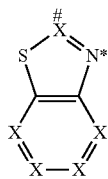

formula (67)
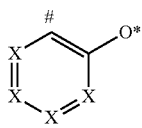

formula (68)
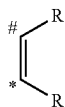

formula (69)

formula (70)

formula (71)
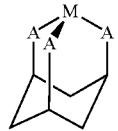

formula (72)
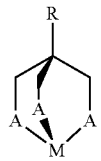

formula (73)
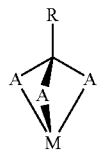

formula (74)
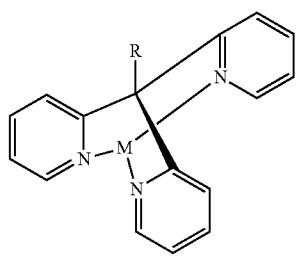

where the coordination to the metal M is shown in each of the formulae, R has the meaning given above, and A stands, identically or differently on each occurrence, for O⁻, S⁻, COO⁻, PR$_2$ or NR$_2$.

The complexes according to the invention can be facial or pseudofacial or they can be meridional or pseudomeridional.

The ligands L may also be chiral, depending on the structure or substitution. This may be the case, for example, if they contain a condensed-on bicyclic group as substituent or if they contain substituents, for example alkyl, alkoxy, dialkylamino or aralkyl groups, which have one or more stereocentres. Since the basic structure of the complex may also be a chiral structure, the formation of diastereomers and a number of enantiomer pairs is possible. The complexes according to the invention then encompass both the mixtures of the various diastereomers or the corresponding racemates and also the individual isolated diastereomers or enantiomers.

The symbols used have the same meaning here as described above, and the above-mentioned preference for the groups used applies. Preferably, a maximum of three symbols X in each group stand for N, particularly preferably a maximum of two symbols X in each group stand for N, very particularly preferably a maximum of one symbol X in each group stands for N. Especially preferably, all symbols X stand for CR.

Furthermore, the formulae (50) to (54), (65) and (66) may also contain oxygen instead of sulfur.

Likewise preferred ligands L' are η⁵-cyclopentadienyl, η⁵-pentamethyl-cyclopentadienyl, η⁶-benzene or η⁷-cycloheptatrienyl, each of which may be substituted by one or more radicals R.

Likewise preferred ligands L' are 1,3,5-cis,cis-cyclohexane derivatives, in particular of the formula (71), 1,1,1-tri(methylene)methane derivatives, in particular of the formula (72), and 1,1,1-trisubstituted methanes, in particular of the formula (73) and (74), The preferred embodiments indicated above can be combined with one another as desired. In a particularly preferred embodiment of the invention, a plurality or all of the preferred embodiments indicated above apply simultaneously.

Examples of preferred compounds according to the invention are the compounds shown in the following table.

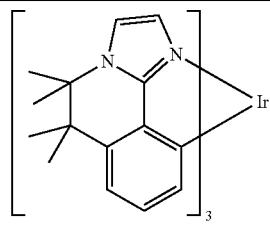

1

| | |
|---|---|
| 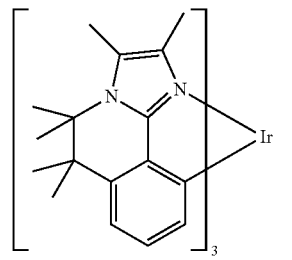 2 | 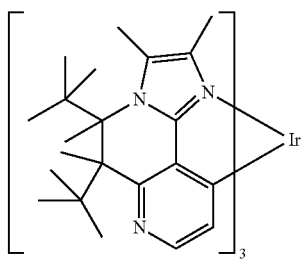 8 |
| 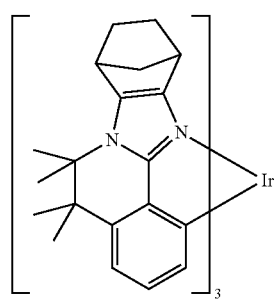 3 | 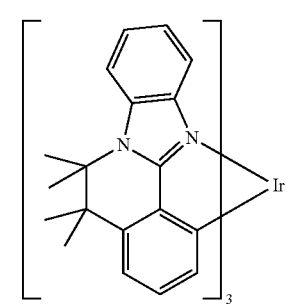 9 |
| 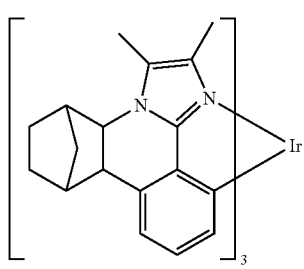 4 | 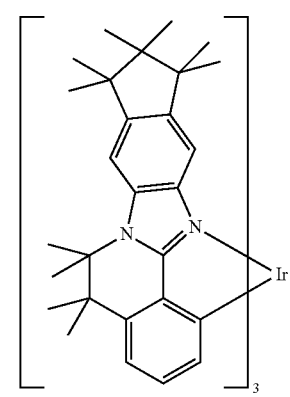 10 |
| 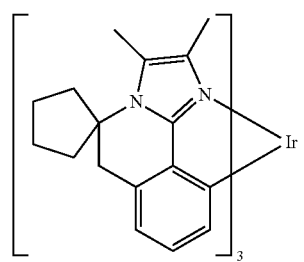 5 | 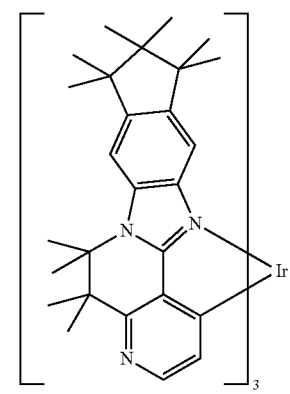 11 |
| 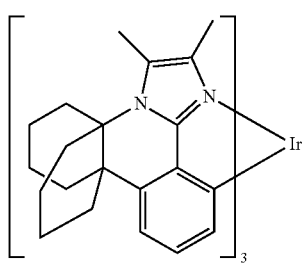 6 | |
| 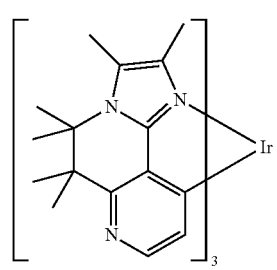 7 | |

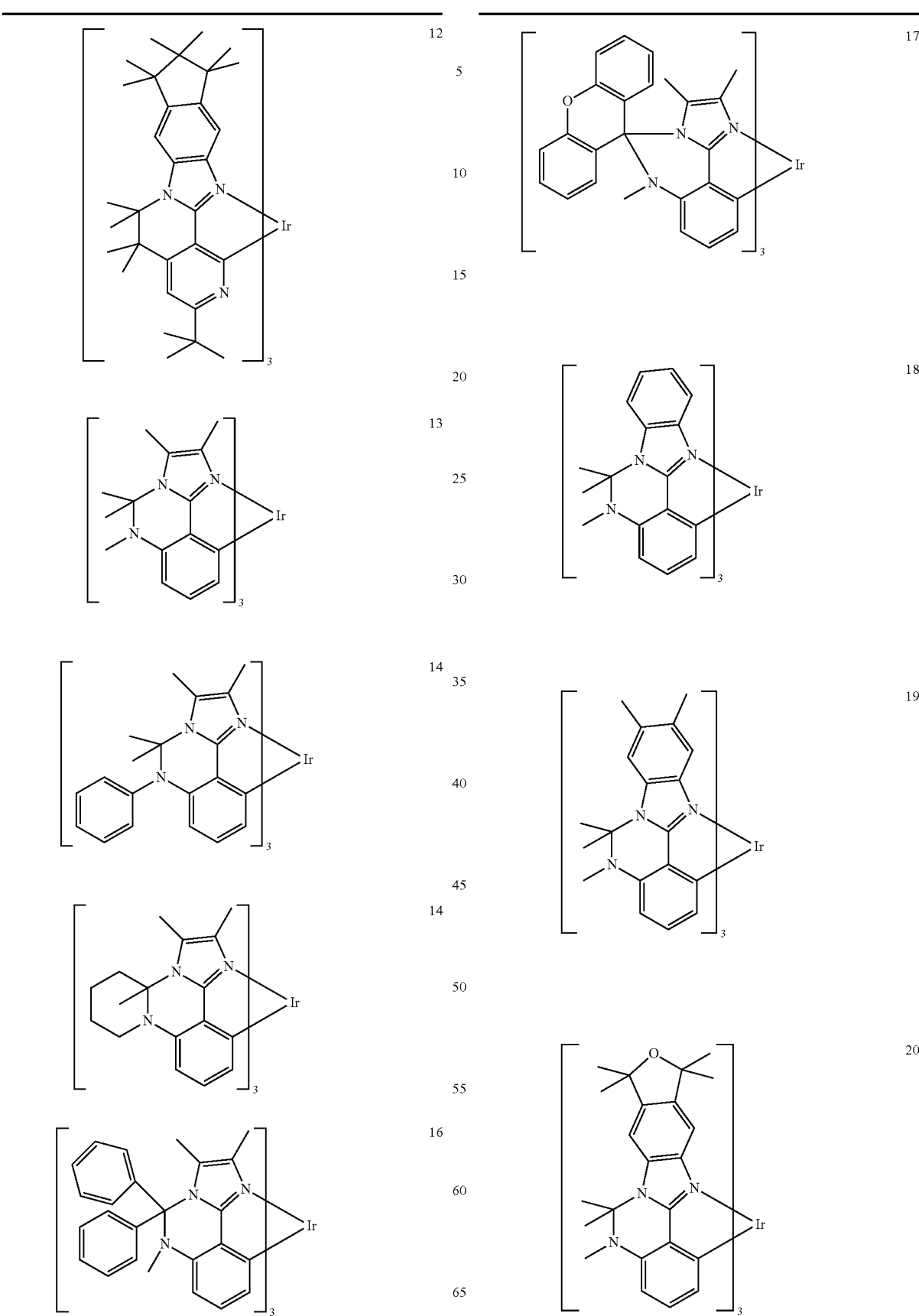

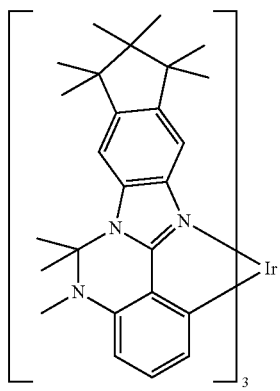
21
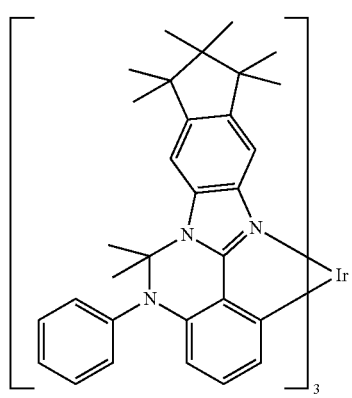
22
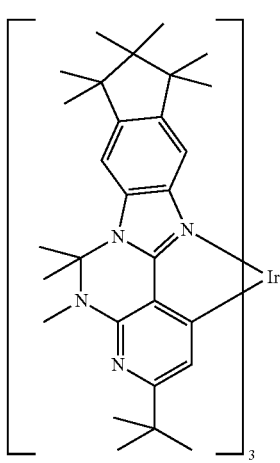
23
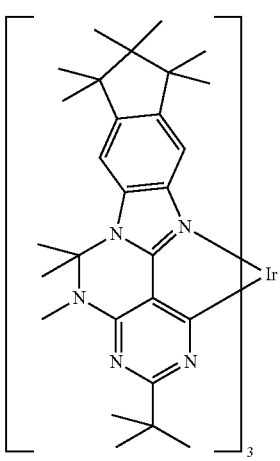
24
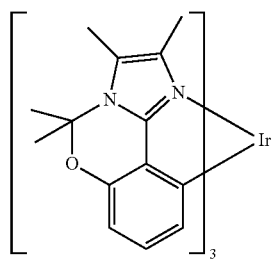
25
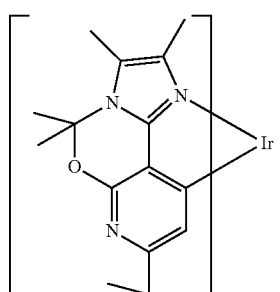
26
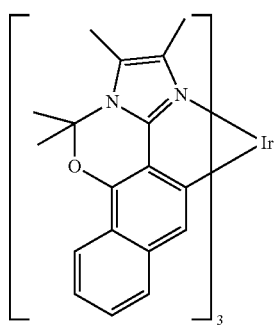
27

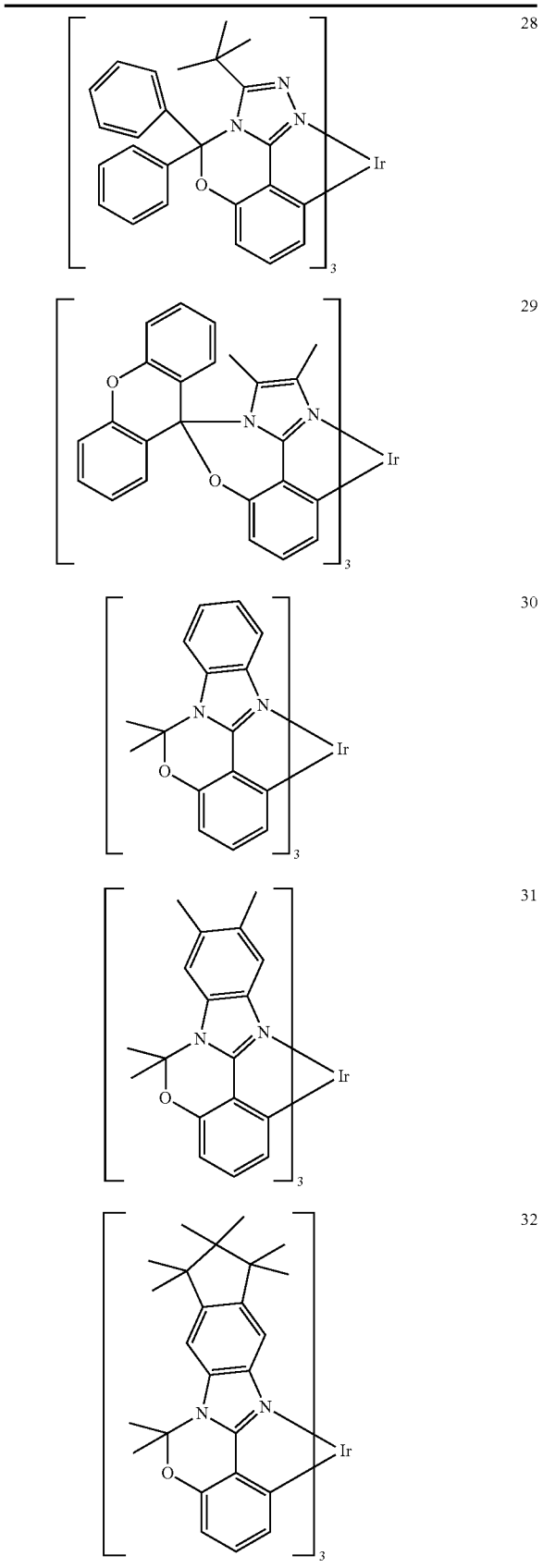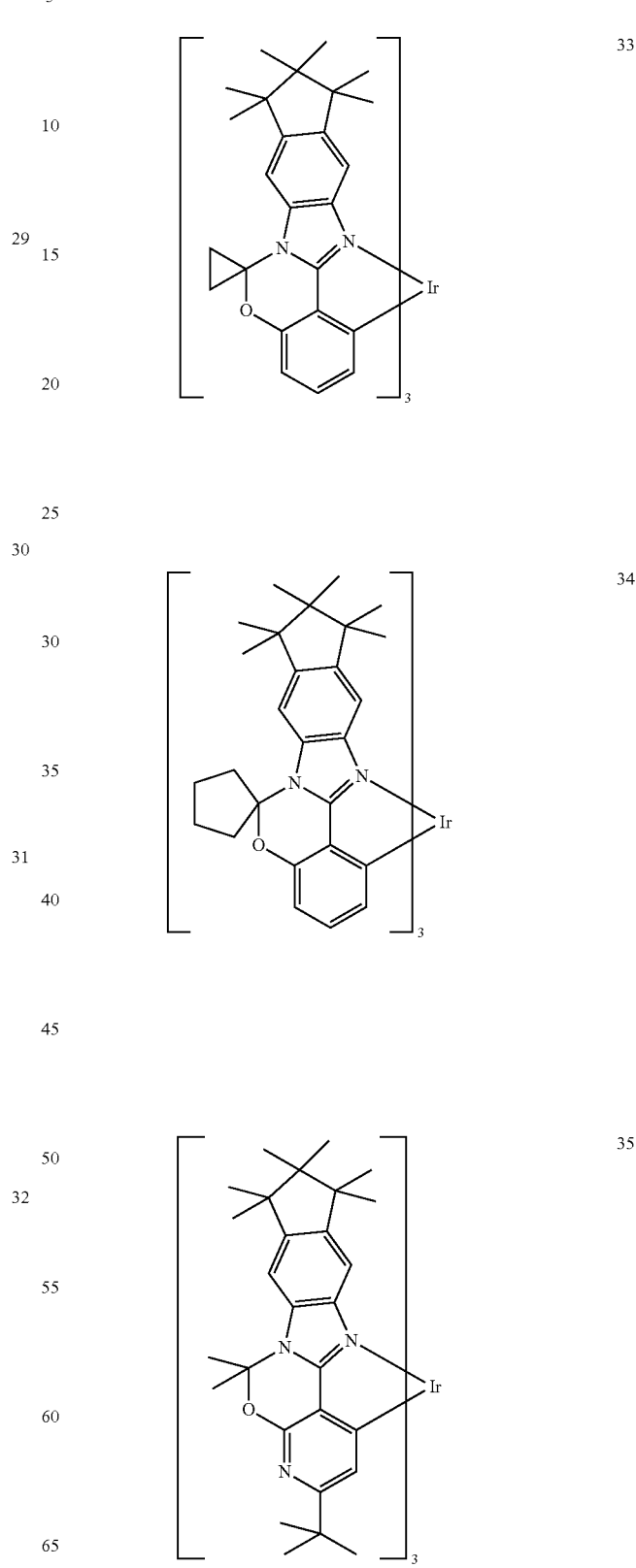

36
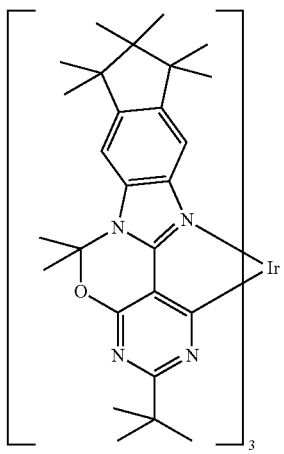
37
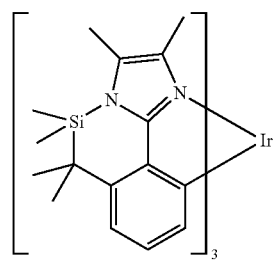
38
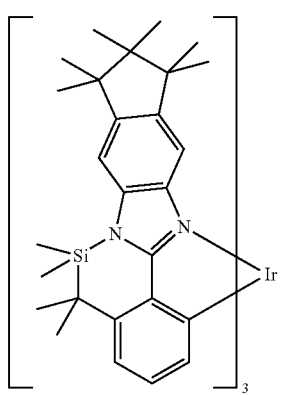
39
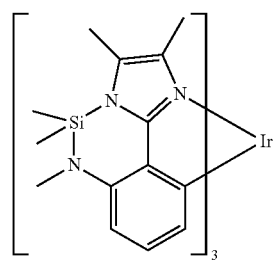
40
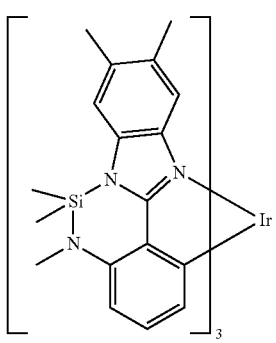
41
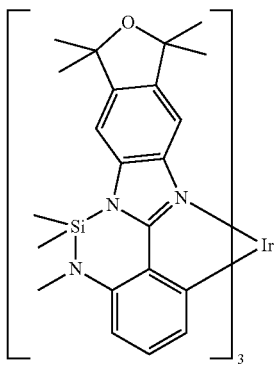
42
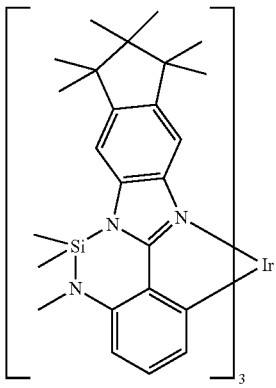
43
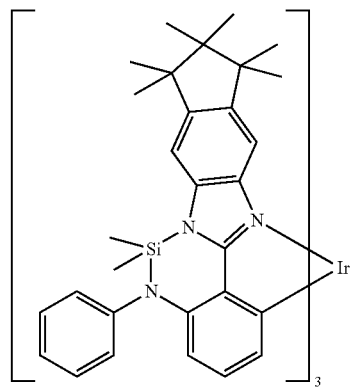

| 44 | 48 |
|---|---|
| 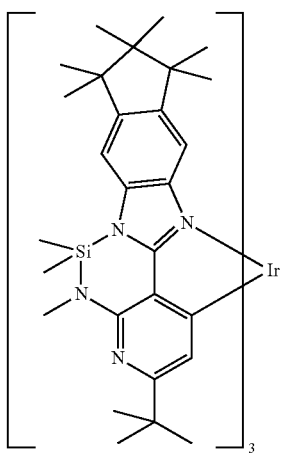 | 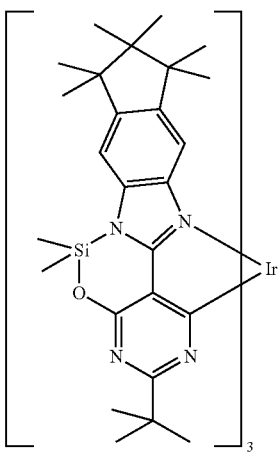 |
| 45 | 49 |
| 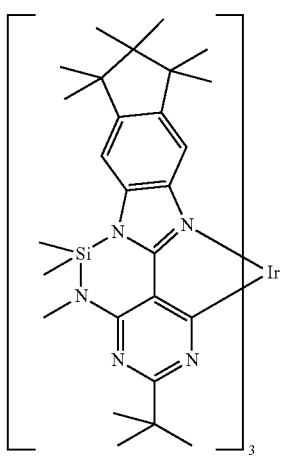 | 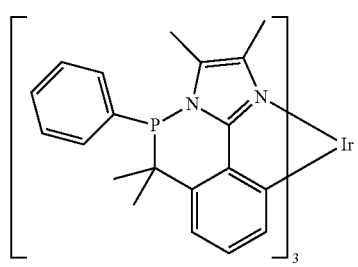 |
| 46 | 50 |
| 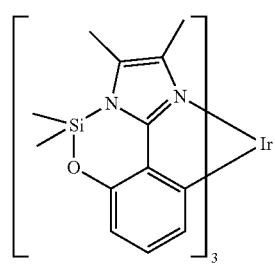 | 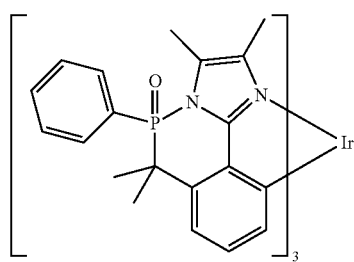 |
| 47 | 51 |
| 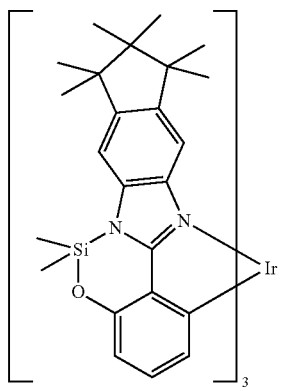 | 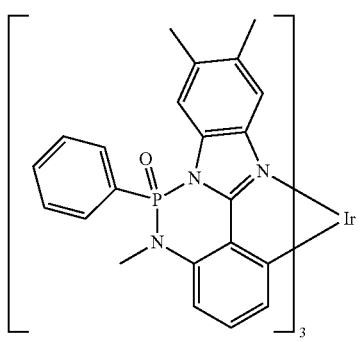 |

-continued
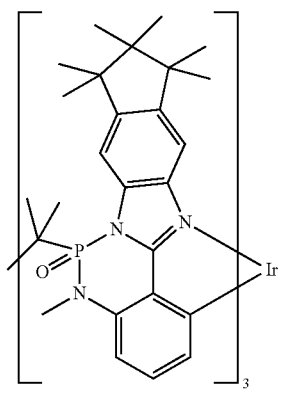
52
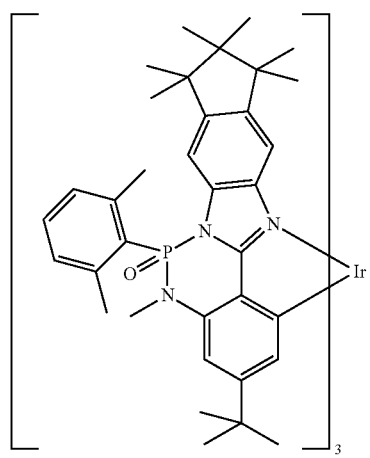
53
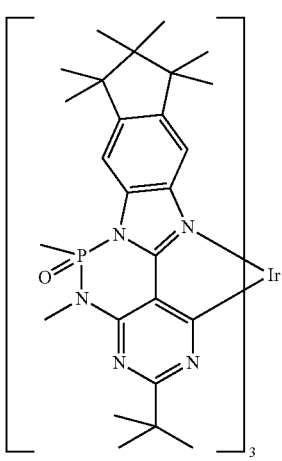
54
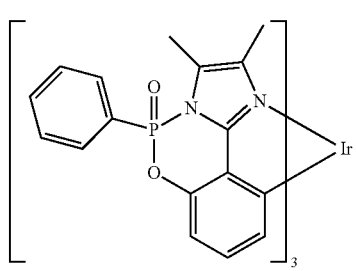
55
-continued
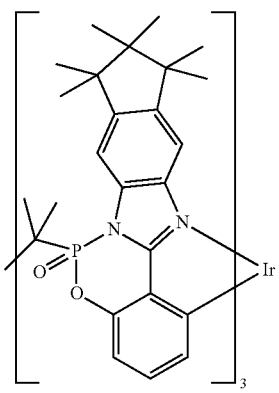
56
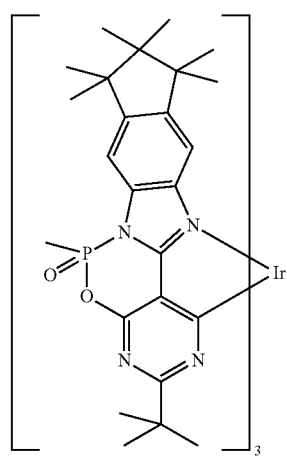
57
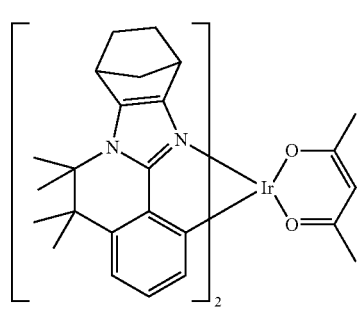
58
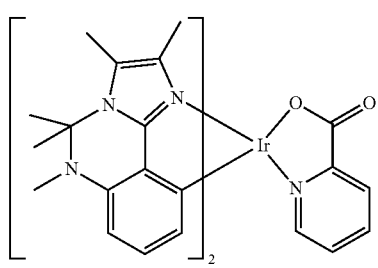
59

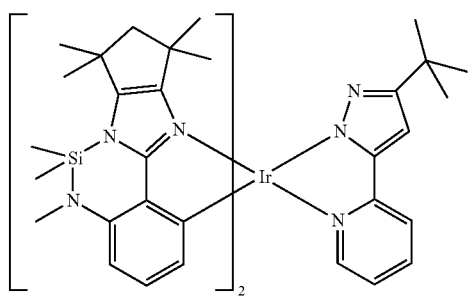
60
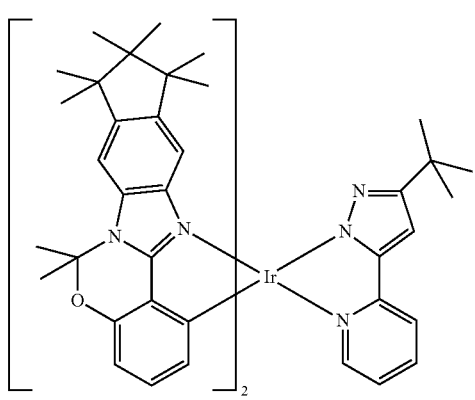
61
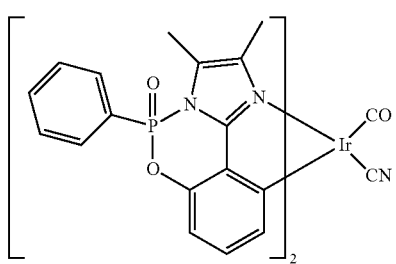
62
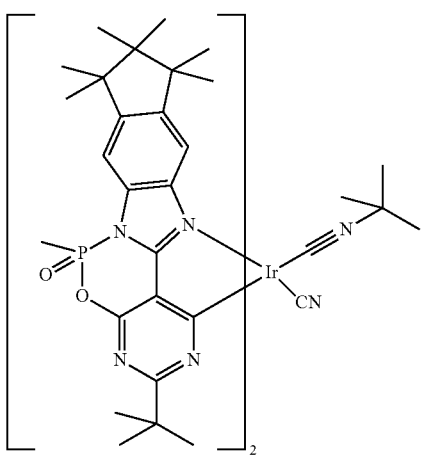
63
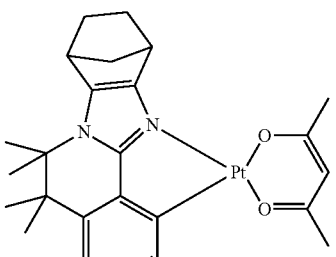
64
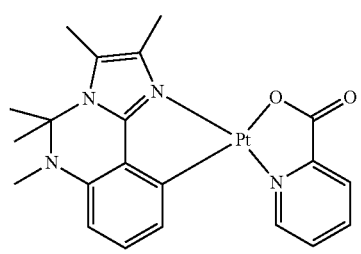
65
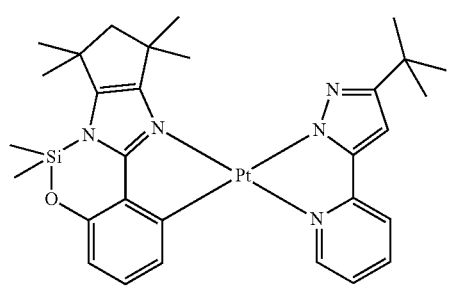
66
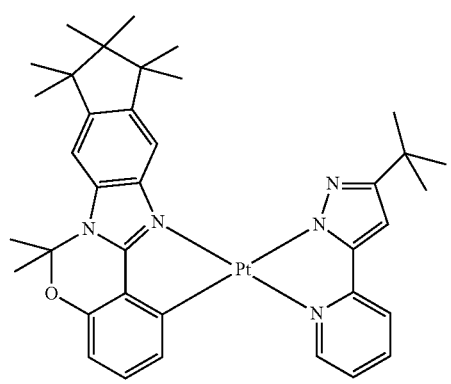
68
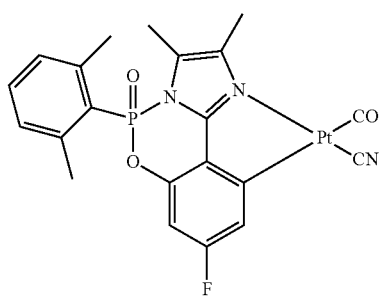
69

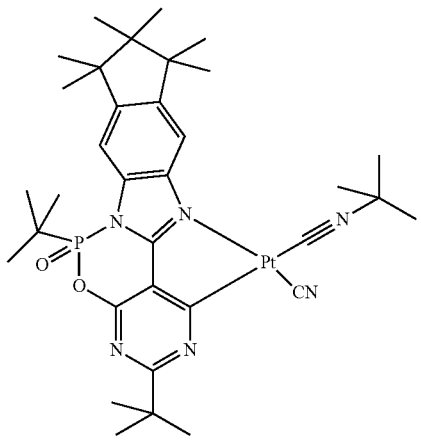

The metal complexes according to the invention can in principle be prepared by various processes. However, the processes described below have proven particularly suitable.

The present invention therefore furthermore relates to a process for the preparation of the compounds of the formula (1) by reaction of the corresponding free ligands with metal alkoxides of the formula (75), with metal ketoketonates of the formula (76), with metal halides of the formula (77) or with dimeric metal complexes of the formula (78) or with metal complexes of the formula (79),

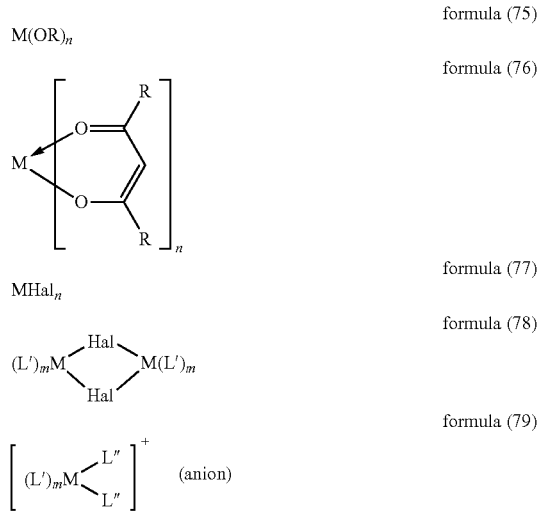

formula (75)
formula (76)
formula (77)
formula (78)
formula (79)

where the symbols M, m, n and R have the meanings indicated above, Hal=F, Cl, Br or I, L" stands for an alcohol, in particular for an alcohol having 1 to 4 C atoms, or a nitrile, in particular acetonitrile or benzonitrile, and (anion) stands for a non-coordinating anion, such as, for example, triflate.

It is likewise possible to use metal compounds, in particular iridium compounds, which carry both alkoxide and/or halide and/or hydroxyl radicals as well as ketoketonate radicals. These compounds may also be charged. Corresponding iridium compounds which are particularly suitable as starting materials are disclosed in WO 2004/085449. [IrCl$_2$(acac)$_2$]$^-$, for example Na[IrCl$_2$(acac)$_2$], are particularly suitable. Metal complexes with acetylacetonate derivatives as ligand, for example Ir(acac)$_3$ or tris(2,2,6,6-tetramethylheptane-3,5-dionato)iridium, and IrCl$_3$.xH$_2$O, where x usually stands for a number between 2 and 4.

Suitable platinum starting materials are, for example, PtCl$_2$, K$_2$[PtCl$_4$], PtCl$_2$(DMSO)$_2$, Pt(Me)$_2$(DMSO)$_2$ or PtCl$_2$(benzonitrile)$_2$.

The synthesis of the complexes is preferably carried out as described in WO 2002/060910, WO 2004/085449 and WO 2007/065523. Heteroleptic complexes can also be synthesised, for example, in accordance with WO 2005/042548. The synthesis here can also be activated, for example, thermally, photochemically, in a autoclave and/or by microwave radiation. In a preferred embodiment of the invention, the reaction is carried out in the melt without the use of an additional solvent. "Melt" here means that the ligand is in molten form and the metal precursor is dissolved or suspended in this melt. In order to activate the reaction, it is furthermore also possible to add a Lewis acid, for example a silver salt or AlCl$_3$.

These processes, optionally followed by purification, such as, for example, recrystallisation or sublimation, enable the compounds of the formula (1) according to the invention to be obtained in high purity, preferably greater than 99% (determined by means of $^1$H-NMR and/or HPLC).

The compounds according to the invention can also be rendered soluble by suitable substitution, for example by relatively long alkyl groups (about 4 to 20 C atoms), in particular branched alkyl groups, or optionally substituted aryl groups, for example, xylyl, mesityl or branched terphenyl or quaterphenyl groups. Compounds of this type are then soluble in common organic solvents, such as, for example, toluene or xylene, at room temperature in sufficient concentration to be able to process the complexes from solution. These soluble compounds are particularly suitable for processing from solution, for example by printing processes.

The compounds according to the invention can also be mixed with a polymer. It is likewise possible to incorporate these compounds covalently into a polymer. This is possible, in particular, with compounds which are substituted by reactive leaving groups, such as bromine, iodine, chlorine, boronic acid or boronic acid ester, or by reactive, polymerisable groups, such as olefins or oxetanes. These can be used as monomers for the production of corresponding oligomers, dendrimers or polymers. The oligomerisation or polymerisation here preferably takes place via the halogen functionality or the boronic acid functionality or via the polymerisable group. It is furthermore possible to crosslink the polymers via groups of this type. The compounds and polymers according to the invention can be employed as crosslinked or uncrosslinked layer.

The invention therefore furthermore relates to oligomers, polymers or dendrimers containing one or more of the above-mentioned compounds according to the invention, where one or more bonds are present from the compound according to the invention to the polymer, oligomer or dendrimer. Depending on the linking of the compound according to the invention, this therefore forms a side chain of the oligomer or polymer or is linked in the main chain. The polymers, oligomers or dendrimers may be conjugated, partially conjugated or non-conjugated. The oligomers or polymers may be linear, branched or dendritic. The same preferences as described above apply to the recurring units of the compounds according to the invention in oligomers, dendrimers and polymers.

For the preparation of the oligomers or polymers, the monomers according to the invention are homopolymerised or copolymerised with further monomers. Preference is given to copolymers, where the units of the formula (1) or the preferred embodiments described above are present in amounts of 0.01 to 99.9 mol %, preferably 5 to 90 mol %, particularly preferably 20 to 80 mol %. Suitable and preferred comonomers which form the polymer backbone are selected from fluorenes (for example in accordance with EP 842208 or WO 2000/022026), spirobifluorenes (for example in accordance with EP 707020, EP 894107 or WO 2006/061181), paraphenylenes (for example in accordance with WO 92/18552), carbazoles (for example in accordance with WO 2004/070772 or WO 2004/113468), thiophenes (for example in accordance with EP 1028136), dihydrophenanthrenes (for example in accordance with WO 2005/014689), cis- or trans-indenofluorenes (for example in accordance with WO 2004/041901 or WO 2004/113412), ketones (for example in accordance with WO 2005/ 040302), phenanthrenes (for example in accordance with WO 2005/ 104264 or WO 2007/017066) or also a plurality of these units. The polymers, oligomers and dendrimers may also contain further units, for example hole-transport units, in particular those based on triarylamines, and/or electron-transport units.

Processing of the compounds according to the invention from the liquid phase, for example by spin coating or by printing processes, requires formulations of the compounds according to the invention. These formulations can be, for example, solutions, dispersions or emulsions. It may be preferred to use mixtures of two or more solvents for this purpose. Suitable and preferred solvents are, for example, toluene, anisole, o-, m- or p-xylene, methyl benzoate, mesitylene, tetralin, veratrol, THF, methyl-THF, THP, chlorobenzene, dioxane, phenoxytoluene, in particular 3-phenoxytoluene, (−)-fenchone, 1,2,3,5-tetramethylbenzene, 1,2,4,5-tetramethyl-benzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The present invention therefore furthermore relates to a formulation comprising a compound according to the invention or an oligomer, polymer or dendrimer according to the invention and at least one further compound. The further compound may be, for example, a solvent, in particular one of the above-mentioned solvents or a mixture of these solvents. However, the further compound may also be a further organic or inorganic compound which is likewise employed in the electronic device, for example a matrix material. This further compound may also be polymeric.

The complexes of the formula (1) described above or the preferred embodiments indicated above can be used as active component in the electronic device. An electronic device is taken to mean a device which comprises an anode, a cathode and at least one layer, where this layer comprises at least one organic or organometallic compound. The electronic device according to the invention thus comprises an anode, a cathode and at least one layer which comprises at least one compound of the formula (1) given above. Preferred electronic devices here are selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs) or organic laser diodes (O-lasers), comprising at least one compound of the formula (1) given above in at least one layer. Particular preference is given to organic electroluminescent devices. Active components are generally the organic or inorganic materials which have been introduced between the anode and cathode, for example charge-injection, charge-transport or charge-blocking materials, but in particular emission materials and matrix materials. The compounds according to the invention exhibit particularly good properties as emission material in organic electroluminescent devices. Organic electroluminescent devices are therefore a preferred embodiment of the invention. Furthermore, the compounds according to the invention can be employed for the generation of singlet oxygen or in photocatalysis.

The organic electroluminescent device comprises a cathode, an anode and at least one emitting layer. Apart from these layers, it may also comprise further layers, for example in each case one or more hole-injection layers, hole-transport layers, hole-blocking layers, electron-transport layers, electron-injection layers, exciton-blocking layers, electron-blocking layers, charge-generation layers and/or organic or inorganic p/n junctions. It is possible here for one or more hole-transport layers to be p-doped, for example with metal oxides, such as $MoO_3$ or $WO_3$, or with (per)fluorinated electron-deficient aromatic compounds, and/or for one or more electron-transport layers to be n-doped. Interlayers which have, for example, an exciton-blocking function and/or control the charge balance in the electro-luminescent device may likewise be introduced between two emitting layers. However, it should be pointed out that each of these layers does not necessarily have to be present.

The organic electroluminescent device here may comprise one emitting layer or a plurality of emitting layers. If a plurality of emission layers are present, these preferably have in total a plurality of emission maxima between 380 nm and 750 nm, resulting overall in white emission, i.e. various emitting compounds which are able to fluoresce or phosphoresce are used in the emitting layers. Particular preference is given to three-layer systems, where the three layers exhibit blue, green and orange or red emission (for the basic structure see, for example, WO 2005/011013), or systems which have more than three emitting layers. It may also be a hybrid system, where one or more layers fluoresce and one or more other layers phosphoresce.

In a preferred embodiment of the invention, the organic electroluminescent device comprises the compound of the formula (1) or the preferred embodiments indicated above as emitting compound in one or more emitting layers.

If the compound of the formula (1) is employed as emitting compound in an emitting layer, it is preferably employed in combination with one or more matrix materials. The mixture comprising the compound of the formula (1) and the matrix material comprises between 1 and 99% by vol., preferably between 2 and 90% by vol., particularly preferably between 3 and 40% by vol., especially between 5 and 15% by vol., of the compound of the formula mula (1), based on the mixture as a whole comprising emitter and matrix material. Correspondingly, the mixture comprises between 99.9 and 1% by vol., preferably between 99 and 10% by vol., particularly preferably between 97 and 60% by vol., in particular between 95 and 85% by vol., of the matrix material, based on the mixture as a whole comprising emitter and matrix material.

The matrix material employed can in general be all materials which are known for this purpose in accordance with the prior art. The triplet level of the matrix material is preferably higher than the triplet level of the emitter.

Suitable matrix materials for the compounds according to the invention are ketones, phosphine oxides, sulfoxides and sulfones, for example in accordance with WO 2004/013080, WO 2004/093207, WO 2006/005627 or WO 2010/006680, triarylamines, carbazole derivatives, for example CBP (N,N-biscarbazolylbiphenyl), m-CBP or the carbazole derivatives disclosed in WO 2005/039246, US 2005/0069729, JP 2004/288381, EP 1205527, WO 2008/086851 or US 2009/0134784, indolocarbazole derivatives, for example in accordance with WO 2007/063754 or WO 2008/056746, indenocarbazole derivatives, for example in accordance with WO 2010/ 136109 or WO 2011/000455, azacarbazoles, for example in accordance with EP 1617710, EP 1617711, EP 1731584, JP 2005/347160, bipolar matrix materials, for example in accordance with WO 2007/137725, silanes, for example in accordance with WO 2005/111172, azaboroles or boronic esters, for example in accordance with WO 2006/117052, diazasilole derivatives, for example in accordance with WO 2010/054729, diazaphosphole derivatives, for example in accordance with WO 2010/054730, triazine derivatives, for example in accordance with WO 2010/015306, WO 2007/063754 or WO 2008/056746, zinc complexes, for example in accordance with EP 652273 or WO 2009/062578, dibenzofuran derivatives, for example in accordance with WO 2009/148015, or bridged carbazole derivatives, for example in accordance with US 2009/0136779, WO 2010/050778, WO 2011/042107 or WO 2011/088877.

It may also be preferred to employ a plurality of different matrix materials as a mixture, in particular at least one electron-conducting matrix material and at least one hole-conducting matrix material. A preferred combination is, for example, the use of an aromatic ketone, a triazine derivative or a phosphine oxide derivative with a triarylamine derivative or a carbazole derivative as mixed matrix for the metal complex according to the invention. Preference is likewise given to the use of a mixture of a charge-transporting, i.e. a hole- or electron-transporting matrix material and an electrically inert matrix material which is not involved or not essentially involved in charge transport, as described, for example, in WO 2010/ 108579.

It is furthermore preferred to employ a mixture of two or more triplet emitters together with a matrix. The triplet emitter having the shorter-wave emission spectrum serves as co-matrix for the triplet-emitter having the longer-wave emission spectrum. Thus, for example, the complexes of the formula (1) according to the invention can be employed as co-matrix for triplet emitters emitting at longer wavelength, for example for green- or red-emitting triplet emitters.

The compounds according to the invention can also be employed in other functions in the electronic device, for example as hole-transport material in a hole-injection or -transport layer, as charge-generation material or as electron-blocking material. The complexes according to the invention can likewise be employed as matrix material for other phosphorescent metal complexes in an emitting layer.

The cathode preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag, may also be used in addition to the said metals, in which case combinations of the metals, such as, for example, Mg/Ag, Ca/Ag or Ba/Ag, are generally used. It may also be preferred to introduce a thin interlayer of a material having a high dielectric constant between a metallic cathode and the organic semiconductor. Suitable for this purpose are, for example, alkali metal or alkaline-earth metal fluorides, but also the corresponding oxides or carbonates (for example LiF, $Li_2O$, $BaF_2$, MgO, NaF, CsF, $Cs_2CO_3$, etc.). Organic alkali-metal complexes, for example Liq (lithium quinolinate), are likewise suitable for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example Al/Ni/$NiO_x$, Al/$PtO_x$) may also be preferred. For some applications, at least one of the electrodes must be transparent or partially transparent in order either to facilitate irradiation of the organic material (O-SCs) or the coupling-out of light (OLEDs/PLEDs, O-LASERs). Preferred anode materials here are conductive mixed metal oxides. Particular preference is given to indium tin oxide (ITO) or indium zinc oxide (IZO). Preference is furthermore given to conductive, doped organic materials, in particular conductive doped polymers, for example PEDOT, PANI or derivatives of these polymers. It is furthermore preferred for a p-doped hole-transport material to be applied to the anode as hole-injection layer, where suitable p-dopants are metal oxides, for example MoO3 or WO3, or (per)fluorinated electron-deficient aromatic compounds. Further suitable p-dopants are HAT-CN (hexacyanohexaazatriphenylene) or the compound NPD9 from Novaled. A layer of this type simplifies hole injection in materials having a low HOMO, i.e. a large value of the HOMO.

All materials as are used in accordance with the prior art for the layers can generally be used in the further layers, and the person skilled in the art will be able to combine each of these materials with the materials according to the invention in an electronic device without inventive step.

The device is correspondingly structured (depending on the application), provided with contacts and finally hermetically sealed, since the lifetime of such devices is drastically shortened in the presence of water and/or air.

Preference is furthermore given to an organic electroluminescent device, characterised in that one or more layers are applied by means of a sublimation process, in which the materials are vapour-deposited in vacuum sublimation units at an initial pressure of usually less than $10^{-5}$ mbar, preferably less than $10^{-6}$ mbar. It is also possible for the initial pressure to be even lower or even higher, for example less than $10^{-7}$ mbar.

Preference is likewise given to an organic electroluminescent device, characterised in that one or more layers are applied by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, offset printing or nozzle printing, but particularly preferably LITI (light induced thermal imaging, thermal transfer printing) or ink-jet printing. Soluble compounds are necessary for this purpose, which are obtained, for example, through suitable substitution.

The organic electroluminescent device may also be produced as a hybrid system by applying one or more layers from solution and applying one or more other layers by vapour deposition. Thus, for example, it is possible to apply an emitting layer comprising a compound of the formula (1) and a matrix material from solution and to apply a hole-blocking layer and/or an electron-transport layer on top by vacuum vapour deposition.

These processes are generally known to the person skilled in the art and can be applied by him without problems to organic electroluminescent devices comprising compounds of the formula (1) or the preferred embodiments indicated above.

The electronic devices according to the invention, in particular organic electroluminescent devices, are distinguished over the prior art by one or more of the following surprising advantages:
1. The compounds according to the invention are very highly suitable for use in electronic devices, in particular in organic electroluminescent devices, where they result in very good properties.
2. Organic electroluminescent devices comprising compounds of the formula (1) as emitting materials have a very good lifetime.
3. Organic electroluminescent devices comprising compounds of the formula (1) as emitting materials have very good efficiency.

These advantages mentioned above are not accompanied by an impairment of the other electronic properties.

The invention is explained in greater detail by the following examples, without wishing to restrict it thereby. The person skilled in the art will be able to produce further electronic devices on the basis of the descriptions without inventive step and will thus be able to carry out the invention throughout the range claimed.

EXAMPLES

The following syntheses are carried out, unless indicated otherwise, in dried solvents under a protective-gas atmosphere. The metal complexes are additionally handled with exclusion of light or under yellow light. The solvents and reagents can be purchased, for example, from Sigma-AL-DRICH or ABCR. The respective numbers in square brackets or the numbers indicated for individual compounds relate to the CAS numbers of the compounds known from the literature.

A: Synthesis of the Synthones S:

Example S1

1,1,3,3-Tetramethylindane-5,6-diamine, [83721-95-3], S1

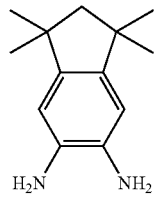

Variant A
A: 5,6-Dibromo-1,1,3,3-tetramethylindane, S1a

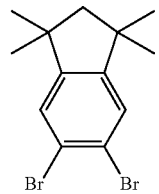

1.3 g of anhydrous iron(III) chloride and then, dropwise with exclusion of light, a mixture of 64.0 ml (1.25 mol) of bromine and 300 ml of dichloro-methane are added to a solution of 87.2 g (500 mmol) of 1,1,3,3-tetramethylindane [4834-33-7] in 2000 ml of dichloromethane at such a rate that the temperature does not exceed 25° C., if necessary with countercooling using a cold-water bath. The reaction mixture is stirred at room temperature for a further 16 h, 500 ml of saturated sodium sulfite solution are then added slowly, the aqueous phase is separated off, the organic phase is washed three times with 1000 ml of water each time, dried over sodium sulfate, filtered through a short silica-gel column, and the solvent is then stripped off. Finally, the solid is recrystallised once from a little (about 100 ml) ethanol. Yield: 121.2 g (365 mmol), 73%; purity: about 95% according to $^1$H-NMR.

B: 1,1,3,3-Tetramethylindane-5,6-diamine, S1
9.34 g (15 mmol) of rac-BINAP and then 3.36 g (15 mmol) of palladium(II) acetate are added to a mixture of 121.2 g (365 mmol) of 5,6-dibromo-1,1,3,3-tetramethylindane, 153.2 ml (913 mmol) of benzhydrylidenamine [1013-88-3], 96.1 g (1.0 mol) of sodium tert-butoxide and 1000 ml of toluene, and the mixture is subsequently heated under reflux for 16 h. After cooling, 500 ml of water are added, the organic phase is separated off, washed twice with 500 ml of saturated sodium chloride solution each time, the toluene is removed in a rotary evaporator, the residue is taken up in 500 ml of THF, 200 ml of 2 N hydrochloric acid are added, and the reaction mixture is heated under reflux for 16 h. The solvent is removed in vacuo, the residue is taken up in 1000 ml of ethyl acetate, the organic phase is washed with sodium hydrogencarbonate solution until pH=7 has been reached, the organic phase is dried over magnesium sulfate, the desiccant is filtered off, 500 g of silica gel are added to the filtrate, and the solvent is removed in vacuo. The loaded silica gel is placed on a silica-gel column (1500 g, slurried in n-heptane: ethyl acetate, 95:5 vv), firstly the benzophenone is eluted with n-heptane: ethyl acetate (95:5 vv), the eluent is then switched to ethyl acetate, and the product is eluted. Yield: 56.8 g (278 mmol), 76%; purity: about 95% according to $^1$H-NMR.

Variant B
A: 5,6-Dinitro-1,1,3,3-tetramethylindane, S1b

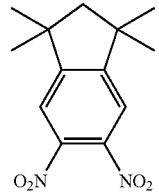

350 ml of 100% by weight nitric acid are slowly added dropwise to a vigorously stirred mixture, cooled to 0° C., of 87.2 g (500 mmol) of 1,1,3,3-tetramethylindane [4834-33-7] and 350 ml of 95% by weight sulfuric acid at such a rate that the temperature does not exceed +5° C. The reaction mixture is subsequently allowed to warm slowly to room temperature over the course of 2-3 h and is then poured into a vigorously stirred mixture of 6 kg of ice and 2 kg of water. The mixture is adjusted to pH=8-9 by addition of 40% by weight NaOH, extracted three times with 1000 ml of ethyl acetate each time, the combined organic phases are washed twice with 1000 ml of water each time, dried over magnesium sulfate, the ethyl acetate is then removed virtually completely in vacuo until crystallisation commences, and the crystallisation is completed by addition of 500 ml of heptane. The beige crystals obtained in this way are filtered off with suction and dried in vacuo. Yield: 121.6 g (460 mmol), 92%; purity: about 94% according to $^1$H-NMR, remainder about 4% of 4,6-dinitro-1,1,3,3-tetramethylindane. About 3% of 4,5-dinitro-1,1,3,3-tetramethylindane can be isolated from the mother liquor.

B: 1,1,3,3-Tetramethylindane-5,6-diamine, S1

126.9 g (480 mmol) of 5,6-dinitro-1,1,3,3-tetramethylindane, S16b, are hydrogenated in 1200 ml of ethanol on 10 g of palladium/charcoal at room temperature at a hydrogen pressure of 3 bar for 24 h. The reaction mixture is filtered through a Celite bed twice, the brown solid obtained after removal of the ethanol is distilled in a bulb tube (T about 160° C., p about $10^{-4}$ mbar). Yield: 90.3 g (442 mmol), 92%; purity: about 95% according to $^1$H-NMR.

1,1,3,3-Tetramethylindane-5,6-diamine dihydrochloride, S16×2HCl, can be obtained from S16 by dissolution in dichloromethane and introduction of gaseous HCl to saturation and subsequent removal of the dichloromethane.

The following compounds are prepared analogously:

| Ex. | Starting material | Product | Variant Yield Step A + B |
|---|---|---|---|
| S2 |  91324-94-6 |  S2 | A 63% B 78% |
| S3 | 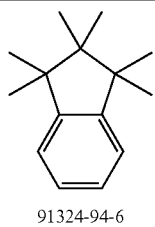 S1 | 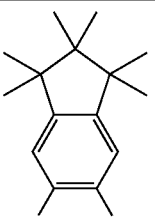 S3 | B 80% |
| S4 | 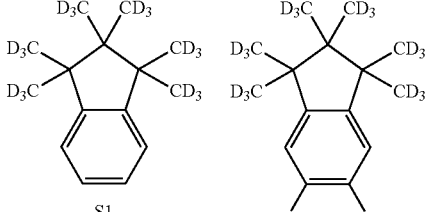 142076-41-3 | 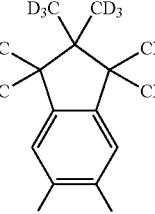 S4 | B 76% |
| S5 | 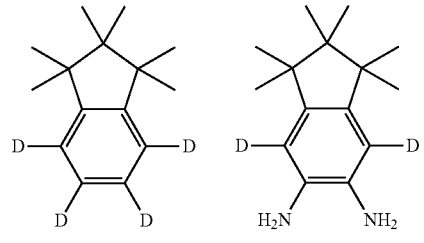 4486-29-7 | 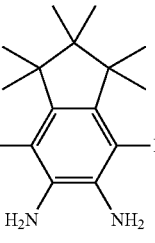 124639-03-8 S5 | B 71% |

Example S6

2-(5,5,7,7-Tetramethyl-1,5,6,7-tetrahydroindeno[5,6-d]-imidazol-2-yl]phenylamine, S6

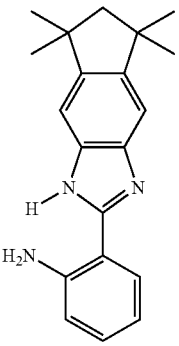 [SMILES: CC1(C)CC(C)(C)c2cc3[nH]c(-c4ccccc4N)nc3cc21]

Preparation analogous to Pandey, Rampal et al., Tetrahedron Letters, 53(28), 3550, 2012.

A solution of 20.4 g (100 mmol) of 1,1,3,3-tetramethylindane-5,6-diamine, S1 and 13.7 g (100 mmol) of 2-aminobenzoic acid [118-92-3] in 400 ml of methanol is heated at room temperature for 30 min. and then under reflux for 6 h, during which 200 ml of methanol are gradually distilled off. After slow cooling, the mixture is stirred at room temperature for a further 12 h, the crystals are filtered off with suction, washed with a little methanol and dried in vacuo. Yield: 25.0 g (82 mmol) 82%. Purity: 97% according to $^1$H-NMR.

2-(2-Hydroxyphenyl)benzimidazoles are obtained analogously to M. Al Messmary et al., Int. Arch. Appl. Science and Tech. 1(1), 84, 2011 in accordance with the above procedure, with methanol being replaced by glacial acetic acid.

The following compounds are prepared analogously:
| Ex. | Diamine | Carboxylic acid | Product | Yield |
|---|---|---|---|---|
| S7 | 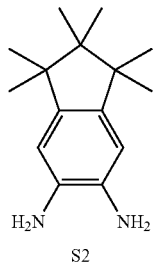<br>S2 | 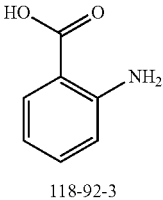<br>118-92-3 | 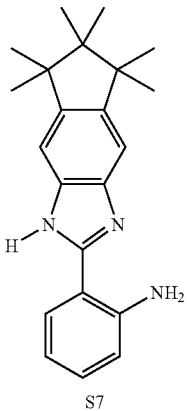<br>S7 | 79% |
| S8 | 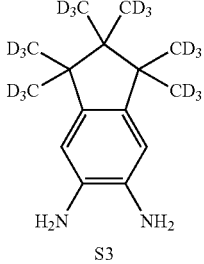<br>S3 | 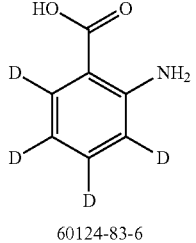 [SMILES: [2H]c1c([2H])c([2H])c(C(=O)O)c(N)c1[2H]]<br>60124-83-6 | 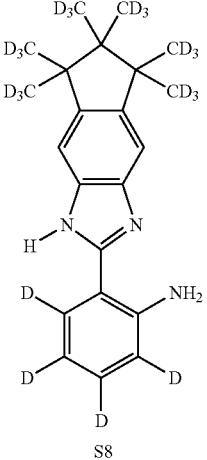 [SMILES: [2H]c1c([2H])c([2H])c(-c2nc3cc4c(cc3[nH]2)C(C([2H])([2H])[2H])(C([2H])([2H])[2H])C(C([2H])([2H])[2H])(C([2H])([2H])[2H])C4(C([2H])([2H])[2H])C([2H])([2H])[2H])c(N)c1[2H] ; "S8"]<br>S8 | 77% |
| S9 | 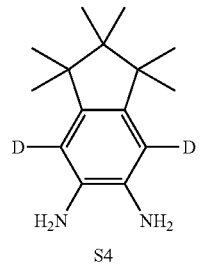<br>S4 | 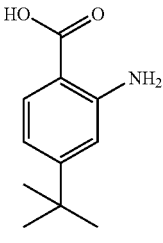<br>728945-64-0 | 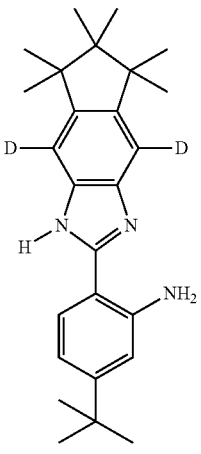<br>S9 | 80% |

-continued
| Ex. | Diamine | Carboxylic acid | Product | Yield |
|---|---|---|---|---|
| S10 | 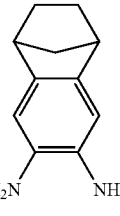<br>124639-03-8<br>S5 | 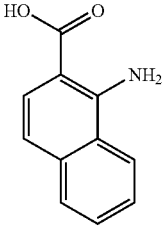<br>4919-43-1 | 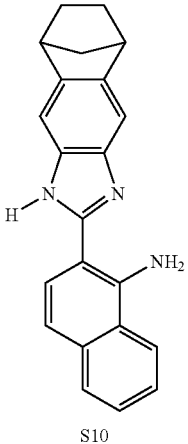<br>S10 | 73% |
| S11 | 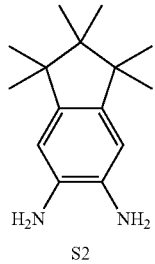<br>S2 | 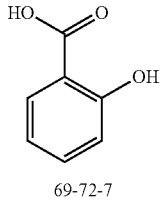<br>69-72-7 | 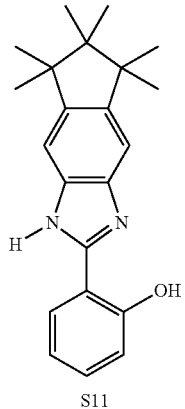 [SMILES: CC1(C)c2cc3nc(-c4ccccc4O)[nH]c3cc2C(C)(C)C1(C)C ; "S11"]<br>S11 | 57% |
| S12 | 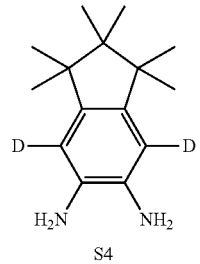<br>S4 | 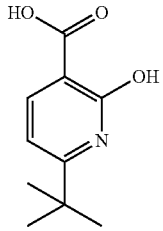 | 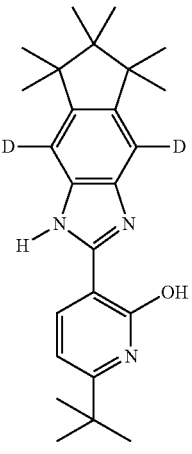<br>S12 | 54% |

B: Synthesis of the Ligands L:

Example L1

6,6-Dimethyl-5,6-dihydrobenzo[4,5]imidazo[1,2-c]-quinazoline

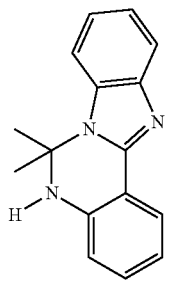 [SMILES: CC1(C)Nc2ccccc2-c2nc3ccccc3n21]

13.5 ml (110 mmol) of 2,2-dimethoxypropane and then 6.6 ml (110 mmol) of glacial acetic acid are added to a solution of 20.9 g (100 mmol) of 2-(2-aminophenyl)benzimidazole [5805-39-0] in 100 ml of acetone, and the mixture is stirred at room temperature for 16 h. The precipitated solid is filtered off with suction, washed once with 20 ml of acetone and dried in vacuo. Yield: 19.5 g (78 mmol) 78%. Purity: 99% according to $^1$H-NMR. The ligands obtained in this way are freed from boiling components and non-volatile secondary components by bulb-tube distillation or fractional sublimation (p approx. $10^{-4}$-$10^{-5}$ mbar, T approx. 160-240° C.). Compounds containing aliphatic radicals having more than 6 C atoms or those containing aralkyl groups having more than 9 C atoms are typically purified by chromatography and then dried in vacuo in order to remove low-boiling components. Purity according to $^1$H-NMR typically >99.5%.

The following compounds are prepared analogously:

| Ex. | Amine Alcohol | Ketal Solvent | Product | Yield |
|---|---|---|---|---|
| L2 | 29528-26-5 | | | 34% |
| L3 | 10173-54-3 | | | 75% |
| L4 | 1352336-60-7 | 931-94-2 / 120-92-3 | | 68% |

-continued

| Ex. | Amine Alcohol | Ketal Solvent | Product | Yield |
|---|---|---|---|---|
| L5 | S7 | | | 69% |
| L6 | S8 | | | 73% |
| L7 | S9 | 116143-54-5 Solvent THF | | 46% |

-continued

| Ex. | Amine Alcohol | Ketal Solvent | Product | Yield |
|---|---|---|---|---|
| L8 | S10 | (2,2-dimethoxypropane; acetone) | | 64% |
| L9 | S11 | (2,2-dimethoxypropane; acetone) | | 55% |
| L10 | S12 | (2,2-dimethoxypropane; acetone) | | 49% |

Example L11

5,6,6-Trimethyl-5,6-dihydrobenzo[4,5]imidazo[1,2-c]-quinazoline

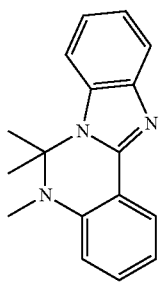 [SMILES: CN1c2ccccc2-c2nc3ccccc3n2C1(C)C]

A mixture of 24.9 g (100 mmol) of 6,6-dimethyl-5,6-dihydrobenzo[4,5]-imidazo[1,2-c]quinazoline, L1 and 11.5 g (120 mmol) of sodium tert-butoxide in 300 ml of THF is stirred at 60° C. for 30 min. After cooling to room temperature, 7.5 ml (120 mmol) of methyl iodide in 50 ml of THF are added dropwise, the mixture is then stirred at 60° C. for a further 4 h, the THF is removed in vacuo, the residue is taken up in 500 ml of ethyl acetate, the organic phase is washed twice with 300 ml of water each time, once with saturated sodium chloride solution, dried over magnesium sulfate, and the solvent is then removed in vacuo. Yield: 17.9 g (68 mmol) 68%. Purity: 99% according to $^1$H-NMR.

The ligands obtained in this way are freed from low-boiling components and non-volatile secondary components by bulb-tube distillation or fractional sublimation (p approx. $10^{-4}$-$10^{-5}$ mbar, T approx. 160-240° C.). Compounds containing aliphatic radicals having more than 6 C atoms, or those containing aralkyl groups having more than 9 C atoms, are typically purified by chromatography and then dried in vacuo in order to remove low-boiling components. Purity according to $^1$H-NMR typically >99.5%.

The following compounds are prepared analogously:

| Ex. | Amine | Alkylating agent | Product | Yield |
|---|---|---|---|---|
| L12 | L2 | H$_3$C—I | | 73% |
| L13 | L3 | H$_3$C—I | | 70% |
| L14 | L4 | n-Bu—I | | 48% |

-continued

| Ex. | Amine | Alkylating agent | Product | Yield |
|---|---|---|---|---|
| L15 | L5 | H₃C—I | | 67% |
| L16 | L6 | H₃C—I | | 70% |
| L17 | LL7 | H₃C—I | | 36% |

Example L18

6,6-Dimethyl-5-phenyl-5,6-dihydrobenzo[4,5]imidazo-[1,2-c]quinazoline

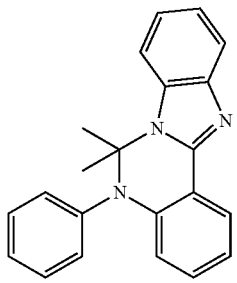 [SMILES: CC1(C)N(c2ccccc2)c2ccccc2-c2nc3ccccc3n21]

A mixture of 24.9 g (100 mmol) of 6,6-dimethyl-5,6-dihydrobenzo[4,5]-imidazo[1,2-c]quinazoline, L1, 11.2 ml (120 mmol) of fluorobenzene [462-06-6] and 11.5 g (120 mmol) of sodium tert-butoxide in dimethyl-acetamide is stirred at 160° C. for 30 h. After cooling to room temperature, 500 ml of ethyl acetate are added, the organic phase is washed five times with 300 ml of water each time, once with saturated sodium chloride solution, dried over magnesium sulfate, and the solvent is then removed in vacuo. The oily residue is distilled twice in a bulb tube (p approx. $10^{-4}$-$10^{-5}$ mbar, T approx. 200-220° C.). Yield: 15.3 g (47 mmol) 47%. Purity: 99.5% according to $^1$H-NMR.

The following compounds can be prepared analogously.

Example L21

6,6-Dimethyl-5-oxa-6a,11-diaza-6-silabenzo[a]fluorene

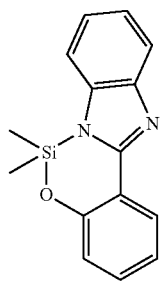 [SMILES: C[Si]1(C)Oc2ccccc2-c2nc3ccccc3n21]

A mixture of 12.8 ml (105 mmol) of dichlorodimethylsilane [75-78-5] and 50 ml of THF is added dropwise to a solution of 21.0 g (100 mmol) of 2-(2-hydroxyphenyl)benzimidazole [2963-66-8] in a mixture of 300 ml of THF and 30.5 ml (220 mmol) of triethylamine, and the mixture is stirred at room temperature for 16 h. The THF is removed in vacuo, the residue is taken up in 200 ml of cyclohexane, the triethylammonium chloride is filtered off with suction, and the cyclohexane is removed in vacuo. The oily residue is distilled twice in a bulb tube (p approx. $10^{-4}$-$10^{-5}$ mbar, T approx. 200-220° C.). Yield: 13.6 g (51 mmol) 51%. Purity: 99.5% according to $^1$H-NMR.

| Ex. | Amine | Fluoroaromatic compound | Product | Yield |
|-----|-------|-------------------------|---------|-------|
| L19 | L2 | 461-97-2 | | 43% |
| L20 | L5 | 462-06-6 | | 45% |

The following compounds are prepared analogously:

| Ex. | Imidazole | Electrophile | Product | Yield |
|---|---|---|---|---|
| L22 | 611-51-8 | 18395-90-9 | | 54% |
| L23 | S11 | | | 47% |
| L24 | S12 | | | 50% |
| L25 | 16367-94-5 | | | 39% |

-continued
| Ex. | Imidazole | Electrophile | Product | Yield |
|---|---|---|---|---|
| L26 | 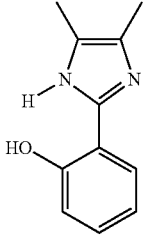 611-51-8 | 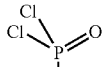 676-97-1 24 h at 60° C. | 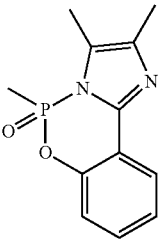 [SMILES: Cc1nc2n(c1C)P(C)(=O)Oc1ccccc1-2] | 44% |
| L27 | 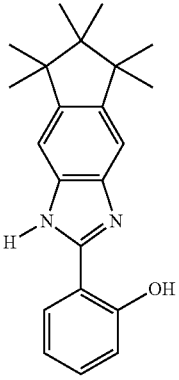 S11 | 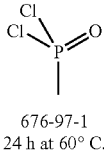 676-97-1 24 h at 60° C. | 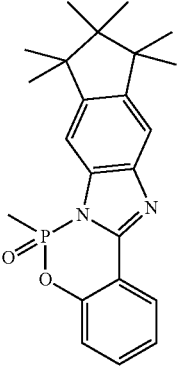 | 40% |
| L28 | 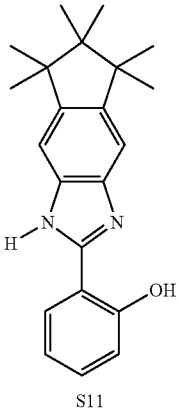 S11 | 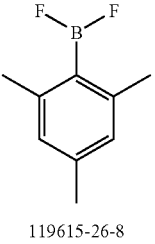 119615-26-8 | 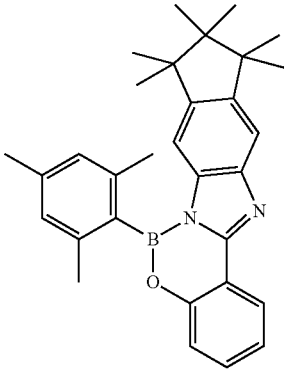 | 30% |
| L29 | 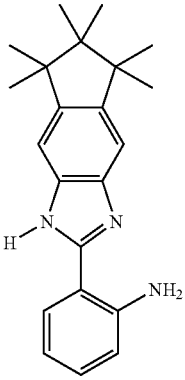 S7 | 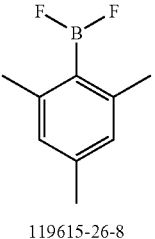 119615-26-8 | 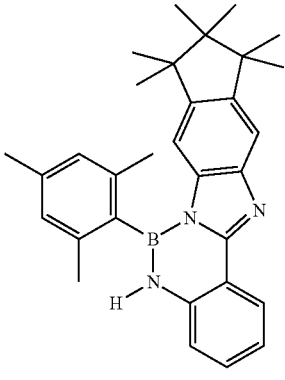 | 27% |

Example L30

5,5,6,6-Tetramethyl-5,6-dihydrobenzo[4,5]imidazo-[2,1a]isoquinoline

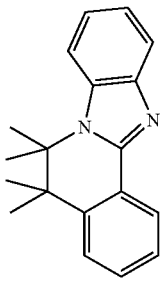 [SMILES: CC1(C)c2ccccc2-c2nc3ccccc3n2C1(C)C]

A mixture of 19.4 g (100 mmol) of 2-phenylbenzimidazole [716-79-0], 11.0 g (110 mmol) of 2,2,3,3-tetramethyloxirane [5076-20-0], 0.5 ml of boron trifluoride etherate and 50 ml of triethylene glycol dimethyl ether is heated at 180° C. in an autoclave for 12 h. After cooling, 300 ml of ethyl acetate are added to the reaction mixture, the mixture is washed five times with 200 ml of water each time, once with 200 ml of sat. sodium chloride solution, and the org. phase is dried over magnesium sulfate. The org. phase is freed from solvent, 300 ml of glacial acetic acid, 30 ml of acetic anhydride and 10 ml of conc. sulfuric acid are added, and the mixture is then stirred at 80° C. for 4 h. The acetic acid is removed in vacuo, the residue is taken up in 500 ml of dichloromethane, carefully rendered alkaline using 10% by weight NaOH solution with ice-cooling, the org. phase is separated off, washed once with 200 ml of water, once with 200 ml of sat. sodium chloride solution and dried over magnesium sulfate. The residue remaining after removal of the solvent is chromatographed on silica gel (ethyl acetate: MeOH 9:1) and then distilled twice in a bulb tube (p approx. $10^{-4}$-$10^{-5}$ mbar, T approx. 200-210° C.). Yield: 8.6 g (31 mmol) 31%. Purity: 99.5% according to $^1$H-NMR.

C: Synthesis of the Metal Complexes

1) Homoleptic Tris-facial Iridium Complexes:

Variant A: Trisacetylacetonatoiridium(III) as Iridium Starting Material

A mixture of 10 mmol of trisacetylacetonatoiridium(III) [15635-87-7] and 60 mmol of the ligand L and a glass-clad magnetic stirrer bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. In order to prevent sublimation of the ligands onto relatively cold parts of the ampoule, the entire ampoule must have the temperature indicated. Alternatively, the synthesis can be carried out in a stirred autoclave with glass insert. After cooling (NOTE: the ampoules are usually under pressure!), the ampoule is opened, the sinter cake is stirred for 3 h with 100 g of glass beads (diameter 3 mm) in 100 ml of a suspension medium (the suspension medium is selected so that the ligand is readily soluble, but the metal complex has low solubility therein, typical suspension media are methanol, ethanol, dichloromethane, acetone, THF, ethyl acetate, toluene, etc.) and mechanically digested in the process. The fine suspension is decanted off from the glass beads, the solid is filtered off with suction, rinsed with 50 ml of the suspension medium and dried in vacuo. The dry solid is placed on a 3-5 cm deep aluminium oxide bed (aluminium oxide, basic, activity grade 1) in a continuous hot extractor and then extracted with an extractant (initially introduced amount about 500 ml, the extractant is selected so that the complex is readily soluble therein at elevated temperature and has low solubility therein when cold, particularly suitable extractants are hydrocarbons, such as toluene, xylenes, mesitylene, naphthalene, o-dichloro-benzene, halogenated aliphatic hydrocarbons are generally unsuitable since they may halogenate or decompose the complexes). When the extraction is complete, the extractant is evaporated to about 100 ml in vacuo. Metal complexes which have excessively good solubility in the extractant are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot extraction step is repeated, omitting the aluminium oxide bed from the 2nd extraction. When a purity of 99.5-99.9% has been reached, the metal complex is heated or sublimed. The heating is carried out in a high vacuum (p about $10^{-6}$ mbar) in the temperature range from about 200-300° C. The sublimation is carried out in a high vacuum (p about $10^{-6}$ mbar) in the temperature range from about 300-400° C., with the sublimation preferably being carried out in the form of a fractional sublimation. If ligands in point group C1 are employed in the form of a racemic mixture, the derived fac-metal complexes are produced in the form of a diastereomer mixture. The enantiomer pair Λ,Δ in point group C3 generally has significantly lower solubility in the extractant than that in point group C1, which is consequently enriched in the mother liquor. Separation of the diastereomers by this method is frequently possible. In addition, the diastereomers can also be separated by chromatography. If ligands in point group C1 are employed in enantiomerically pure form, the enantiomer pair Λ,Δ in point group C3 is formed.

Variant B: Tris-(2,2,6,6-tetramethyl-3,5-heptanedionato)iridium(III) as Iridium Starting Material Procedure analogous to variant A, using 10 mmol of tris(2,2,6,6-tetra-methyl-3,5-heptanedionato)iridium [99581-86-9] instead of 10 mmol of tris-acetylacetonatoiridium(III) [15635-87-7]. The use of this starting material is advantageous since the purity of the crude products obtained is frequently better than in the case of variant A. In addition, the build-up of pressure in the ampoule is frequently not as pronounced.

| Ex. | Ligand L | Ir complex Diastereomer | Variant Reaction temp./ reaction time Suspension medium Extractant | Yield |
|---|---|---|---|---|
| Ir(L2)$_3$ | L2 | Ir(L2)$_3$ | A 230° C./60 h DCM Mesitylene | 24% |
| Ir(L9)$_3$ | L9 | Ir(L9)$_3$ | A 230° C./60 h DCM Mesitylene | 21% |
| Ir(L12)$_3$ | L12 | Ir(L12)$_3$ | B 240° C./80 h DCM Mesitylene | 25% |
| Ir(L15)$_3$ | L15 | Ir(L15)$_3$ | B 240° C./80 h Acetone Mesitylene | 23% |

-continued

| Ex. | Ligand L | Ir complex Diastereomer | Variant Reaction temp./reaction time Suspension medium Extractant | Yield |
|---|---|---|---|---|
| Ir(L16)₃ | L16 | Ir(L16)₃ | B 250° C./80 h Acetone Mesitylene | 21% |
| Ir(L20)₃ | L20 | Ir(L20)₃ | B 250° C./80 h Acetone Mesitylene | 22% |
| Ir(L24)₃ | L24 | Ir(L24)₃ | B 250° C./100 h Acetone Mesitylene | 18% |

-continued

| Ex. | Ligand L | Ir complex Diastereomer | Variant Reaction temp./reaction time Suspension medium Extractant | Yield |
|---|---|---|---|---|
| Ir(L27)₃ | L27 | Ir(L27)₃ | B 230° C./100 h THF Mesitylene | 21% |
| Ir(L28)₃ | L28 | | A 260° C./30 h THF Toluene | 15% |
| Ir(L29)₃ | L29 | | A 260° C./30 h THF Toluene | 13% |
| Ir(L30)₃ | L30 | | A 255° C./60 h EtOH Toluene | 24% |

2) Heteroleptic Iridium Complexes:

Variant A:

Step 1:

A mixture of 10 mmol of sodium bisacetylacetonatodichloroiridate(III) [770720-50-8] and 24 mmol of ligand L and a glass-clad magnetic stirrer bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated (the suspension medium is selected so that the ligand is readily soluble, but the chloro dimer of the formula $[Ir(L)_2Cl]_2$ has low solubility therein, typical suspension media are dichloromethane, acetone, ethyl acetate, toluene, etc.) and mechanically digested at the same time. The fine suspension is decanted off from the glass beads, the solid $(Ir(L)_2Cl)_2$ which still contains about 2 eq. of NaCl, referred to below as the crude chloro dimer) is filtered off with suction and dried in vacuo.

Step 2:

The crude chloro dimer of the formula $[Ir(L)_2Cl]_2$ obtained in this way is suspended in a mixture of 75 ml of 2-ethoxyethanol and 25 ml of water, 13 mmol of the co-ligand CL or the co-ligand compound CL and 15 mmol of sodium carbonate are added. After 20 h under reflux, a further 75 ml of water are added dropwise, after cooling the solid is filtered off with suction, washed three times with 50 ml of water each time and three times with 50 ml of methanol each time and dried in vacuo. The dry solid is placed on an aluminium oxide bed (aluminium oxide, basic activity grade 1) with a depth of 3-5 cm in a continuous hot extractor and then extracted with the extraction medium indicated (initially introduced amount about 500 ml, the extractant is selected so that the complex is readily soluble therein at elevated temperature and has low solubility therein when cold, particularly suitable extractants are hydrocarbons, such as toluene, xylenes, mesitylene, naphthalene, o-dichlorobenzene; halogenated aliphatic hydrocarbons are generally unsuitable since they may halogenate or decompose the complexes). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. Besides the hot extraction method for purification, the purification can also be carried out by chromatography on silica gel or aluminium oxide. The heating is carried out in the temperature range from about 200-300° C. in a high vacuum (p about $10^{-6}$ mbar). The sublimation is carried out in the temperature range from about 300-400° C. in a high vacuum (p about $10^{-6}$ mbar), where the sublimation is preferably carried out in the form of a fractional sublimation.

| Ex. | Ligand L | Co-ligand CL | Ir complex Step 1: reaction temp./ reaction time/ suspension medium Step 2: extractant | Yield |
|---|---|---|---|---|
| Ir(L10)$_2$(CL1) | L10 | 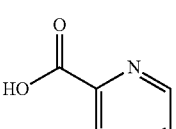<br>98-98-6<br>CL1 | 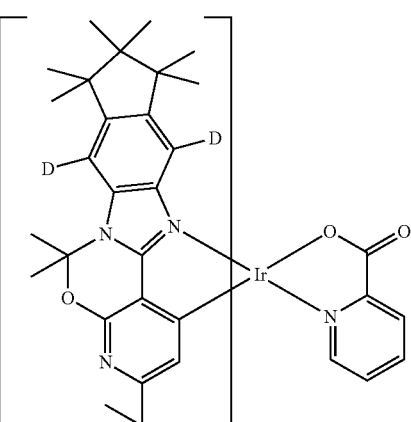<br>240° C./80 h/<br>acetone/mesitylene | 27% |

-continued

| Ex. | Ligand L | Co-ligand CL | Ir complex Step 1: reaction temp./reaction time/suspension medium Step 2: extractant | Yield |
|---|---|---|---|---|
| Ir(L11)₂(CL2) | L11 | 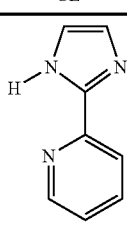<br>18653-75-3<br>CL2 | 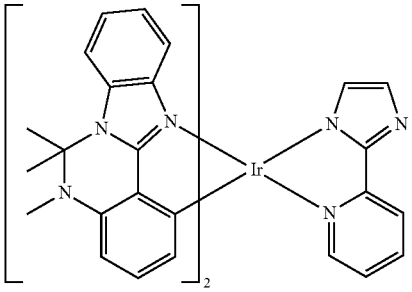<br>240° C./80 h/<br>acetone/mesitylene | 24% |
| Ir(L17)₂(CL3) | L17 | 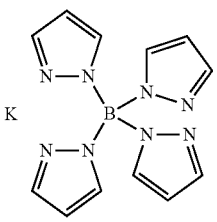<br>14782-58-2<br>CL3 | 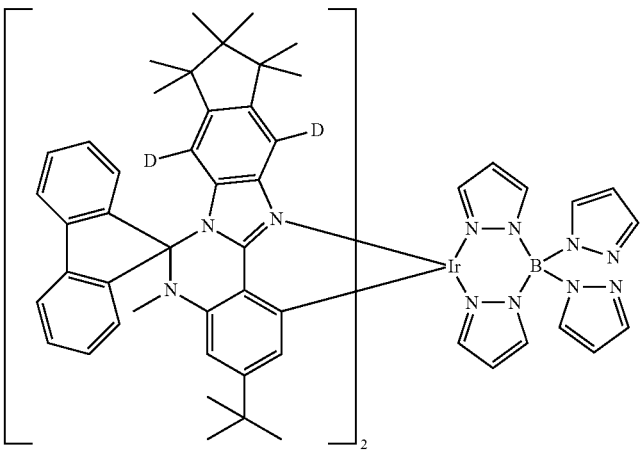<br>240° C./80 h/<br>acetone/mesitylene | 20% |
| Ir(L18)₂(CL4) | L18 | 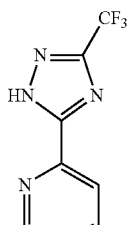<br>219508-27-7<br>CL4 | 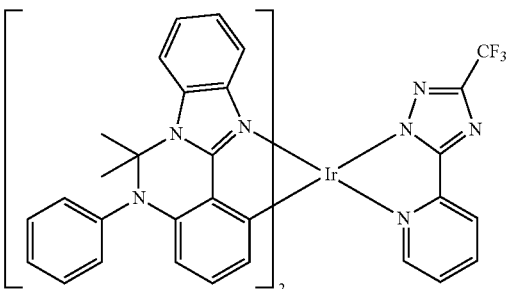<br>240° C./80 h/<br>acetone/mesitylene | 23% |

Variant B:

Step 1:

See variant A, step 1.

Step 2:

The crude chloro dimer of the formula $[Ir(L)_2Cl]_2$ obtained in this way is suspended in 1000 ml of dichloromethane and 150 ml of ethanol, 20 mmol of silver(I) trifluoromethanesulfonate are added to the suspension, and the mixture is stirred at room temperature for 24 h. The precipitated solid (AgCl) is filtered off with suction via a short Celite bed, and the filtrate is evaporated to dryness in vacuo. The solid obtained in this way is taken up in 100 ml of ethylene glycol, 20 mmol of co-ligand CL are added, and the mixture is then stirred at 130° C. for 30 h. After cooling, the solid is filtered off with suction, washed twice with 50 ml of ethanol each time and dried in vacuo. Hot extraction and sublimation as in variant A.

| Ex. | Ligand L | Co-ligand CL | Ir complex Step 1: reaction temp./reaction time/suspension medium Step 2: extractant | Yield |
|---|---|---|---|---|
| Ir(L13)₂(CL5) | L13 | 914306-48-2 CL5 | 230° C./80 h/ acetone/xylene | 26% |
| Ir(L14)₂(CL5) | L14 | CL5 | 230° C./80 h/ acetone/xylene | 29% |
| Ir(L19)₂(CL6) | L19 | 39696-58-7 CL6 | 230° C./80 h/ acetone/xylene | 24% |

-continued

| Ex. | Ligand L | Co-ligand CL | Ir complex Step 1: reaction temp./reaction time/suspension medium Step 2: extractant | Yield |
|---|---|---|---|---|
| Ir(L21)₂(CL6) | L21 | CL6 | 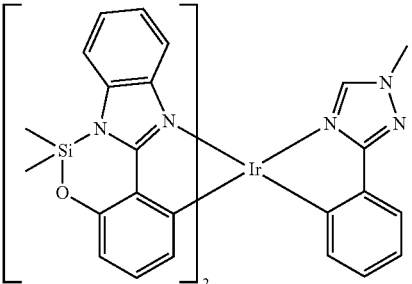<br>230° C./80 h/<br>acetone/xylene | 24% |
| Ir(L23)₂(CL6) | L23 | CL6 | 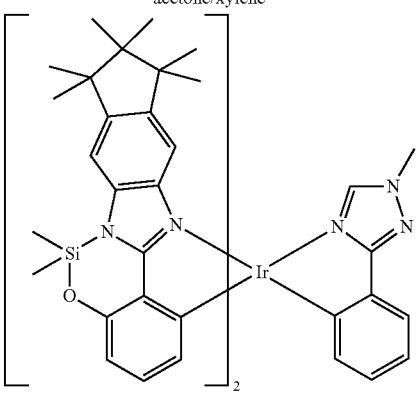<br>230° C./80 h/<br>acetone/xylene | 22% |
| Ir(L26)₂(CL6) | L26 | CL6 | 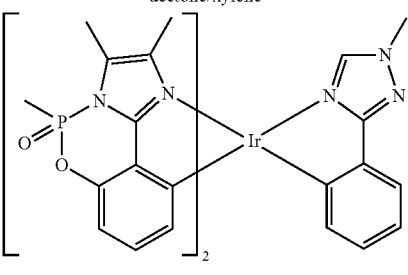<br>220° C./80 h/<br>acetone/xylene | 17% |

Heteroleptic Platinum Complexes:

A mixture of 10 mmol of platinum(II) chloride and 12 mmol of ligand L and a glass-clad magnetic stirre bar are melted into a thick-walled 50 ml glass ampoule in vacuo ($10^{-5}$ mbar). The ampoule is heated at the temperature indicated for the time indicated, during which the molten mixture is stirred with the aid of a magnetic stirrer. After cooling—NOTE: the ampoules are usually under pressure!—the ampoule is opened, the sinter cake is stirred for 3 h with 100 g of glass beads (diameter 3 mm) in 100 ml of the suspension medium indicated (the suspension medium is selected so that the ligand is readily soluble, but the chloro dimer of the formula [Ir(L)₂Cl]₂ has low solubility therein, typical suspension media are dichloromethane, acetone, ethyl acetate, toluene, etc.) and mechanically digested at the same time. The fine suspension is decanted off from the glass beads, the solid is filtered off with suction and dried in vacuo. The crude chloro dimer of the formula [Pt(L)Cl]₂ obtained in this way is suspended in a mixture of 60 ml of 2-ethoxyethanol and 20 ml of water, and 20 mmol of co-ligand CL or co-ligand compound CL and 20 mmol of sodium carbonate are added. After 20 h under reflux, a further 100 ml of water are added dropwise, after cooling the solid is filtered off with suction, washed three times with 50 ml of water each time and three times with 50 ml of methanol each time and dried in vacuo. The solid obtained in this way is placed on a Celite bed with a depth of 3-5 cm in a hot extractor and then extracted with the extraction medium indicated (initially introduced amount about 500 ml). When the extraction is complete, the extraction medium is evaporated to about 100 ml in vacuo. Metal complexes which have excessively good solubility in the extraction medium are brought to crystallisation by dropwise addition of 200 ml of methanol. The solid of the suspensions obtained in this way is filtered off with suction, washed once with about 50 ml of methanol and dried. After drying, the purity of the metal complex is determined by means of NMR and/or HPLC. If the purity is below 99.5%, the hot-extraction step is repeated, if a purity of 99.5-99.9% has been reached, the metal complex is heated or sublimed. The heating is carried out in the temperature range from about 200-300° C. in a high vacuum (p about $10^{-6}$ mbar). The sublimation is carried out in the temperature range from about 250-350° C. in a high vacuum (p about $10^{-6}$ mbar), where the sublimation is preferably carried out in the form of a fractional sublimation.

sition in a vacuum chamber. The emission layer here always consists of at least one matrix material (host material) and an emitting dopant (emitter), which is admixed with the matrix material or matrix materials in a certain proportion by volume by co-evaporation. An expression such as M3:M2:Ir(L1)$_3$ (55%:35%:10%) here means that material M3 is present in the layer in a proportion by volume of 55%, M2 is present in the layer in a proportion of 35% and Ir(L1)$_3$ is present in the layer in a proportion of 10%. Analogously, the electron-transport layer may also consist of a mixture of two materials. The precise structure of the OLEDs is shown in Table 1. The materials used for the production of the OLEDs are shown in Table 6.

The OLEDs are characterised by standard methods. For this purpose, the electroluminescence spectra, the current efficiency (measured in cd/A) and the voltage (measured at 1000 cd/m$^2$ in V) are determined from current/voltage/luminance characteristic lines (IUL characteristic lines). For selected experiments, the lifetime is determined. The lifetime is defined as the time after which the luminous density has dropped to a certain proportion from a certain initial luminous density. The expression LT50 means that the lifetime given is the time at which the luminous density has dropped to 50% of the initial luminous density, i.e. from, for example, 1000 cd/m$^2$ to 500 cd/m$^2$. Depending on the emission colour, different initial luminances were selected. The values for the lifetime can be converted to a figure for other initial luminous densities with the aid of conversion formulae known to the person skilled in the art. The lifetime for an initial luminous density of 1000 cd/m$^2$ is a usual figure here.

| Ex. | Ligand L | Co-ligand CL | Pt complex | Yield |
|---|---|---|---|---|
| Pt(L22)(CL7) | L22 | CL7 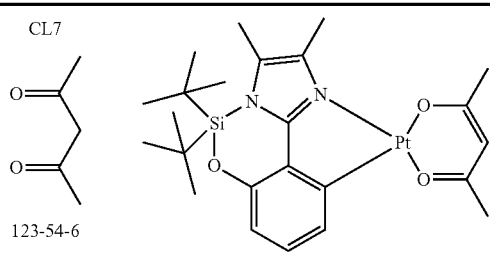 123-54-6 | 230° C./60 h/ acetone/xylene | 21% |
| Pt(L25)(CL2) | L25 | CL8 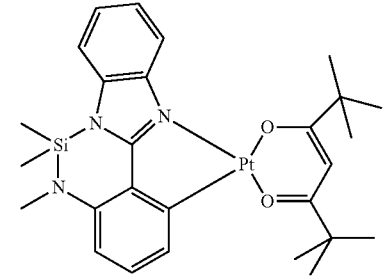 1118-71-4 | 220° C./60 h/ THF/xylene | 23% |

Production of the OLEDs
1) Vacuum-Processed Devices:

OLEDs according to the invention and OLEDs in accordance with the prior art are produced by a general process in accordance with WO 2004/058911, which is adapted to the circumstances described here (layer-thickness variation, materials used).

The results for various OLEDs are presented in the following examples. Glass plates with structured ITO (indium tin oxide) form the substrates to which the OLEDs are applied. The OLEDs have in principle the following layer structure: substrate/hole-transport layer 1 (HTL1) consisting of HTM doped with 3% of NDP-9 (commercially available from Novaled), 20 nm/hole-transport layer 2 (HTL2)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm Firstly, vacuum-processed OLEDs are described. For this purpose, all materials are applied by thermal vapour depo- Use of Compounds According to the Invention as Emitter Materials in Phosphorescent OLEDs The compounds according to the invention can be employed, inter alia, as phosphorescent emitter materials in the emission layer in OLEDs. The results for the OLEDs are summarised in Table 2.

TABLE 1

Structure of the OLEDs

| Ex. | HTL2 Thickness | EBL Thickness | EML Thickness | HBL Thickness | ETL Thickness |
|---|---|---|---|---|---|
| D-Ir(L2)$_3$ | HTM 180 nm | EBM 20 nm | M1:M4:Ir(L2)$_3$ (65%:30%:5%) 25 nm | HBM 10 nm | ETM1:ETM2 (50%:50%) 20 nm |
| D-Ir(L9)$_3$ | HTM 180 nm | EBM 20 nm | M1:M3:Ir(L9)$_3$ (65%:30%:5%) 25 nm | HBM 10 nm | ETM1:ETM2 (50%:50%) 20 nm |
| D-Ir(L12)$_3$ | HTM 180 nm | EBM 20 nm | M1:M4:Ir(L12)$_3$ (65%:30%:5%) 25 nm | HBM 10 nm | ETM1:ETM2 (50%:50%) 20 nm |
| D-Ir(L15)$_3$ | HTM 180 nm | EBM 20 nm | M1:M4:Ir(L15)$_3$ (65%:30%:5%) 25 nm | HBM 10 nm | ETM1:ETM2 (50%:50%) 20 nm |
| D-Ir(L16)$_3$ | HTM 180 nm | EBM 20 nm | M1:M3:Ir(L16)$_3$ (55%:40%:5%) 25 nm | HBM 10 nm | ETM1:ETM2 (50%:50%) 20 nm |
| D-Ir(L24)$_3$ | HTM 180 nm | EBM 20 nm | M1:M4:Ir(L24)$_3$ (65%:30%:5%) 25 nm | HBM 10 nm | ETM1:ETM2 (50%:50%) 20 nm |
| D-Ir(L27)$_3$ | HTM 180 nm | EBM 20 nm | M1:M4:Ir(L27)$_3$ (65%:30%:5%) 25 nm | HBM 10 nm | ETM1:ETM2 (50%:50%) 20 nm |
| D-Ir(L10)$_2$(CL1) | HTM 180 nm | EBM 20 nm | M1:M3:Ir(L10)$_2$(CL1) (65%:30%:5%) 25 nm | HBM 10 nm | ETM1:ETM2 (50%:50%) 20 nm |
| D-Ir(L11)$_2$(CL2) | HTM 180 nm | EBM 20 nm | M1:M4:Ir(L11)$_2$(CL2) (65%:30%:5%) 25 nm | HBM 10 nm | ETM1:ETM2 (50%:50%) 20 nm |
| D-Ir(L18)$_2$(CL4) | HTM 180 nm | EBM 20 nm | M1:M4:Ir(L18)$_2$(CL4) (75%:20%:5%) 25 nm | HBM 10 nm | ETM1:ETM2 (50%:50%) 20 nm |
| D-Ir(L13)$_2$(CL5) | HTM 180 nm | EBM 20 nm | M1:M4:Ir(L230)$_3$ (65%:30%:5%) 25 nm | HBM 10 nm | ETM1:ETM2 (50%:50%) 20 nm |
| D-Ir(L19)$_2$(CL6) | HTM 180 nm | EBM 20 nm | M1:M4:Ir(L19)$_2$(CL6) (65%:30%:5%) 25 nm | HBM 10 nm | ETM1:ETM2 (50%:50%) 20 nm |
| D-Ir(L21)$_2$(CL6) | HTM 180 nm | EBM 20 nm | M1:M4:Ir(L21)$_2$(CL6) (65%:30%:5%) 25 nm | HBM 10 nm | ETM1:ETM2 (50%:50%) 20 nm |
| D-Ir(L23)$_2$(CL6) | HTM 180 nm | EBM 20 nm | M1:M4:Ir(L23)$_2$(CL6) (65%:30%:5%) 25 nm | HBM 10 nm | ETM1:ETM2 (50%:50%) 20 nm |
| D-Ir(L26)$_2$(CL6) | HTM 180 nm | EBM 20 nm | M1:M4:Ir(L26)$_2$(CL6) (75%:20%:5%) 25 nm | HBM 10 nm | ETM1:ETM2 (50%:50%) 20 nm |
| D-Pt(L22)(CL7) | HTM 180 nm | EBM 20 nm | M1:M4:Pt(L22)(CL7) (75%:20%:5%) 25 nm | HBM 10 nm | ETM1:ETM2 (50%:50%) 20 nm |
| D-Pt(L25)(CL2) | HTM 180 nm | EBM 20 nm | M1:M4:Pt(L25)(CL2) (75%:20%:5%) 25 nm | HBM 10 nm | ETM1:ETM2 (50%:50%) 20 nm |

TABLE 2

Results of the vacuum-processed OLEDs

| Ex. | EQE (%) 1000 cd/m$^2$ | Voltage (V) 1000 cd/m$^2$ | CIE x/y 1000 cd/m$^2$ | LT50 (h) 1000 cd/m$^2$ |
|---|---|---|---|---|
| D-Ir(L2)$_3$ | 9.4 | 4.6 | 0.16/0.24 | — |
| D-Ir(L9)$_3$ | 14.3 | 4.1 | 0.15/0.36 | 600 |
| D-Ir(L12)$_3$ | 9.9 | 4.5 | 0.16/0.24 | 250 |
| D-Ir(L15)$_3$ | 16.4 | 4.3 | 0.15/0.38 | 700 |
| D-Ir(L16)$_3$ | 16.0 | 4.2 | 0.15/0.38 | — |
| D-Ir(L24)$_3$ | 15.5 | 4.1 | 0.15/0.30 | — |
| D-Ir(L27)$_3$ | 9.7 | 4.3 | 0.15/0.35 | — |
| D-Ir(L10)$_2$(CL1) | 15.5 | 4.1 | 0.15/0.27 | — |
| D-Ir(L11)$_2$(CL2) | 14.1 | 4.2 | 0.15/0.34 | 500 |
| D-Ir(L18)$_2$(CL4) | 9.9 | 4.6 | 0.17/0.31 | — |
| D-Ir(L13)$_2$(CL5) | 13.8 | 4.3 | 0.15/0.33 | — |
| D-Ir(L19)$_2$(CL6) | 12.9 | 4.4 | 0.16/0.26 | — |
| D-Ir(L21)$_2$(CL6) | 10.5 | 4.3 | 0.16/0.34 | — |
| D-Ir(L23)$_2$(CL6) | 15.5 | 4.3 | 0.16/0.35 | 600 |
| D-Ir(L26)$_2$(CL6) | 4.4 | 4.9 | 0.15/0.22 | — |
| D-Pt(L22)(CL7) | 6.7 | 4.8 | 0.15/0.25 | — |
| D-Pt(L25)(CL2) | 8.7 | 4.4 | 0.15/0.35 | — |

2) Solution-Processed Devices:

A: From Soluble Functional Materials

The complexes according to the invention can also be processed from solution, where they result in OLEDs which are significantly simpler as far as the process is concerned, compared with the vacuum-processed OLEDs, with nevertheless good properties. The production of components of this type is based on the production of polymeric light-emitting diodes (PLEDs), which has already been described many times in the literature (for example in WO 2004/037887).

The structure is composed of substrate/ITO/PEDOT (80 nm)/interlayer (80 nm)/emission layer (80 nm)/cathode. To this end, use is made of substrates from Technoprint (soda-lime glass), to which the ITO structure (indium tin oxide, a transparent, conductive anode) is applied. The substrates are cleaned with DI water and a detergent (Deconex 15 PF) in a clean room and then activated by a UV/ozone plasma treatment. An 80 nm layer of PEDOT (PEDOT is a polythiophene derivative (Baytron P VAI 4083sp.) from H. C. Starck, Goslar, which is supplied as an aqueous dispersion) is then applied as buffer layer by spin coating, likewise in the clean room. The spin rate required depends on the degree of dilution and the specific spin coater geometry (typically for 80 nm: 4500 rpm). In order to remove residual water from the layer, the substrates are dried by heating on a hotplate at 180° C. for 10 minutes. The interlayer used serves for hole injection, in this case HIL-012 from Merck is used. The interlayer may alternatively also be replaced by one or more layers, which merely have to satisfy the condition of not being detached again by the subsequent processing step of EML deposition from solution. In order to produce the emission layer, the emitters according to the invention are dissolved in toluene together with the matrix materials. The typical solids content of such solutions is between 16 and 25 g/l if, as here, the typical layer thickness of 80 nm for a device is to be achieved by means of spin coating. The solution-processed devices comprise an emission layer comprising (polystyrene):M5:M6:Ir(L)$_3$ (25%:25%:40%:10%). The emission layer is applied by spin coating in an inert-gas atmosphere, in the present case argon, and dried by heating at 130° C. for 30 min. Finally, a cathode is applied by vapour deposition from barium (5 nm) and then aluminium (100 nm) (high-purity metals from Aldrich, particularly barium 99.99% (Order No. 474711); vapour-deposition equipment from Lesker, inter alia, typical vapour-deposition pressure 5×10$^{-6}$ mbar). Optionally, firstly a hole-blocking layer and then an electron-transport layer and only then the cathode (for example Al or LiF/Al) can be applied by vacuum vapour deposition. In order to protect the device against air and atmospheric moisture, the device is finally encapsulated and then characterised. The OLED examples given have not yet been optimised, Table 3 summarises the data obtained.

TABLE 3

Resuts with solution-processed materials

| Ex. | Complex | EQE (%) 1000 cd/m$^2$ | Voltage (V) 1000 cd/m$^2$ | CIE x/y 1000 cd/m$^2$ |
|---|---|---|---|---|
| D-Ir(L20)$_3$ | Ir(L20)$_3$ | 12.6 | 4.7 | 0.16/0.36 |
| D-Ir(L28)$_3$ | Ir(L28)$_3$ | 9.6 | 4.5 | 0.15/0.32 |
| D-Ir(L30)$_3$ | Ir(L30)$_3$ | 13.8 | 4.8 | 0.16/0.33 |
| D-Ir(L17)$_2$(CL3) | Ir(L17)$_2$(CL3) | 8.7 | 5.0 | 0.17/0.35 |
| D-Ir(L14)$_2$(CL5) | Ir(L14)$_2$(CL5) | 9.3 | 4.9 | 0.16/0.27 |

3) White-Emitting OLEDs

A white-emitting OLED having the following layer structure is produced in accordance with the general processes from 1):

TABLE 4

Structure of the white OLEDs

| Ex. | HTL2 Thickness | EML Red Thickness | EML Blue Thickness | EML Green Thickness | HBL Thickness | ETL Thickness |
|---|---|---|---|---|---|---|
| D-W1 | HTM 230 nm | EBM:Ir-R (97%:3%) 9 nm | M1:M3:Ir(L9)$_3$ (45%:50%:5%) 8 nm | M3:Ir-G (90%:10%) 7 nm | M3 10 nm | ETM1:ETM2 (50%:50%) 30 nm |

TABLE 5

Device results

| Ex. | EQE (%) 1000 cd/m$^2$ | Voltage (V) 1000 cd/m$^2$ | CIE x/y 1000 cd/m$^2$ CRI | LT50 (h) 1000 cd/m$^2$ |
|---|---|---|---|---|
| D-W1 | 13.0 | 6.6 | 0.45/0.4380 | 1500 |

TABLE 6

Structural formulae of the materials used

HTM

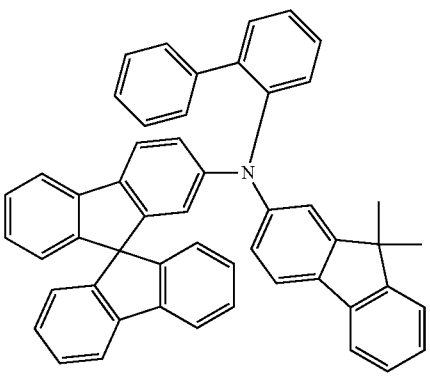 [SMILES: CC1(C)c2ccccc2-c2ccc(N(c3ccc4c(c3)C3(c5ccccc5-c5ccccc53)c3ccccc3-4)c3ccccc3-c3ccccc3)cc21]

TABLE 6-continued
Structural formulae of the materials used
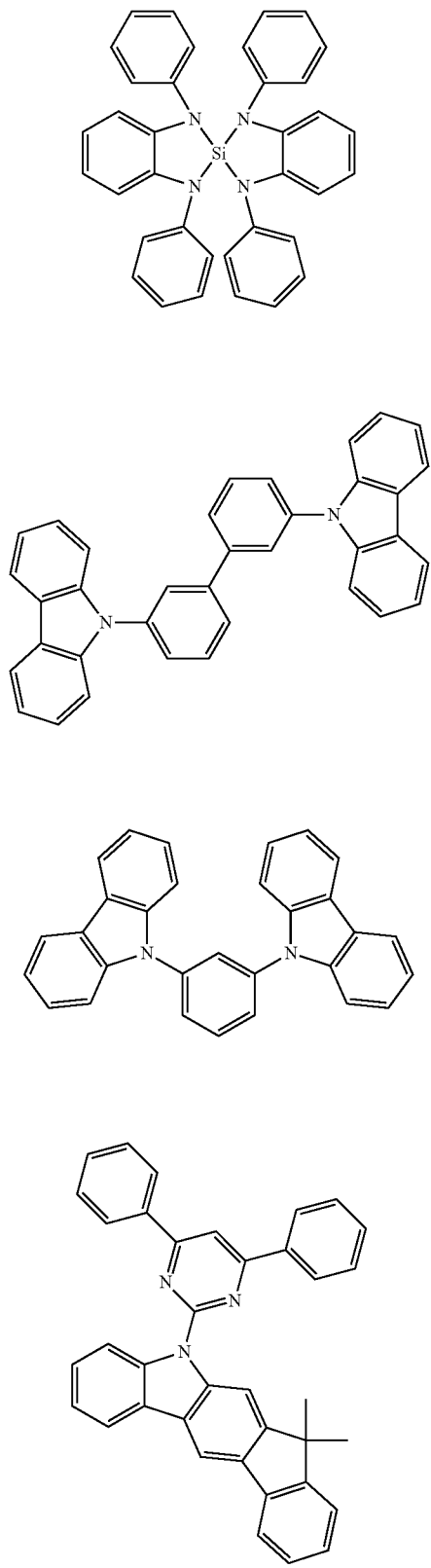
EBM
M1
M2
M3
TABLE 6-continued
Structural formulae of the materials used
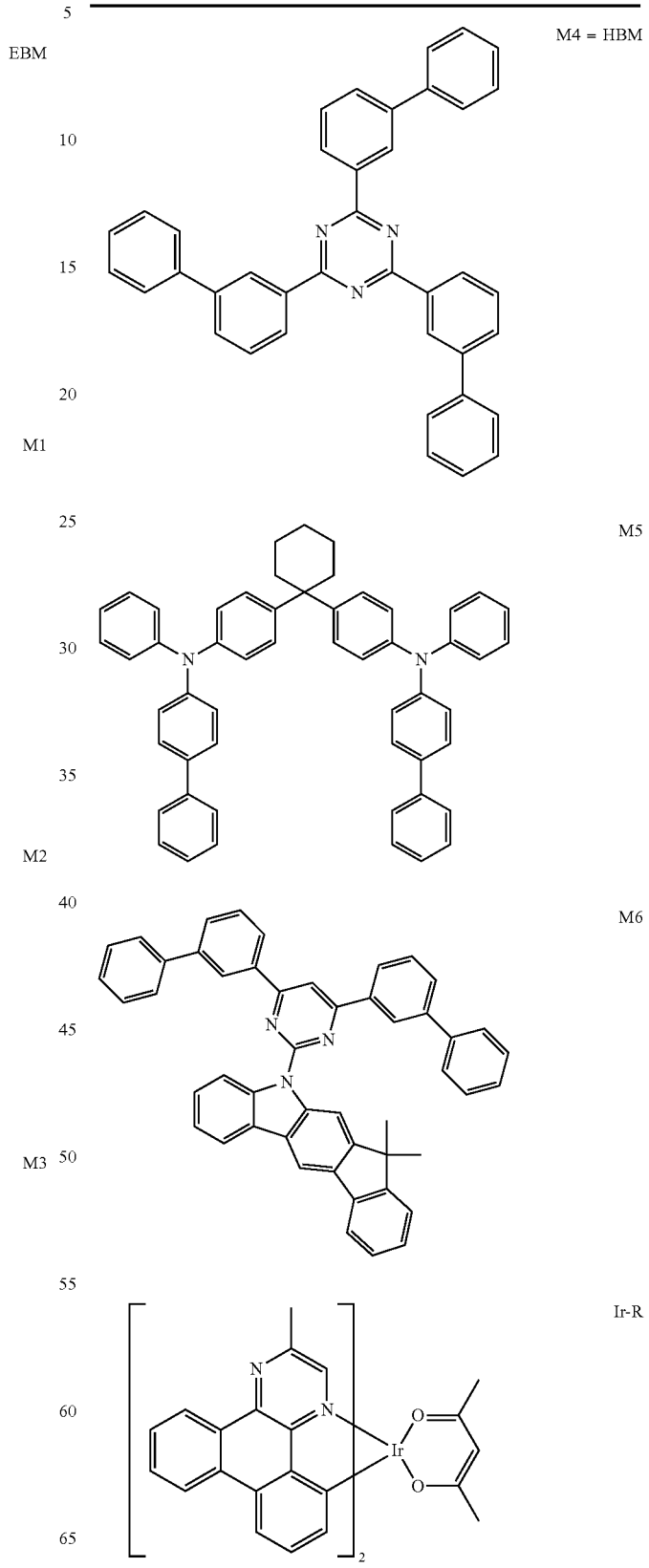
M4 = HBM
M5
M6
Ir-R TABLE 6-continued Structural formulae of the materials used

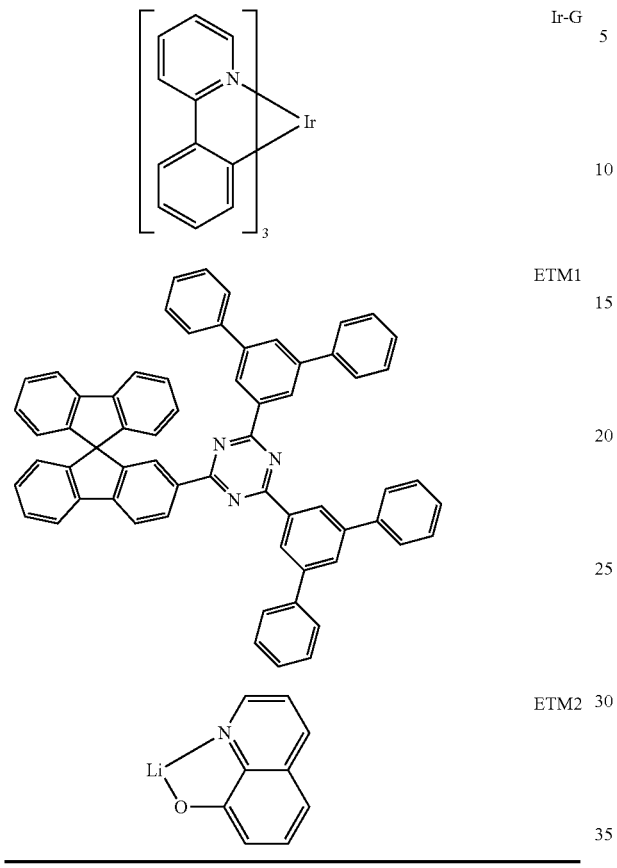

Ir-G

ETM1

ETM2

The invention claimed is:

1. A compound of formula (1):

$$M(L)_n(L')_m \quad (1)$$

comprising a moiety $M(L)_n$ of formula (2) or formula (3):

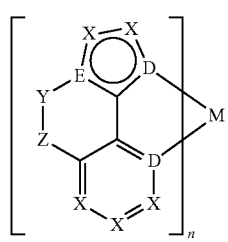

(2)

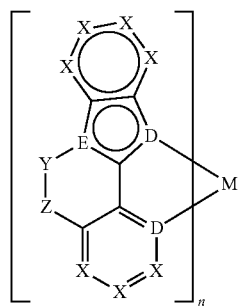

(3)

wherein

M is a transition metal selected from the group consisting of chromium, molybdenum, tungsten, rhenium, osmium, rhodium, iridium, nickel, platinum, copper, silver, and gold;

X is selected on each occurrence, identically or differently, from the group consisting of CR and N;

Y is selected on each occurrence, identically or differently, from the group consisting of $C(R^1)_2$, $Si(R^1)_2$, $PR^1$, $P(=O)R^1$, and $BR^1$;

Z is selected on each occurrence, identically or differently, from the group consisting of $NR^1$ and $C(R^1)_2$, or —Y-Z— is selected on each occurrence, identically or differently, from the group consisting of —$Si(R^1)_2$—O—, —$P(=O)R^1$—O—, and —$BR^1$—O—;

D is on each occurrence, identically or differently, C or N, with the proviso that at least one D is N;

E is on each occurrence, identically or differently, C or N, with the proviso that at least one of E or D in the five-membered ring is N;

R and $R^1$ is on each occurrence, identically or differently, H, D, F, Cl, Br, I, $N(R^2)_2$, CN, $NO_2$, OH, COOH, $C(=O)N(R^2)_2$, $Si(R^2)_3$, $B(OR^2)_2$, $C(=O)R^2$, $P(=O)(R^2)_2$, $S(=O)R^2$, $S(=O)_2R^2$, $OSO_2R^2$, a straight-chain alkyl, alkoxy, or thioalkoxy group having 1 to 20 C atoms or an alkenyl or alkynyl group having 2 to 20 C atoms or a branched or cyclic alkyl, alkoxy, or thioalkoxy group having 3 to 20 C atoms, each of which is optionally substituted by one or more radicals $R^2$, wherein one or more non-adjacent $CH_2$ groups are optionally replaced by $R^2C=CR^2$, $C\equiv C$, $Si(R^2)_2$, $C=O$, $NR^2$, O, S, or $CONR^2$, and wherein one or more H atoms are optionally replaced by D, F, Cl, Br, I, or CN, an aromatic or heteroaromatic ring system having 5 to 60 aromatic ring atoms optionally substituted by one or more radicals $R^2$, an aryloxy or heteroaryloxy group having 5 to 40 aromatic ring atoms optionally substituted by one or more radicals $R^2$, an aralkyl or heteroaralkyl group having 5 to 40 aromatic ring atoms optionally substituted by one or more radicals $R^2$, or a diarylamino group, diheteroarylamino group, or arylheteroarylamino group having 10 to 40 aromatic ring atoms optionally substituted by one or more radicals $R^2$; and wherein two adjacent radicals R or two adjacent radicals $R^1$ optionally define a mono- or polycyclic, aliphatic, aromatic or heteroaromatic ring system with one another; and wherein a radical R and a radical $R^1$ optionally define a mono- or polycyclic, aliphatic or heteroaromatic ring system with one another;

$R^2$ is on each occurrence, identically or differently, H, D, F, Cl, Br, I, $N(R^3)_2$, CN, $NO_2$, $Si(R^3)_3$, $B(OR^3)_2$, $C(=O)R^3$, $P(=O)(R^3)_2$, $S(=O)R^3$, $S(=O)_2R^3$, $OSO_2R^3$, a straight-chain alkyl, alkoxy or thioalkoxy group having 1 to 20 C atoms or an alkenyl or alkynyl group having 2 to 20 C atoms or a branched or cyclic alkyl, alkoxy or thioalkoxy group having 3 to 20 C atoms, each of which is optionally substituted by one or more radicals $R^3$, wherein one or more non-adjacent $CH_2$ groups are optionally replaced by $R^3C=CR^3$, $C\equiv C$, $Si(R^3)_2$, $C=O$, $NR^3$, O, S, or $CONR^3$, and wherein one or more H atoms are optionally replaced by D, F, Cl, Br, I, CN, or $NO_2$, an aromatic or heteroaromatic ring system having 5 to 60 aromatic ring atoms optionally substituted by one or more radicals $R^3$, an aryloxy or heteroaryloxy group having 5 to 40 aromatic ring atoms optionally substituted by one or more radicals $R^3$, an aralkyl or heteroaralkyl group having 5 to 40 aromatic ring atoms optionally substituted by one or more radicals $R^3$, or a diarylamino group, diheteroarylamino group, or arylheteroarylamino group having 10 to 40 aromatic ring atoms optionally be substituted by one or more radicals $R^3$; and wherein two or more adjacent radicals $R^2$ with one another or a radical $R^2$ and a radical R or a radical $R^1$ optionally define a mono- or polycyclic, aliphatic, aromatic, or heteroaromatic ring system;

$R^3$ is on each occurrence, identically or differently, H, D, F, or an aliphatic, aromatic, and/or heteroaromatic hydrocarbon radical having 1 to 20 C atoms, wherein one or more H atoms is optionally replaced by F; and wherein two or more substituents $R^3$ optionally define a mono- or polycyclic, aliphatic ring system with one another;

L' is, identically or differently on each occurrence, any desired co-ligand;

n is 1, 2, or 3;

m is 0, 1, 2, 3, or 4;

wherein a plurality of ligands L with one another or a ligand L with a ligand L' are optionally linked via a single bond or a divalent or trivalent bridge to form a tridentate, tetradentate, pentadentate, or hexadentate ligand system, wherein L' is not a separate co-ligand, but instead a coordinating group; and wherein a substituent R is optionally additionally coordinated to M.

2. The compound of claim 1, wherein M is selected from the group consisting of molybdenum, tungsten, rhenium, osmium, iridium, copper, platinum, and gold.

3. The compound of claim 1, wherein the moiety of formula (2) is selected from the group consisting of moieties of formulae (2a), (2b), and (2c) and the moiety of formula (3) is selected from the group consisting of moieties of formulae (3a), (3b), and (3c):

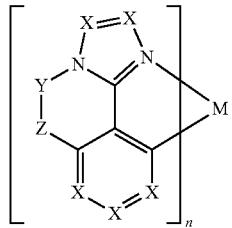

(2a)

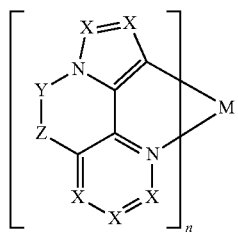

(2b)

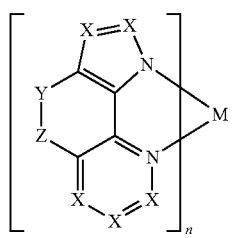

(2c)

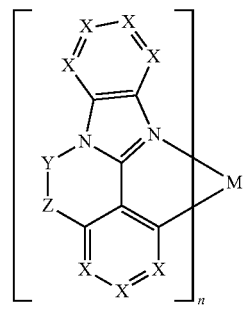

(3a)

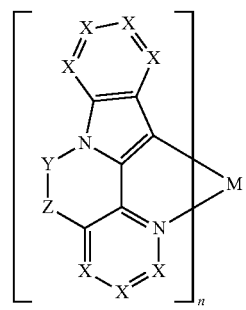

(3b)

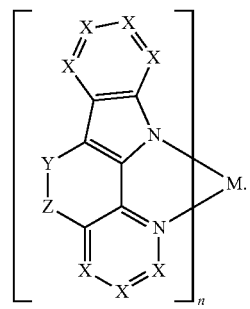

(3c)

4. The compound of claim 1, wherein the group —Y—Z— is, identically or differently on each occurrence, —C(R$^1$)$_2$—NR$^1$—, —Si(R$^1$)$_2$—NR$^1$—, —Si(R$^1$)$_2$—O—, or —C(R$^1$)$_2$—C(R$^1$)$_2$—.

5. The compound of claim 1, wherein $R^1$ is selected, identically or differently on each occurrence, from the group consisting of F, CN, a straight-chain alkyl group having 1 to 10 C atoms or a branched or cyclic alkyl group having 3 to 10 C atoms, each of which is optionally substituted by one or more radicals $R^2$, wherein one or more non-adjacent CH$_2$ groups are optionally replaced by R$^2$C=CR$^2$, and wherein one or more H atoms are optionally replaced by F, an aromatic or heteroaromatic ring system having 5 to 30 aromatic ring atoms optionally substituted by one or more radicals $R^2$, an aryloxy or heteroaryloxy group having 5 to 30 aromatic ring atoms optionally substituted by one or more radicals $R^2$, an aralkyl or heteroaralkyl group having 5 to 40 aromatic ring atoms optionally substituted by one or more radicals $R^2$, or a diarylamino group, diheteroarylamino group, or arylheteroarylamino group having 10 to 30 aromatic ring atoms optionally substituted by one or more radicals $R^2$; and wherein two adjacent radicals $R^1$ optionally define a mono- or polycyclic, aliphatic, aromatic, or heteroaromatic ring system with one another; and wherein a radical R and a radical $R^1$ optionally define a mono- or polycyclic, aliphatic or heteroaromatic ring system with one another.

6. The compound of claim 1, wherein 0, 1, or 2 groups X in the ligand L is N.
7. The compound of claim 1, wherein the moiety of formula (2) is selected from the group consisting of moieties of formulae (2-A) to (2-G) and the moiety of formula (3) is selected from the group consisting of moieties of formulae (3-A) to (3-H):
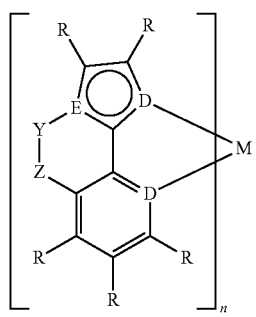
(2-A)
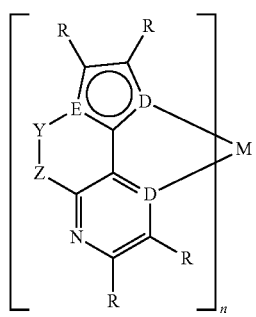
(2-B)
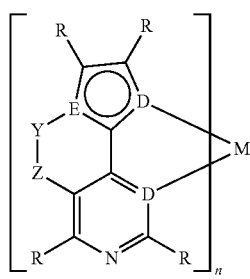
(2-C)
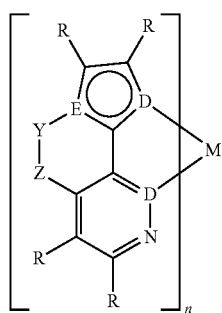
(2-D)
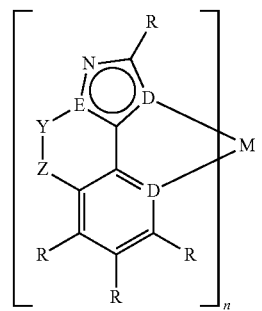
(2-E)
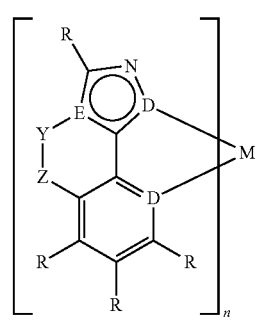
(2-F)
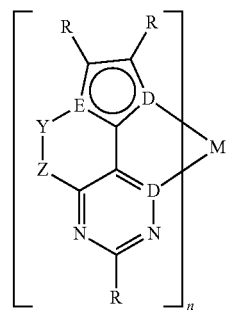
(2-G)
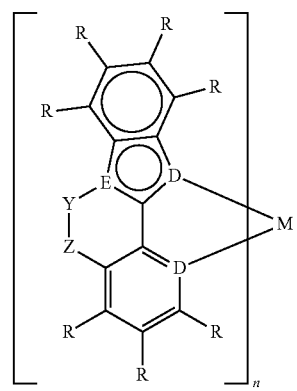
(3-A)

(3-B) 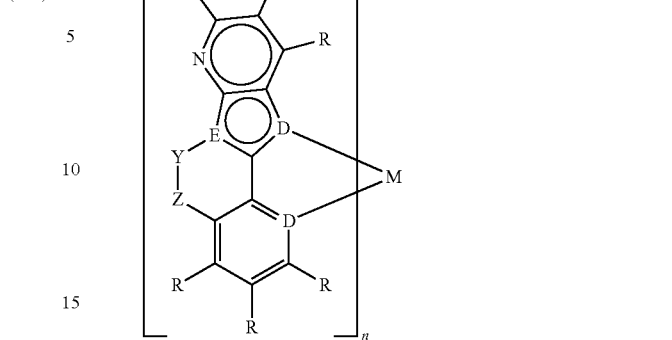

(3-C) 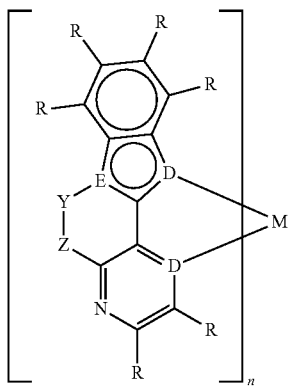

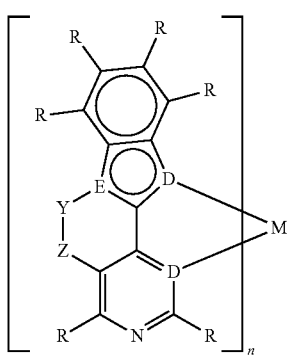

(3-D) 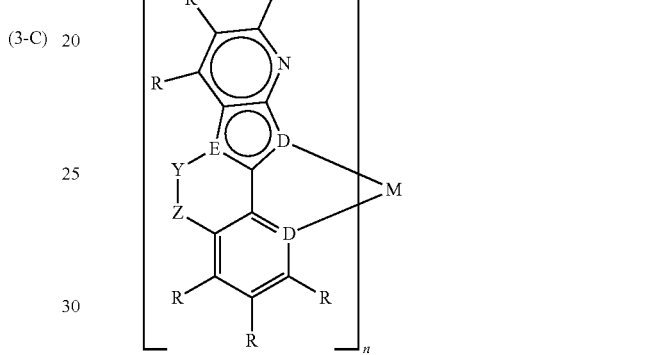

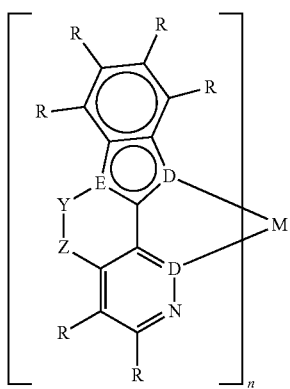

(3-F) (already labeled above)

(3-G) 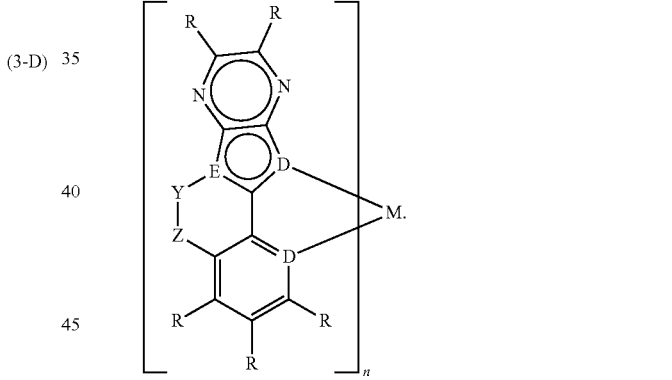

(3-H) (shown within image 7)

(3-E) 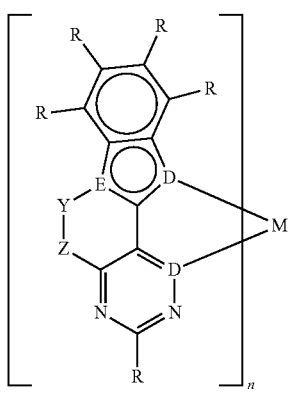

8. The compound of claim 1, wherein E is N and either the D in the five-membered ring or the D in the six-membered ring is N, while the other D is C, or E is C and both D are N.

9. The compound of claim 1, wherein, if one or more X is N, a group R which is not H or D is bonded as a substituent adjacent to this nitrogen atom.

10. The compound of claim 9, wherein, if one or more X is N, a group selected from the group consisting of $CF_3$, $OCF_3$, alkyl or alkoxy groups having 1 to 10 C atoms, aromatic or heteroaromatic ring systems or aralkyl or heteroaralkyl groups, wherein these groups are each optionally substituted by one or more radicals $R^2$, is bonded as a substituent adjacent to this nitrogen atom.

11. The compound of claim 10, wherein the alkyl or alkoxy groups are branched or cyclic alkyl or alkoxy groups having 3 to 10 C atoms.

12. The compound of claim 1, wherein two adjacent X are CR and the respective radicals R, together with the C atoms, define a ring of formula (4) or formula (5),

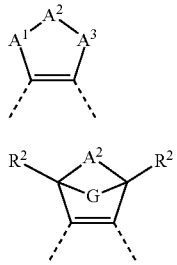

(4)

(5)

wherein
the dashed bonds indicate the linking of the two carbon atoms in the ligand;
$A^1$ and $A^3$ are, identically or differently on each occurrence, $C(R^4)_2$, O, S, $NR^4$, or C(=O);
$A^2$ is $C(R^2)_2$, O, S, $NR^4$, or C(=O);
G is an alkylene group having 1, 2 or 3 C atoms optionally substituted by one or more radicals $R^3$, or is —$CR^3$=$CR^3$— or an ortho-linked arylene or heteroarylene group having 5 to 14 aromatic ring atoms optionally substituted by one or more radicals $R^3$;
$R^4$ is, identically or differently on each occurrence, F, a straight-chain alkyl or alkoxy group having 1 to 20 C atoms or a branched or cyclic alkyl or alkoxy group having 3 to 20 C atoms, each of which is optionally substituted by one or more radicals $R^3$, wherein one or more non-adjacent $CH_2$ groups are optionally replaced by $R^3C$=$CR^3$, C≡C, $Si(R^3)_2$, C=O, $NR^3$, O, S, or $CONR^3$ and wherein one or more H atoms are optionally replaced by D or F, an aromatic or heteroaromatic ring system having 5 to 24 aromatic ring atoms optionally substituted by one or more radicals $R^3$, an aryloxy or heteroaryloxy group having 5 to 24 aromatic ring atoms optionally substituted by one or more radicals $R^3$, or an aralkyl or heteroaralkyl group having 5 to 24 aromatic ring atoms optionally substituted by one or more radicals $R^3$; and wherein two radicals $R^4$ which are bonded to the same carbon atom optionally define an aliphatic or aromatic ring system with one another here to form a spiro system; and wherein $R^4$ optionally defines an aliphatic ring system with an adjacent radical R, $R^1$ or $R^2$;
with the proviso that no two heteroatoms in $A^1$-$A^2$-$A^3$ are bonded directly to one another.

13. The compound of claim 1, wherein the compound is selected from the group consisting of the structures of formulae (12) to (23):

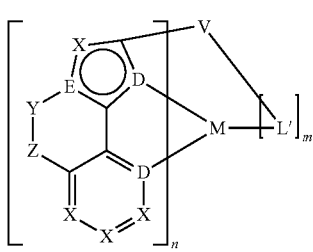

(12)

-continued

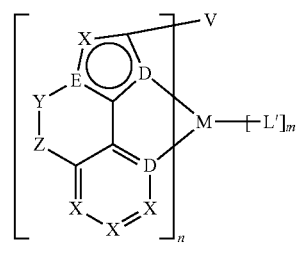

(13)

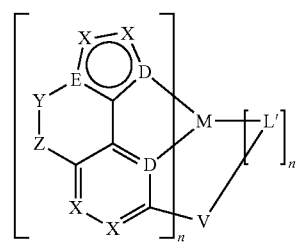

(14)

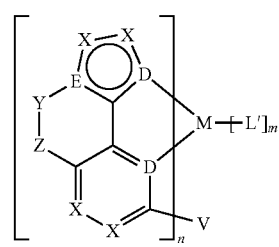

(15)

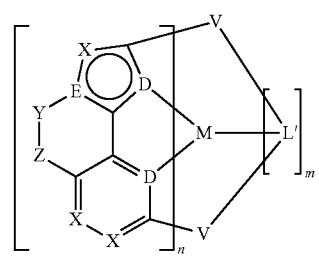

(16)

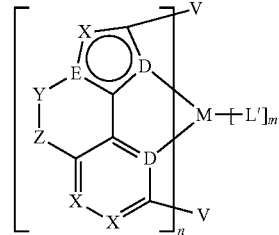

(17)

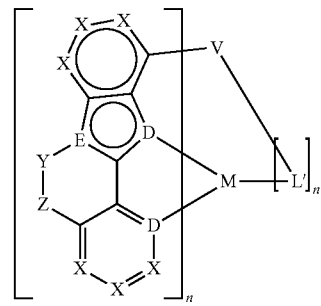

(18)

-continued

(19)
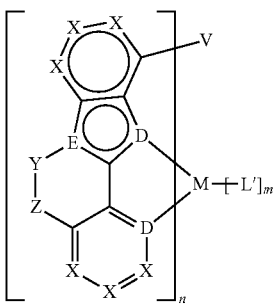

(20)
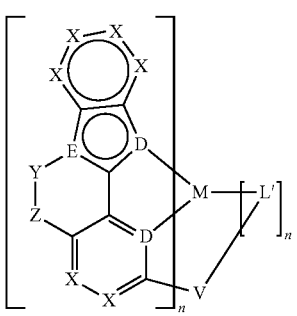

(21)
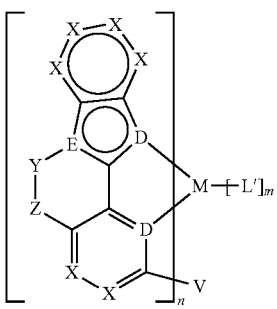

(22)
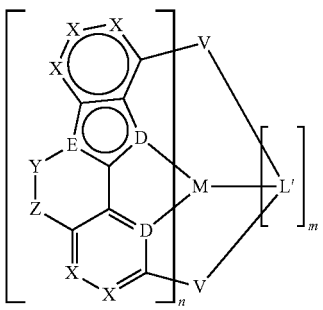

(23)
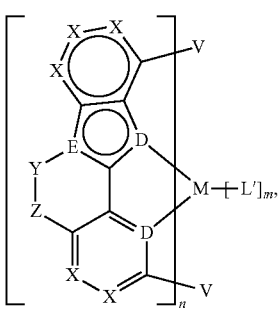

wherein
V is a single bond or a bridging unit containing 1 to 80 atoms from the third, fourth, fifth and/or sixth main group (group 13, 14, 15 or 16 in accordance with IUPAC) or a 3- to 6-membered homo- or heterocycle which covalently bonds the part-ligands L to one another or L to L'.

14. The compound of claim 1, wherein the ligands L' are selected from the group consisting of carbon monoxide, nitrogen monoxide, alkyl cyanides, aryl cyanides, alkyl isocyanides, aryl isocyanides, amines, phosphines, phosphites, arsines, stibines, nitrogen-containing heterocycles, carbenes, hydride, deuteride, $F^-$, $Cl^-$, $Br^-$, $I^-$, alkylacetylides, arylacetylides, cyanide, cyanate, isocyanate, thiocyanate, isothiocyanate, aliphatic alcoholates, aromatic alcoholates, aliphatic thioalcoholates, aromatic thioalcoholates, amides, carboxylates, aryl groups, $O^{2-}$, $S^{2-}$, carbides, nitrenes, $N^{3-}$, diamines, imines, diimines, heterocycles containing two nitrogen atoms, diphos-phines, 1,3-diketonates derived from 1,3-diketones, 3-ketonates derived from 3-keto-esters, carboxylates derived from aminocarboxylic acids, salicyliminates derived from salicylimines, dialcoholates derived from dialcohols, dithiolates derived from dithiols, bis(pyrazolyl boraten), bis(imidazolyl) boraten, 3-(2-pyridyl)diazoles, 3-(2-pyridyl)triazoles, bidentate monoanionic, neutral ligands, and dianionic ligands.

15. The compound of claim 14, wherein the ligands L' are monoanionic ligands, which, with M, define a cyclometallated five-membered ring or six-membered ring having at least one metal-carbon bond.

16. A process for preparing a compound of claim 1 comprising reacting a free ligand L and optionally L' with a metal alkoxide of formula (75), a metal ketoketonate of formula (76), a metal halides of formula (77), a dimeric metal complex of formula (78), or a metal complex of formula (79):

$$M(OR)_n \tag{75}$$

(76)
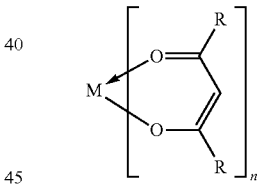

$$MHal_n \tag{77}$$

(78)

(79)
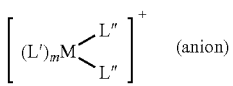

wherein
Hal is F, Cl, Br, or I;
L" is an alcohol or a nitrile; and
(anion) is a non-coordinating anion.

17. An oligomer, polymer, or dendrimer comprising one or more compounds of claim 1, wherein one or more bonds are present from the compound to the polymer, oligomer, or dendrimer.

18. A formulation comprising the oligomer, polymer, or dendrimer of claim 17 and at least one further compound.

19. The formulation of claim 18, wherein the at least one further compound is a solvent and/or a further organic or inorganic compound.

20. An electronic device comprising in at least one layer at least one oligomer, polymer, or dendrimer of claim 17.

21. The electronic device of claim 20, wherein the device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

22. A formulation comprising the compound of claim 1 and at least one further compound.

23. The formulation of claim 22, wherein the at least one further compound is a solvent and/or a further organic or inorganic compound.

24. An electronic device comprising in at least one layer at least one compound of claim 1.

25. The electronic device of claim 24, wherein the device is selected from the group consisting of organic electroluminescent devices, organic integrated circuits, organic field-effect transistors, organic thin-film transistors, organic light-emitting transistors, organic solar cells, organic optical detectors, organic photoreceptors, organic field-quench devices, light-emitting electrochemical cells, and organic laser diodes.

* * * * *